United States Patent
Asahara et al.

(10) Patent No.: US 8,309,329 B2
(45) Date of Patent: Nov. 13, 2012

(54) PROCESS FOR PRODUCTION OF 5'-GUANYLIC ACID

(75) Inventors: Takayuki Asahara, Kawasaki (JP); Hiroaki Fukada, Kawasaki (JP); Kiyoshi Matsuno, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 78 days.

(21) Appl. No.: 12/861,939

(22) Filed: Aug. 24, 2010

(65) Prior Publication Data

US 2011/0045543 A1  Feb. 24, 2011

Related U.S. Application Data

(63) Continuation of application No. PCT/JP2009/053358, filed on Feb. 25, 2009.

(30) Foreign Application Priority Data

Feb. 25, 2008 (JP) ................................ 2008-043136

(51) Int. Cl.
  *C12P 19/38* (2006.01)
  *C12N 9/00* (2006.01)
(52) U.S. Cl. ............... 435/87; 435/92; 435/26; 435/183
(58) Field of Classification Search .................... 435/87, 435/92
See application file for complete search history.

(56) References Cited

U.S. PATENT DOCUMENTS

| | | | |
|---|---|---|---|
| 7,211,416 | B2 | 5/2007 | Asahara et |
| 7,326,546 | B2 | 2/2008 | Matsuno et al. |
| 2002/0098494 | A1 | 7/2002 | Kakehi et al. |
| 2004/0152171 | A1 | 8/2004 | Kakehi et al. |
| 2008/0026428 | A1 | 1/2008 | Kakehi et al. |
| 2009/0104665 | A1 | 4/2009 | Asahara et al. |
| 2009/0186384 | A1 | 7/2009 | Matsuno et al. |
| 2010/0047874 | A1 | 2/2010 | Asahara et al. |

FOREIGN PATENT DOCUMENTS

| | | |
|---|---|---|
| CN | 1335403 | 2/2002 |
| EP | 0 185 092 | 6/1986 |
| EP | 0 251 489 | 1/1988 |
| EP | 0 832 970 | 4/1998 |
| EP | 0 857 788 | 8/1998 |
| EP | 1 170 370 | 1/2002 |
| JP | 56-12438 | 3/1981 |
| JP | 63-233798 | 9/1988 |
| JP | 3-28196 | 4/1991 |
| JP | 07-231793 | 9/1995 |
| JP | 2602927 | 1/1997 |
| JP | 10-201481 | 8/1998 |
| JP | 2000-135097 | 5/2000 |
| JP | 2001-245676 | 9/2001 |
| JP | 2002-355087 | 12/2002 |
| JP | 2007-105056 | 4/2007 |
| KR | 1993-0002508 | 2/1993 |
| WO | WO96/37603 | 11/1996 |

OTHER PUBLICATIONS

Tremblay, L. W., et al., "Structure and Activity Analyses of *Escherichia coli* K-12 NagD Provide Insight into the Evolution of Biochemical Function in the Haloalkanoic Acid Dehalogenase Superfamily," Biochem. 2006;45(4):1183-1193.
Official Communication from Chinese Patent App. 200980106422.4 (Jun. 22, 2011) with English translation thereof.
Fujio, T., et al., "High Level Expression of XMP Aminase in *Escherichia coli* and Its Application for the Industrial Production of 5'Guartylic Acid," Biosci. Biotech. Biochem. 1997;61(5):840-845.
Tremblay, L. W., et al., "Structure and Activity Analyses of *Escherichia coli* K-12 NagD Provide Insight into the Evolution of Biochemical Function in the Haloalkanoic Acid Dehalogenase Superfamily," Biochem. 2006;45:1183-1193.
International Search Report for PCT Patent App. No. PCT/JP2009/053358 (Apr. 7, 2009).
Mori, H., et al., "A novel process of inosine 5'-monophosphate production using overexpressed guanosine/inosine kinase," Appl. Microbiol. Biotechnol. 1997;48:693-698.
International Preliminary Report on Patentability for PCT Patent App. No. PCT/JP2009/053358 (Oct. 14, 2010).

*Primary Examiner* — Tekchand Saidha
(74) *Attorney, Agent, or Firm* — Shelly Guest Cermak; Cermak Nakajima LLP

(57) ABSTRACT

By reacting inosinic acid (IMP) with a bacterium which has been modified so that IMP dehydrogenase activity and 5'-guanylic acid (GMP) synthetase activity are enhanced, GMP is produced.

6 Claims, 4 Drawing Sheets

PROCESS FOR PRODUCTION OF 5'-GUANYLIC ACID

This application is a continuation under 35 U.S.C. §120 of PCT Patent Application No. PCT/JP2009/053358, filed Feb. 25, 2009, which claims priority under 35 U.S.C. §119 to Japanese Patent Application Nos. 2008-043136, filed on Feb. 25, 2008, which are incorporated in their entireties by reference. The Sequence Listing in electronic format filed herewith is also hereby incorporated by reference in its entirety (File Name: 2010-08-24T_US-445_Seq_List; File Size: 143 KB; Date Created: Aug. 24, 2010).

BACKGROUND OF THE INVENTION

1. Field of the Invention

The present invention relates to a method for producing 5'-guanylic acid and a novel microorganism used for this production. 5'-guanylic acid is useful as a seasoning, in medicines and as a raw material thereof.

2. Brief Description of the Related Art

Known methods for industrially producing 5'-guanylic acid, also known as guanosine-5'-monophosphate, or "GMP", include producing guanosine by fermentation and then subjecting it to enzymatic phosphorylation, to obtain 5'-guanylic acid (JP 07-231793, JP 10-201481, WO96/37603, and JP 2001-245676).

In addition, other methods of producing GMP have been reported, including culturing both a microorganism belonging to the genus *Escherichia* with increased GMP synthetase activity and a *Brevibacterium ammoniagenes* which is able to biosynthesize large amounts of adenosine triphosphate (ATP) (hereinafter referred to as the "regeneration of ATP") in a culture medium containing 5'-xanthylic acid (XMP) and ammonia or glutamine. ATP is generated by glucose metabolism and is necessary for the synthesis of GMP from 5'-xanthylic acid (XMP), and GMP is generated and accumulated in the medium by converting XMP to GMP with high efficiency (Tatsuro Fujio et al., Biosci. Biotech. Biochem., 1997, Vol. 61, No. 5, p. 840-845).

Methods for producing GMP by fermentation have also been suggested. For example, JP 56-12438 discloses a method for producing GMP wherein a mutant strain of the genus *Bacillus* having adenine auxotrophy and resistance to decoyinine or methionine sulfoxide is cultured, followed by collecting the GMP that is generated from the medium. Also, JP 2002-355087 discloses a method for producing GMP characterized by culturing a strain of bacteria belonging to the genus *Escherichia* which is able to produce inosinic acid (inosine 5'-monophosphate, hereinafter referred to as "IMP"), wherein two types of 5'-nucleotidase genes are deleted and the IMP dehydrogenase and GMP synthetase genes are amplified, and collecting the GMP that is generated from the medium. Yet, in general, direct fermentation of GMP does not provide a sufficient yield and is not necessarily practical compared with the above-described enzymatic method.

Thus far, production of GMP from IMP as a raw material by using bacteria belonging to the genus *Escherichia* with enhanced activities of IMP dehydrogenase and GMP synthetase has not been previously reported.

SUMMARY OF THE INVENTION

The present invention describes a novel microorganism that can be used in a method for producing GMP from IMP with high efficiency.

It has been found that by using a microorganism belonging to the genus *Escherichia*, which has been modified so that IMP dehydrogenase activity and GMP synthetase activity are enhanced, IMP is converted to GMP with high efficiency and at high speed. Hence, a novel microorganism is described which is capable of converting IMP to GMP efficiently.

It is an aspect of the present invention to provide a method for producing 5'-guanylic acid, comprising reacting inosinic acid with a microorganism which is able to convert inosinic acid into 5'-guanylic acid, and collecting 5'-guanylic acid; wherein said microorganism has been modified so that inosinic acid dehydrogenase activity and 5'-guanylic acid synthetase activity are enhanced.

It is another aspect of the present invention to provide the method as described above, wherein inosinic acid dehydrogenase activity and 5'-guanylic acid synthetase activity are enhanced by increasing expression of a guaB gene and guaA gene.

It is another aspect of the present invention to provide the method as described above, wherein said guaA gene encodes a protein selected from the group consisting of:

(A) a protein comprising the amino acid sequence of SEQ ID NO: 2, and (B) a protein comprising the amino acid sequence of SEQ ID NO: 2 but which includes substitution, deletion, insertion, addition or inversion of one or several amino acids, and has 5'-guanylic acid synthetase activity.

It is another aspect of the present invention to provide the method as described above, wherein said guaB gene encodes a protein selected from the group consisting of:

(C) A protein comprising the amino acid sequence of SEQ ID NO: 10, and (D) A protein comprising the amino acid sequence of SEQ ID NO: 10 but which includes substitution, deletion, insertion, addition or inversion of one or several amino acids, and has inosinic acid dehydrogenase activity.

It is another aspect of the present invention to provide the method as described above, wherein said microorganism has been further modified so that a gene selected from the group consisting of ushA, aphA, and combinations thereof do not function normally.

It is another aspect of the present invention to provide the method as described above, wherein said microorganism has been further modified so that a gene selected from the group consisting of purR, add, purA, and combinations thereof do not function normally.

It is another aspect of the present invention to provide the method as described above, wherein said microorganism has been further modified so that nagD gene does not function normally.

It is another aspect of the present invention to provide the method as described above, wherein said microorganism is selected from the group consisting of bacteria belonging to the Enterobacteriaceae family, *Bacillus* bacteria and Coryneform bacteria.

It is another aspect of the present invention to provide the method as described above, wherein said microorganism is an *Escherichia* bacterium.

It is another aspect of the present invention to provide the method as described above, wherein said microorganism is *Escherichia coli*.

It is another aspect of the present invention to provide a microorganism having an ability to convert inosinic acid into 5'-guanylic acid, which has been modified so that inosinic acid dehydrogenase activity and 5'-guanylic acid synthetase activity are enhanced by increasing expression of guaB gene and guaA gene, and has been further modified so that ushA gene, aphA gene and nagD gene do not function normally.

It is another aspect of the present invention to provide the microorganism as described above, which has been further modified so that a gene selected from the group consisting of purR, add, purA, and combinations thereof do not function normally.

It is another aspect of the present invention to provide the microorganism as described above, which is selected from the group consisting of bacteria belonging to the Enterobacteriaceae family, *Bacillus* bacteria and Coryneform bacteria.

It is another aspect of the present invention to provide the microorganism as described above which is an *Escherichia* bacterium.

It is another aspect of the present invention to provide the microorganism as described above which is an *Escherichia coli*.

DESCRIPTION OF THE PREFERRED EMBODIMENTS

Figure 1:
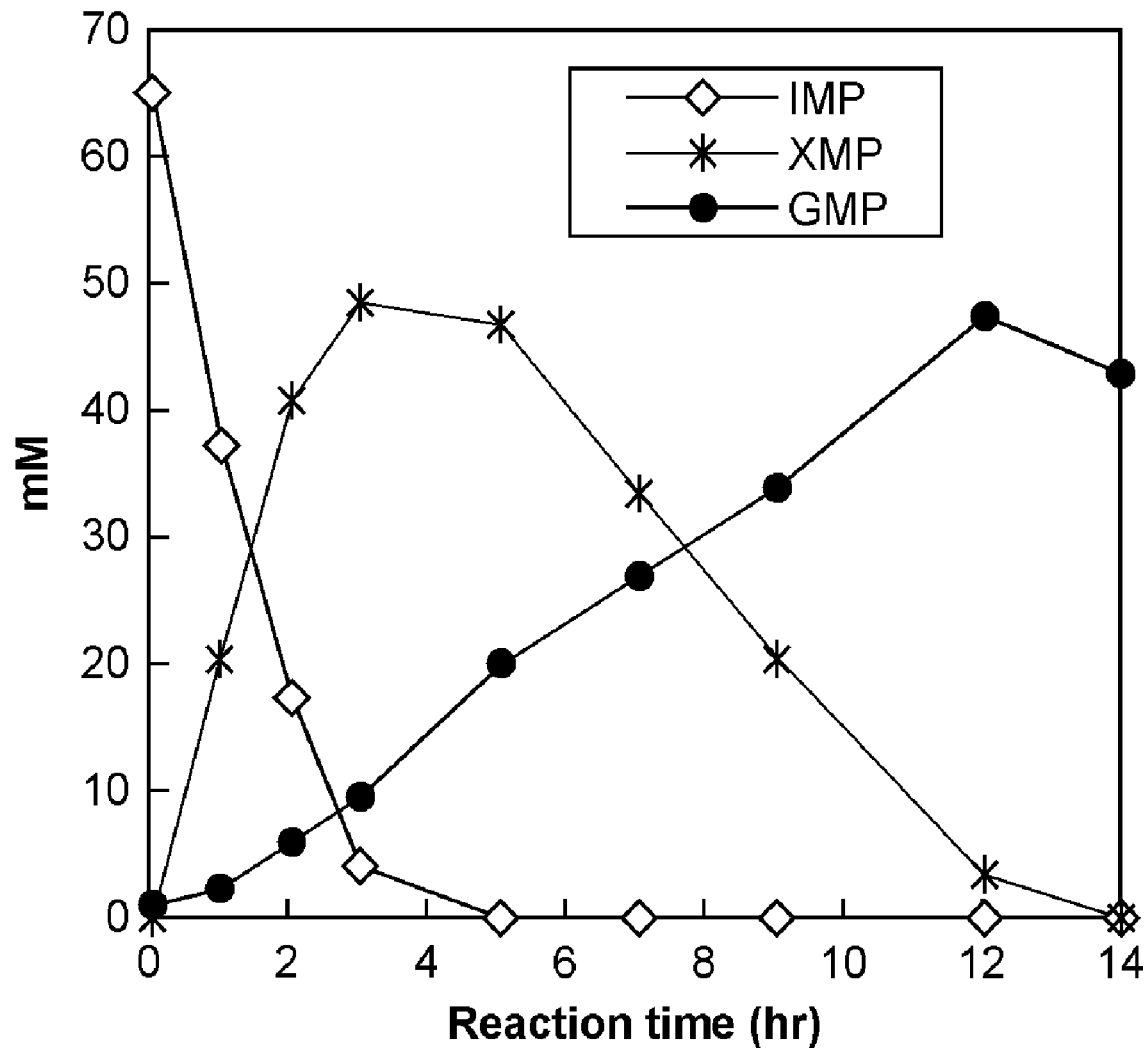
FIG. 1 is a graph showing the change in the concentration of IMP, XMP and GMP when the JM109ΔushAΔaphAΔpurR/pUC18-guaBA strain was reacted with IMP.

The present invention will now be described in detail.
<I> Microorganism

A microorganism is described which has been modified so that IMP dehydrogenase activity and GMP synthetase activity are enhanced, and is able to convert IMP to GMP.

Examples of the microorganism include bacteria belonging to the family Enterobacteriaceae, Coryneform bacteria, and *Bacillus* bacteria.

Examples of the bacteria belonging to the family Enterobacteriaceae include *Escherichia* bacteria, *Pantoea* bacteria, *Enterobacter* bacteria, *Klebsiella* bacteria, *Serratia* bacteria, *Erwinia* bacteria, *Salmonella* bacteria and *Morganella* bacteria. *Escherichia* bacteria are not restricted as long as they belong to the genus *Escherichia*, and include *Escherichia coli*. Yet, specifically, bacteria described in Neidhardt et al. (Neidhardt, F R. C. et al., *Escherichia coli* and *Salmonella Typhimurium*, American Society for Microbiology, Washington D.C., 1208, table 1) can be used. Also, examples of *Enterobacter* bacteria include *Enterobacter agglomerans*, *Enterobacter aerogenes* and the like, and examples of *Pantoea* bacteria include *Pantoea ananatis* and the like.

Examples of Coryneform bacteria include bacteria classified as Coryneform bacteria according to classification known to those skilled in the art of microorganisms, bacteria which used to be classified as the genus *Brevibacterium* but currently re-classified as the genus *Corynebacterium* (Int. J. Syst. Bacteriol., 41, 255 (1991)) and bacteria belonging to the genus *Brevibacterium* which is close to the genus *Corynebacterium*. Examples of such Coryneform bacteria are listed below.

*Corynebacterium acetoacidophilum*,
*Corynebacterium acetoglutamicum*,
*Corynebacterium alkanolyticum*,
*Corynebacterium callunae*,
*Corynebacterium glutamicum*,
*Corynebacterium lilium*,
*Corynebacterium melassecola*,
*Corynebacterium thermoaminogenes*,
*Corynebacterium harculis*,
*Brevibacterium divaricatum*,
*Brevibacterium flavum*,
*Brevibacterium immariophilum*,
*Brevibacterium lactofermentum*,
*Brevibacterium roseum*,
*Brevibacterium saccharolyticum*,
*Brevibacterium thiogenitalis*,
*Corynebacterium ammoniagenes*,
*Brevibacterium album*,
*Brevibacterium cerinum*,
*Microbacterium ammoniaphilum*, Furthermore, bacteria classified as the genus *Bacillus* according to the classification known to those skilled in the art of microorganisms can be used. Specific examples include, but are not limited to, *Bacillus subtilis*, *Bacillus amyloliquefaciens*, and the like.

Methods for enhancing activities of IMP dehydrogenase (a product of the guaB gene) and GMP synthetase (a product of the guaA gene) in the above-mentioned microorganisms will now be described.

The phrase "modified so that the IMP dehydrogenase activity and GMP synthetase activity are enhanced" means that IMP dehydrogenase activity and GMP synthetase activity are higher than those of an unmodified strain, for example a wild-type strain, of microorganisms such as bacteria belonging to the genus *Escherichia*.

IMP dehydrogenase is an enzyme catalyzing the reaction below and "IMP dehydrogenase activity" refers to an activity catalyzing a reaction generating XMP from IMP. The IMP dehydrogenase activity can be measured, for example, by the method of Gilbert (Gilbert, H. J., Lowe, C. R. and Drabble, W. T., Biochem J., 1979, Dec. 1, 183(3), 481-94).

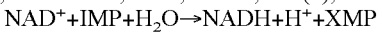
$NAD^+ + IMP + H_2O \rightarrow NADH + H^+ + XMP$

Also, GMP synthetase is an enzyme (EC 6.3.4.1) catalyzing the reaction below and "GMP synthetase activity" means an activity catalyzing a reaction generating GMP from XMP.

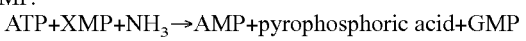
$ATP + XMP + NH_3 \rightarrow AMP + pyrophosphoric\ acid + GMP$

The GMP synthetase activity can be measured, for example, by examining the rate of decrease of NADH by the method of Spector (Spector, T., Methods Enzymol., 1978, 51, p 219).

In order to increase IMP dehydrogenase activity and GMP synthetase activity, expression of the guaB and guaA genes can be increased. Examples of methods for increasing the gene expression level include increasing the copy number of the DNAs encoding IMP dehydrogenase GMP synthetase in bacterial cells. In order to increase the copy number in the cells, DNA fragments encoding IMP dehydrogenase or GMP synthetase may be linked to a vector which is able to function in the chosen microorganism, such as *Escherichia* bacteria, to create a recombinant DNA, which is then used to transform the chosen host cell. The copy number of the guaB and guaA genes can be simultaneously or independently increased. In the case of *Escherichia coli*, the guaB and guaA genes form an operon (GenBank accession No. M10101), and the guaBA operon can be linked to a vector to create a recombinant DNA, which is then used to transform the chosen host. The copy number of the genes encoding IMP dehydrogenase and GMP synthetase (guaB gene and guaA gene) increases in cells of a transformed strain, resulting in increased activities of IMP dehydrogenase and GMP synthetase.

The copy number in the cells can also be increased by placing multiple copies of the IMP dehydrogenase and GMP synthetase genes on the chromosomal DNA of the above-mentioned host. Multiple copies of these genes can be placed on the chromosomal DNA of bacteria belonging to the genus *Escherichia* by homologous recombination using a target sequence which is present on the chromosome in multiple copies. Sequences that are present on the chromosome in multiple copies include repetitive DNAs, inverted repeats present at the end of transposons, or the like. Alternatively, as disclosed in Japanese Patent Application Laid-Open Publication No. 2-109985, multiple copies of the desired gene(s) can also be introduced on the choromosomal DNA by integrating the desired gene(s) into the transposon and then transferring the gene(s). Either way, an increase in the copy number of the IMP dehydrogenase and GMP synthetase genes in the trans-formant strain results in increased activities of IMP dehydrogenase and GMP synthetase.

Examples of the vector for introducing the gene(s) include plasmid vectors such as pSTV29, pMW218, or pUC19; and phage vectors such as λ1059, λBF101, or M13mp9. Also, examples of the transposon include Mu, Tn10, and Tn5.

Since the nucleotide sequences of the DNAs encoding IMP dehydrogenase and GMP synthetase are known, the DNAs can be obtained by synthesizing primers based on the known sequences, and the sequences can be amplified by PCR using the chromosomal DNA of microorganisms such as an *Escherichia* bacterium as the template. An example of the guaA gene of *Escherichia coli* includes DNA including the nucleotide sequence of SEQ ID NO: 1. An example of the guaB gene of *Escherichia coli* includes DNA including the nucleotide sequence of SEQ ID NO: 9. As for these genes, the desired DNA fragments can be selected by preparing probes based on the nucleotide sequence and carrying out hybridization from a chromosomal DNA library of *Escherichia* bacterium. Alternatively, the DNA fragments encoding IMP dehydrogenase and GMP synthetase may be chemically synthesized based on the known nucleotide sequences. Also, the guaBA operon of *Escherichia coli* can be cloned using the primers of SEQ ID NOs: 31 and 32.

In addition, genes encoding proteins having functions equivalent to IMP dehydrogenase and GMP synthetase from microorganisms other than *Escherichia* bacteria may be obtained based on the above-mentioned nucleotide sequences.

An example of the GMP synthetase gene (guaA) of *Bacillus subtilis* includes a DNA including the nucleotide sequence of SEQ ID NO: 3. The amino acid sequence encoded by this nucleotide sequence is shown in SEQ ID NO: 4. An example of the GMP synthetase gene (guaA) of *Corynebacterium glutamicum* includes a DNA including the nucleotide sequence shown in SEQ ID NO: 5. The amino acid sequence encoded by this nucleotide sequence is shown in SEQ ID NO: 6.

An example of the GMP synthetase gene (guaA) of *Corynebacterium ammoniagenes* includes a DNA including the nucleotide sequence of SEQ ID NO: 7. The amino acid sequence encoded by this nucleotide sequence is shown in SEQ ID NO: 8.

An example of the IMP dehydrogenase gene (guaB) of *Bacillus subtilis* includes a DNA including the nucleotide sequence of SEQ ID NO: 11. The amino acid sequence encoded by this nucleotide sequence is shown in SEQ ID NO: 10.

An example of IMP dehydrogenase gene (guaB) of *Corynebacterium glutamicum* includes a DNA including the nucleotide sequence of SEQ ID NO: 13. The amino acid sequence encoded by this nucleotide sequence is shown in SEQ ID NO: 14.

An example of the IMP dehydrogenase gene (guaB) of *Corynebacterium ammoniagenes* includes a DNA including the nucleotide sequence of SEQ ID NO: 15. The amino acid sequence encoded by this nucleotide sequence is shown in SEQ ID NO: 16. As described above, since there may be differences in the nucleotide sequences of the guaA and guaB genes depending on the genus, species, or strain of the microorganism, the guaA and guaB genes can be variants of the above-mentioned gene.

As long as the protein encoded by the guaA gene has GMP synthetase activity, it can have a sequence identity of not less than 80%, and in other examples, not less than 90%, not less than 95%, or even not less than 98% to the entire amino acid sequence of SEQ ID NO: 2. Also, as long as the protein encoded by the guaB gene has IMP dehydrogenase activity, it can have a sequence identity of not less than 80%, and in other examples, not less than 90%, not less than 95%, or even not less than 98% to the entire amino acid sequence of SEQ ID NO: 10. The identity of amino acid sequences and of nucleotide sequences can be determined by using, for example, algorithm BLAST by Karlin and Altschul (Pro. Natl. Acad. Sci. USA, 90, 5873 (1993)) or FASTA by Pearson (Methods Enzymol., 183, 63 (1990)). Based on this algorithm BLAST, programs called BLASTN and BLASTX have been developed (See www.ncbi.nlm.nih.gov).

Further, the guaA and guaB genes are not limited to the wild-type genes. As long as the function of the encoded protein, that is, GMP synthetase activity or IMP dehydrogenase activity, is not impaired, the gene may be a mutant or artificially modified, and encodes a protein which includes the amino acid sequence of SEQ ID NO: 2 or 10, but which includes substitution, deletion, insertion, addition or inversion of one or several amino acids at one or more positions. The term, "several" varies depending on the position of the amino acid residues in a spatial structure of the protein and the type of the amino acid residues, and specifically can mean 2 to 20 amino acids, 2 to 10 amino acids, or 2 to 5 amino acids. The substitution can be a conservative substitution, and the term "conservative substitution" can mean mutual substitution among Phe, Trp and Tyr in cases where the substitution site has an aromatic amino acid, among Leu, Ile and Val in cases where the substitution site has a hydrophobic amino acid, between Gln and Asn in cases where the substitution site has a polar amino acid, among Lys, Arg and His in cases where the substitution site has a basic amino acid, between Asp and Glu in cases where the substitution site has an acidic amino acid, and between Ser and Thr in cases where the substitution site has an amino acid having a hydroxyl group. Examples of the conservative substitution include substitution of Ala by Ser or Thr, substitution of Arg by Gln, His or Lys, substitution of Asn by Glu, Gln, Lys, His or Asp, substitution of Asp by Asn, Glu or Gln, substitution of Cys by Ser or Ala, substitution of Gln by Asn, Glu, Lys, His, Asp or Arg, substitution of Glu by Gly, Asn, Gln, Lys or Asp, substitution of Gly by Pro, substitution of His by Asn, Lys, Gln, Arg or Tyr, substitution of Ile by Leu, Met, Val or Phe, substitution of Leu by Ile, Met, Val or Phe, substitution of Lys by Asn, Glu, Gln, His or Arg, substitution of Met by Ile, Leu, Val or Phe, substitution of Phe by Trp, Tyr, Met, Ile or Leu, substitution of Ser by Thr or Ala, substitution of Thr by Ser or Ala, substitution of Trp by Phe or Tyr, substitution of Tyr by His, Phe or Trp, and substitution of Val by Met, Ile or Leu. Examples of the substitution, deletion, insertion, addition, inversion or the like of amino acids as described above also include naturally occurring mutations (mutants and variants), such as those based on individual differences and species differences among microorganisms having the guaA or guaB genes.

Also, the guaA or guaB genes can include DNA capable of hybridizing with a complement of the nucleotide sequence of SEQ ID NO: 1 or 9 respectively, or with a probe which can be prepared from the sequence, under stringent conditions and encoding a protein having GMP synthetase activity or IMP dehydrogenase activity. The term, "stringent conditions" can mean conditions under which the so-called specific hybrids form, and non-specific hybrids do not form. It is difficult to clearly express these conditions with numerical values. For example, stringent conditions can include conditions under which DNAs having high identity, for instance, DNAs having an identity of not less than 80%, 90%, 95%, or even 98%, hybridize to each other, and DNAs having an identity of less than that do not hybridize to each other. Alternatively, the stringent conditions can be exemplified by conditions where washing is carried out once, or 2-3 times at a salt concentration and temperature corresponding to ordinary conditions of washing in Southern hybridization, i.e. 60° C., 1×SSC, 0.1% SDS, preferably 0.1×SSC, 0.1% SDS, more preferably 68° C., 0.1×SSC, 0.1% SDS.

Description of the above-mentioned gene variants can be similarly applied to the ushA, aphA, purR, add, purA genes, and other genes that are described herein.

DNA can be introduced into microorganisms by the method of C. T. Chung (C. T. chung et al., Proc. Natl. Acad. Sci. USA, 86, 2172-2175 (1989)), the method of D. M. Morrison (Methods in Enzymology, 68, 326 (1979)), by increasing permeability of the DNA by treating recipient bacterial cells with calcium chloride (Mandel, M. and Higa, A., J. Mol. Biol., 53, 159 (1970)), or the like.

The expression levels of the IMP dehydrogenase and GMP synthetase genes can also be increased by, besides the above-mentioned gene amplification, replacing an expression regulatory sequence, such as a promoter of the IMP dehydrogenase and GMP synthetase genes, on the chromosomal DNA or a plasmid with a stronger one. For instance, the lac promoter, trp promoter, trc promoter, and the like are known as strong promoters. Also, as disclosed in WO00/18935, by introducing nucleotide substitutions of several nucleotides into the promoter region of a gene, it can be made stronger. These promoter substitutions or modifications strengthen expression of the IMP dehydrogenase and GMP synthetase genes and increase the activities of both proteins. The increase in expression level of the guaB and guaA genes can be detected by the Northern method, RT-PCR method, or the like.

Since expression of the guaBA operon encoding IMP dehydrogenase and GMP synthetase, as well as the purine operon, is suppressed by the PurR protein, the purR gene (GenBank accession J04212: SEQ ID NO: 17) encoding the PurR protein can be modified so that it does not function normally, and can be modified to decrease its expression in the chosen bacterial host. The purR gene can be modified so that it does not function normally by the method exemplified below. For instance, by homologous recombination using a gene recombination method (Experiments in Molecular Genetics, Cold Spring Harbor Laboratory press (1972); Matsuyama, S. and Mizushima, S., J. Bacteriol., 162, 1196 (1985)), the purR gene on the chromosome can be replaced with a purR gene which does not function normally (hereinafter, also referred to as a "disrupted purR gene"). In homologous recombination, when a plasmid with a sequence which is homologous to a sequence on the chromosome or the like is introduced into bacteria cells, the recombination takes place at the sequence having the homology at a certain frequency, and the plasmid is entirely incorporated into the chromosome. Thereafter, if further recombination takes place at the site of the homologous sequence on the chromosome, the plasmid is deleted. At that time, depending on the location at which the recombination takes place, the disrupted gene can be incorporated into the chromosome whereas the original native gene can be deleted from the chromosome together with the plasmid. By selecting such a strain, a strain in which the normal purR gene on the chromosome has been replaced with the disrupted purR gene can be obtained.

Examples of such gene substitution using homologous recombination include methods using linear DNA, such as (see WO2005/010175) by combining the "Red-driven integration" method (Proc. Natl. Acad. Sci. USA, 2000, vol. 97, No. 12, p 6640-6645) using an excision system derived from λ phage (J. Bacteriol. 2002 September; 184(18): 5200-3), and a method using a plasmid containing a temperature-sensitive replication origin (Proc. Natl. Acad. Sci. USA, 2000, vol. 97, No. 12, p 6640-6645, U.S. Pat. No. 6,303,383 or Japanese Patent Application Laid-Open Publication No. 05-007491).

Also, site-specific mutagenesis by gene substitution using homologous recombination described above can be carried out by using a plasmid with no replication ability in the chosen host. Also, the purR gene can be disrupted by using a plasmid containing the purR gene in which a marker gene such as a drug resistance gene is also inserted. Also, the plasmid is incapable of replicating in the host microorganism. That is, in a host cell that has been transformed with the above-mentioned plasmid and, as a result, has acquired the drug resistance, the marker gene is incorporated into the chromosomal DNA. Since it is highly likely that this marker gene is incorporated by homologous recombination between the purR gene sequence at both ends, and these genes on the chromosome, a strain containing the disrupted gene can be efficiently selected.

Specifically, the disrupted purR gene can be obtained by decreasing or eliminating the activity of an encoded repressor, or decreasing or eliminating the transcription of the purR gene by deleting a particular region in these genes by restriction enzyme digestion and ligation; by inserting another DNA fragment (such as a marker gene) in the gene; or introducing one or more nucleotide substitutions, deletions, insertions, additions or inversions in a nucleotide sequence of a coding region or promoter region of the purR gene by a site-specific mutagenesis method (Kramer, W. and Frits, H. J., Methods in Enzymology, 154, 350 (1987)) or by treating with a chemical agent such as sodium hypochlorite or hydroxylamine (Shortle, D. and Nathans, D., Proc., Natl., Acad., Sci., U.S.A., 75, 270 (1978)).

The sequence of the purR gene is known and, based on this known sequence, the purR gene can be readily obtained by PCR or hybridization. An example of purR gene of *E. coli* includes a gene encoding the amino acid sequence of SEQ ID NO: 18. For instance, purR gene can be obtained from the chromosomal DNA of *Escherichia coli* by PCR using primers of SEQ ID NOs: 19 and 20.

Also, the purR gene from other microorganisms can be obtained based on the known sequence, or sequence homology with the above-mentioned purR gene of *E. coli*, and this gene can be used for modification of microorganisms.

The purR gene can include an amino acid sequence having an identity of not less than 70%, or in other examples, not less than 80%, not less than 90%, or even not less than 95% to the amino acid sequence of SEQ ID NO: 18.

The disruption of the desired gene can be confirmed by analyzing the gene on the chromosome by Southern blotting or PCR.

Furthermore, a mutant strain which does not produce a functional PurR protein can also be obtained by irradiating the chosen microorganism with UV or treating it with a known mutagen, such as N-methyl-N'-nitrosoguanidine (NTG) or nitrous acid. Also, by introducing one or more nucleotide substitutions, deletions, insertions, additions, or inversions in the PurR binding sequence located upstream of the guaBA operon promoter (M. I. Hutchings, W. T. Drabble, FEMS Microbiology Letters 187 (2000) 115-122), the PurR protein can be modified so it loses its binding ability.

The chosen microorganism can also be modified so that the ushA gene and/or aphA gene do (does) not function normally. A mutant strain or gene recombinant strain of these genes can be obtained by modifying these genes such that activity of 5'-nucleotidase encoded by those genes decreases or disappears, or transcription of these genes decreases or disappears. Such a mutant strain or gene recombinant strain can be obtained in the same manner as the mutant strain or gene recombinant strain described above in which the purR gene does not function normally.

The sequence of the ushA gene is known, and based on this sequence, the ushA gene can be readily obtained by PCR or hybridization. An example of the ushA gene from *E. coli* includes a gene encoding the amino acid sequence of SEQ ID NO: 22.

Also, the ushA gene from other microorganisms can be obtained based on the known sequence, or sequence homology with the above-mentioned ushA gene from *E. coli*, and this gene can be used for modification of microorganisms.

The ushA gene can also include an amino acid sequence having an identity of not less than 70%, or in other examples, not less than 80%, not less than 90%, or even not less than 95% to the amino acid sequence of SEQ ID NO: 22.

The sequence of the aphA gene is known, and based on this sequence, the aphA gene can be readily obtained by PCR or hybridization. An example of the aphA gene from *E. coli* includes a gene encoding the amino acid sequence of SEQ ID NO: 24.

Also, the aphA gene from other microorganisms can be obtained based on the known sequence, or sequence homology with the above-mentioned aphA gene from *E. coli*, and this gene can be used for modification of microorganisms.

The aphA gene can include an amino acid sequence having an identity of not less than 70%, or in other examples, not less than 80%, not less than 90%, or even not less than 95% to the amino acid sequence of SEQ ID NO: 24.

The microorganism can also be modified so that the add gene and/or purA gene do (does) not function normally. A mutant strain or gene recombinant strain of these genes can be obtained by modifying these genes such that activity of adenosine deaminase and/or succinyl AMP synthase encoded by these genes decreases or disappears, or transcription of these genes decreases or disappears. Such a mutant strain or gene recombinant strain can be obtained in the same manner as the mutant strain or gene recombinant strain described above in which purR gene does not function normally. The sequence of the add gene is known and, based on the sequence, the add gene can be readily obtained by PCR or hybridization. An example of the add gene from *E. coli* includes a gene encoding the amino acid sequence of SEQ ID NO: 38.

Also, the add gene from other microorganisms can be obtained based on the known sequence, or sequence homology with the above-mentioned add gene from *E. coli*, and this gene can be used for modification of microorganisms.

The add gene can include an amino acid sequence having an identity of not less than 70%, or in other examples, not less than 80%, not less than 90%, or even not less than 95% to the amino acid sequence of SEQ ID NO: 38.

The sequence of the purA gene is known, and based on this sequence, the purA gene can be readily obtained by PCR or hybridization. An example of the purA gene from *E. coli* includes a gene encoding the amino acid sequence of SEQ ID NO: 34. Also, the purA gene from other microorganisms can be obtained based on the known sequence, or sequence homology with the above-mentioned purA gene from *E. coli*, and this gene can be used for modification of microorganisms.

The purA gene can include an amino acid sequence having an identity of not less than 70%, or in other examples, not less than 80%, not less than 90%, or even not less than 95% to the amino acid sequence of SEQ ID NO: 34.

The microorganism can also be modified so that the nagD gene does not function normally. A mutant strain or gene recombinant strain of the nagD gene can be obtained by modifying the gene such that the activity of the protein encoded by the gene decreases or disappears, or transcription of the gene decreases or disappears. Such a mutant strain or gene recombinant strain can be obtained in the same manner as the mutant strain or gene recombinant strain described above in which the purR gene does not function normally.

The sequence of the nagD gene is known, and based on this sequence, the nagD gene can be readily obtained by PCR or hybridization. An example of the nagD gene from *E. coli* includes a gene encoding the amino acid sequence of SEQ ID NO: 42.

It is known that the nagD gene from *E. coli* is present in the nagBACD operon, which is involved in metabolizing N-acetylglucosamine. Expression of this nagBACD operon gene is induced by adding N-acetylglucosamine, which is one of the sugars which is a major ingredient of the bacterial cell walls, to a medium (Plumbridge J A., Mol. Micobiol. (1989) 3. 505-515). From the conserved structural characteristics, the NagD protein encoded by nagD from *E. coli* is known to belong to the family of haloacid dehalogenases (HAD). It has been reported that, according to in vitro experiments, the protein has a nucleotidase activity for GMP and 5'-uridylic acid (uridine 5'-monophosphate, hereinafter also referred to as "UMP") (Tremblay L W., Biochemistry, (2006) 45. 1183-1193). There are 23 types of HAD family proteins on *E. coli* genome and the range of their substrate specificity is extremely broad (Kuznetsova et al., J. Biol. Chem., (2006)

281, 36149-36161). Therefore, the physiological role of the nagD gene in cells is not known.

Inactivation of the nagD gene in a microorganism that has been modified so that expression of the guaB and guaA genes is increased, and the ushA and aphA genes are inactivated, resulted in efficient production of 5'-guanylic acid from inosinic acid.

Hence, a novel microorganism is described which is able to convert inosinic acid to 5'-guanylic acid. This microorganism has been modified so that inosinic acid dehydrogenase activity and 5'-guanylic acid synthetase activity are enhanced by increasing expression of the guaB and guaA genes, as well as decreasing activity or even inactivating the ushA, aphA and nagD genes. In addition, one or more of the purR gene, add gene, and purA gene can be further modified so the activity of their encoded proteins is decreased, or is completely inactivated.

The nagD gene is not limited to the gene from *E. coli*, and the nagD gene from other microorganisms can be obtained based on the known sequence, or sequence homology with the above-mentioned nagD gene from *E. coli*, and this gene can be used for the modification. Thus, the nagD gene can include a gene which encodes an amino acid sequence having an identity of not less than 70%, or in other examples, less than 80%, not less than 90%, or even not less than 95% to the amino acid sequence of SEQ ID NO: 42.

<II> Method for Producing GMP

GMP can be obtained by reacting IMP with the above-mentioned microorganism which has been modified so that IMP dehydrogenase activity and GMP synthetase activity are enhanced to convert IMP to GMP.

The reaction of IMP dehydrogenase or GMP synthetase requires $NAD^+$ or ATP, respectively. NADH generated by the reaction of IMP dehydrogenase is again converted to $NAD^+$ via an oxidative phosphorylated pathway. At that time, ATP is generated. Therefore, by simultaneously enhancing the activities of IMP dehydrogenase and GMP synthetase, the reaction from IMP to GMP can proceed efficiently.

The term "reacting" can include converting IMP to GMP by placing the above-mentioned microorganism in a medium to which IMP has been added, and by using the microorganism as the so-called microorganism enzyme. In this way, GMP is generated by adding IMP to the medium in which the above-mentioned microorganism is being cultured.

By adding the cells of the above-mentioned microorganism after culturing to a reaction solution containing IMP, or by adding IMP to a solution containing the above-mentioned microorganism, IMP can be efficiently converted to GMP, and GMP is produced and accumulates in the solution.

As a carbon source for culturing the microorganism, carbohydrates such as glucose, fructose, sucrose, molasses, blackstrap molasses or starch hydrolysate; alcohols such as ethanol, glycerin or sorbitol; organic acids such as pyruvic acid, lactic acid or acetic acid; amino acids such as glycine, alanine, glutamic acid or aspartic acid can be used, as long as the source can be assimilated by the above-mentioned microorganism. As a nitrogen source, various inorganic and organic ammonium salts such as ammonia, ammonia chloride, ammonium sulfate, ammonium nitrate, ammonium carbonate, ammonium acetate or ammonium phosphate; urea, various amino acids, peptone, NZ amine, meat extract, yeast extract, corn steep liquor, casein hydrolysate, fish meal, digested material thereof or the like can be used. As an inorganic substance, potassium dihydrogen phosphate, potassium monophosphate, magnesium sulfate, magnesium phosphate, sodium chloride, ferrous sulfate, manganese sulfate, zinc sulfate, calcium carbonate or the like can be used. In cases where the microorganism requires specific trophic substances such as amino acids, nucleic acids or vitamins for its growth, an appropriate amount of these substances can be added to the medium. The culture can be carried out in an appropriate range of pH 5.0 to 8.5, and 15° C. to 45° C. under aerobic conditions for about 5 hours to 72 hours. In addition, to adjust the pH, an inorganic or organic, acidic or alkaline substance, as well as ammonia gas, or the like can be used.

The conversion from IMP to GMP can be carried out by directly injecting the culture solution of the microorganism, by injecting only microbial cells after centrifugation of the culture solution, or by injecting a suspension containing the bacterial cells in an appropriate solution into the reaction solution containing IMP. In the method for producing GMP, a processed product of the above-mentioned microbial cells can also be used. Examples of the processed product of microbial cells include immobilized microbial cells in which the microbial cells are immobilized using acrylamide, carrageenan, or the like.

As the carbon source for the reaction solution, carbohydrates such as glucose, fructose, sucrose, molasses, blackstrap molasses or starch hydrolysate; alcohols such as ethanol, glycerin or sorbitol; organic acids such as pyruvic acid, lactic acid or acetic acid; amino acids such as glycine, alanine, glutamic acid or aspartic acid can be used, as long as it can be assimilated by the above-mentioned microorganisms. As a nitrogen source, various inorganic and organic ammonium salts such as ammonia, ammonia chloride, ammonium sulfate, ammonium nitrate, ammonium carbonate, ammonium acetate or ammonium phosphate; urea, various amino acids, peptone, NZ amine, meat extract, yeast extract, corn steep liquor, casein hydrolysate, fish meal, digested material thereof or the like can be used. As an inorganic substance, potassium dihydrogen phosphate, potassium monophosphate, magnesium sulfate, magnesium phosphate, sodium chloride, ferrous sulfate, manganese sulfate, zinc sulfate, calcium carbonate or the like can be used. In cases where the chosen microorganism requires specific trophic substances such as amino acids, nucleic acids or vitamins for its growth, an appropriate amount of these substances is added to the medium.

Furthermore, the permeability of nucleotides to the cells can be activated by adding an organic solvent to the reaction solution.

As the organic solvent which acts to activate membrane permeability for the nucleotides, xylene, toluene, benzene, fatty acid alcohol, ethyl acetate, or the like can be used. The concentration thereof can be 0.1 to 30 ml/L. The reaction can be carried out in an appropriate range of pH 5.0 to 8.5 and 15° C. to 45° C. under aerobic or anaerobic condition for about 1 hour to 7 days. In addition, to adjust the pH, an inorganic or organic, acidic or alkaline substance, as well as ammonia gas or the like can be used. IMP can be chemically synthesized or produced by a fermentation method (WO96/30501, Japanese Patent Application Laid-Open Publication No. 2002-355087, Japanese Patent Application Laid-Open Publication No. 2003-325182 or the like), or the like. IMP is also commercially available.

GMP can be collected from the reaction solution by a known method, including using anion exchange resin method, a precipitation method and other known methods.

EXAMPLES

The present invention will now be described more concretely by way of the following non-limiting examples.

Example 1

<1-1> Construction of a JM109 Strain Where 5'-nucleotidase Encoding ushA and aphA Genes are Deleted The *Escherichia coli* JM109 strain, which is commonly used as a host for DNA cloning, was used to construct a strain which does not produce 5'-nucleotidase. 5'-nucleotidase is encoded by the ushA gene (Genbank Accession X03895 SEQ ID NO: 21) and aphA gene (Genbank Accession X86971 SEQ ID NO: 23).

Deletion of the ushA and aphA genes encoding 5'-nucleotidase was carried out by a method called "Red-driven integration" which was originally developed by Datsenko and Wanner (Proc. Natl. Acad. Sci. USA, 2000, vol. 97, No. 12, p 6640-6645) and an excision system derived from λ phage (J. Bacteriol. 2002 September; 184(18): 5200-3. Interactions between integrase and excisionase in the phage lambda excisive nucleoprotein complex. Cho E H, Gumport R I, Gardner J F.). According to the "Red-driven integration" method, a gene-disrupted strain can be constructed in one step by using a PCR product which was obtained by using, as primers, synthetic oligonucleotides designed to have part of the desired gene in the 5'end and part of an antibiotic resistance gene in the 3' end. Furthermore, by combining with the excision system derived from λ phage, the antibiotic resistance gene incorporated in the gene disrupted strain can be removed.

(1) Disruption of ushA Gene

As the template for PCR, the plasmid pMW118-attL-Cm-attR was used. pMW118-attL-Cm-attR (WO2006078039) has attachment sites for λ phage, the attL and attR genes, as well as the cat gene, which is an antibiotic resistance gene, by insertion of these sites and genes in pMW118 (manufactured by Takara Bio Inc.) in the order of attL-cat-attR.

PCR was carried out using, as primers, synthetic oligonucleotides (SEQ ID NOs: 25 and 26) having a sequence corresponding to both ends of attL and attR in the 3' end of the primer and a sequence corresponding to part of the desired gene, ushA, in the 5' end of the primer.

The amplified PCR product was purified on an agarose gel and introduced into the *Escherichia coli* JM109 strain containing a plasmid pKD46 having a temperature-sensitive replication ability by electroporation. The plasmid pKD46 (Proc. Natl. Acad. Sci. USA, 2000, vol. 97, No. 12, p 6640-6645) contains a DNA fragment with a total of 2154 nucleotides of the λ phage (GenBank/EMBL Accession number J02459, the 31088th nucleotide to the 33241st nucleotide) containing a gene encoding Red recombinase (γ, β and exo genes) of a λ Red homologous recombination system controlled by a arabinose-inducible $P_{araB}$ promoter. The plasmid pKD46 is required to incorporate the PCR product into the chromosome of JM109 strain.

Competent cells for electroporation were prepared as follows. That is, *Escherichia coli* JM109 strain cultured in LB medium containing 100 mg/L of ampicillin at 30° C. overnight was 100-fold diluted with 5 mL of SOB medium containing ampicillin (20 mg/L) and L-arabinose (1 mM) (Molecular Cloning: Laboratory Manual, Second Edition, Sambrook, J. et al., Cold Spring Harbor Laboratory Press (1989)). The obtained diluted cells were, while aerated, grown at 30° C. until OD600 reached about 0.6. Thereafter, cells were concentrated 100-fold and washed three times with 10% glycerol so as to be used for electroporation. The electroporation was carried out using 70 μL of the obtained competent cells and about 100 ng of the PCR product. After the electroporation, 1 mL of SOC medium (Molecular Cloning: Laboratory Manual, Second Edition, Sambrook, J. et al., Cold Spring Harbor Laboratory Press (1989)) was added to the cells and cultured at 37° C. for 2.5 hours, followed by plate culture on L-agar medium containing Cm (Chloramphenicol) (25 mg/L) at 37° C. to select Cm-resistant recombinants. Subsequently, in order to remove the pKD46 plasmid, the cells were subcultured twice on L-agar medium containing Cm at 42° C. and ampicillin resistance of the obtained colonies was examined to obtain an ampicillin-sensitive strain in which pKD46 had been deleted.

The deletion of the ushA gene in the mutant which could be distinguished by a chloramphenicol resistant gene was confirmed by PCR. The obtained ushA-deleted strain was named JM109ΔushA::att-cat Next, in order to remove the att-cat gene which had been introduced into the ushA gene, the above-described pMW-intxis-ts was used as a helper plasmid. pMW-intxis-ts carries a gene encoding integrase (Int) of the λ phage and a gene encoding excisionase (Xis), as well as having a temperature-sensitive replication ability. By the introduction of pMW-intxis-ts, attL or attR on the chromosome is recognized, recombination take place, and the gene between attL and attR is cut out, resulting in a structure in which only the attL or attR sequence remains on the chromosome.

Competent cells of JM109ΔushA::att-cat strain obtained above were prepared in accordance with a conventional method, transformed with the helper plasmid pMW-intxis-ts, and subjected to plate culture on L-agar medium containing 50 mg/L of ampicillin at 30° C. to select an ampicillin resistant strain. Next, in order to remove pMW-intxis-ts plasmid, subculture was carried out twice on L-agar medium at 42° C., ampicillin and chloramphenicol resistance of the obtained colony was examined to obtain a chloramphenicol- and ampicillin-sensitive strain where ushA is disrupted and att-cat and pMW-intxis-ts were cured. This strain was named JM109ΔushA.

(2) Deletion of aphA Gene of JM109ΔushA Strain

Deletion of the aphA gene in the JM109ΔushA strain was carried out according to the above method and using SEQ ID NOs: 27 and 28 as primers for aphA disruption. Thereby, JM109ΔushAΔaphA, in which the ushA and aphA were disrupted, was obtained.

<1-2> Construction of purR Gene (a Gene Encoding Repressor of Purine Operon and guaBA Operon) Disrupted Strain from the JM109ΔushAΔaphA Strain Subsequently, using the JM109ΔushAΔaphA strain as a parent strain, a strain that does not produce a repressor of guaBA operon, PurR, was constructed. PurR is encoded by the purR gene (Genbank Accession J04212, SEQ ID NO: 17). The construction was carried out according to the above-described method of disruption of ushA and aphA genes and using the primers of SEQ ID NOs: 29 and 30 for the purR disruption. Thereby, JM109ΔushAΔaphAΔpurR was obtained.

<1-3> Construction of the Plasmid pUC18-guaBA for Expression of IMP dehydrogenase and GMP Synthetase and Introduction of the Plasmid into the JM109ΔushAΔaphAΔpurR Strain The plasmid pUC18-guaBA for expression of IMP dehydrogenase and GMP synthetase was constructed as follows. It is known that the guaB and guaA genes that encode these enzymes constitute an operon (guaBA) in *Escherichia coli*. Thus, PCR was carried out using primers of SEQ ID NO: 31 and SEQ ID NO: 32 to amplify the guaBA operon of *Escherichia coli*. After the amplified fragment was purified, restriction sites formed at both ends were cleaved with SacI and KpnI. The cleaved fragment was ligated with pUC18 which was also cleaved with SacI and KpnI to obtain a plasmid pUC18-guaBA in which the guaBA gene is inserted. This plasmid was introduced into the above-mentioned JM109ΔushAΔaphAΔpurR strain to obtain the JM109ΔushAΔaphAΔpurR/pUC18-guaBA strain.

<1-4> Conversion from IMP to GMP using the JM109ΔushAΔaphAΔpurR/pUC18-guaBA Strain For the above-mentioned bacterial cells, the conversion reaction from IMP to GMP was evaluated. Hereinafter, the method for preparing the bacterial cells, the reaction method, composition of the reaction solution, and analytic method for the evaluation of the conversion reaction from IMP to GMP are described.

Method for Preparing Bacterial Cells:

The JM109ΔushAΔaphAΔpurR/pUC18-guaBA strain was evenly spread on an LB medium plate and cultured at 37° C. overnight. Next day, bacterial cells corresponding to 1/32 of the plate were seeded in a 500-ml Sakaguchi flask containing 20 ml of LB medium and cultured at 37° C. overnight. Bacterial cells obtained by centrifuging the culture solution of LB (600 ml) were used for a 60 ml of a reaction solution.

Method for Reaction:

The above-described bacterial cells from 600 ml of LB after culturing were scraped with a medicine spoon and thereafter seeded in 60 ml of the reaction solution described later to initiate a reaction. The reaction was carried out at 42° C. while the pH was maintained at 7.2 by adding sodium hydroxide.

Composition of Reaction Solution:
60 mM IMP
50 g/L Glucose
9.2 g/L Sodium hexametaphosphate
5 g/L $MgSO_4.7H_2O$
6.6 g/L $(NH_4)_2SO_4$
10 g/L $KH_2PO_4$
5 ml/L Xylene Method of Analysis:

The reaction solution (500 μl) was sampled over time and centrifuged at 15,000 rpm for 5 minutes. The supernatant was diluted with NaOH to terminate the reaction. The resulting solution was filtered and 300 μl of the filtrate was subjected to HPLC analysis. Conditions of the analysis are as follows:

Column: Two of Asahipak GS-220 (diameter 7.6 mm, 50 cm) were connected.
Eluent: 0.2 M $NaH_2PO_4$ (pH 3.98)
Temperature: 55° C.
Flow rate: 1 ml/min
Detection: Ultraviolet (254 nm) absorption The results are shown in FIG. 1. It was shown that JM109ΔushAΔaphAΔpurR/pUC18-guaBA produced a maximum of about 16.2 g/L of GMP in the reaction solution after 12 hours of the reaction.

Example 2

<2-1> Construction of a nagD Gene Disrupted Strain from the JM109ΔushAΔaphAΔpurR Strain Using the JM109ΔushAΔaphAΔpurR strain, which was obtained in Example 1 <1-2> as a parent strain, a strain which does not produce NagD was constructed. NagD is encoded by the nagD gene (Genbank Accession X14135, SEQ ID NO: 41). The nagD gene was disrupted according to the above-described method of disruption of ushA, aphA and purR genes and using primers of SEQ ID NOs: 43 and 44 for nagD disruption. Thereby, JM109ΔushAΔaphAΔpurRΔnagD was obtained.

<2-2> Introduction of the Plasmid pUC18-guaBA for Expression of IMP dehydrogenase and GMP Synthetase into the JM109ΔushAΔaphAΔpurR and JM109ΔushAΔaphAΔpurRΔnagD Strains The plasmid pUC18-guaBA was introduced into the above-mentioned JM109ΔushAΔaphAΔpurR and JM109ΔushAΔaphAΔpurRΔnagD strains to obtain the JM109ΔushAΔaphAΔpurR/pUC18-guaBA and JM109ΔushAΔaphAΔpurRΔnagD/pUC18-guaBA strains, respectively.

<2-3> Conversion from IMP to GMP using the JM109ΔushAΔaphAΔpurR/pUC18-guaBA and JM109ΔushAΔaphAΔpurRΔnagD/pUC18-guaBA Strains For the above-mentioned bacterial cells, the conversion reaction from IMP to GMP was evaluated. Hereinafter, a method for preparing bacterial cells, a method for reaction, composition of a reaction solution and a method of analysis for the conversion reaction from IMP to GMP are described.

Method for Preparing Bacterial Cells:

The JM109ΔushAΔaphAΔpurR/pUC18-guaBA strain or JM109ΔushAΔaphAΔpurRΔnagD/pUC18-guaBA strain was evenly spread on an LB medium plate and cultured at 37° C. overnight. Next day, bacterial cells corresponding to 1/32 of the plate were seeded in a 500-ml Sakaguchi flask containing 20 ml of LB medium and cultured at 37° C. overnight Method for Reaction:

The above-described culture solution was centrifuged and bacterial cells corresponding to a thy weight of 0.8 g were seeded in 60 ml of a reaction solution to initiate the reaction. The reaction was carried out at 42° C. while pH was maintained at 7.2 by adding sodium hydroxide.

Composition of Reaction Solution for Conversion Reaction from IMP to GMP:
50 mM IMP
50 g/L Glucose
9.2 g/L Sodium hexametaphosphate
5 g/L $MgSO_4.7H_2O$
6.6 g/L $(NH_4)_2SO_4$
10 g/L $KH_2PO_4$
3 ml/L Xylene Method of Analysis:

The reaction solution (500 μl) was sampled with time and diluted with NaOH to terminate the reaction. The resulting solution was filtered and 300 μl of the filtrate was subjected to HPLC analysis.

Figure 2:
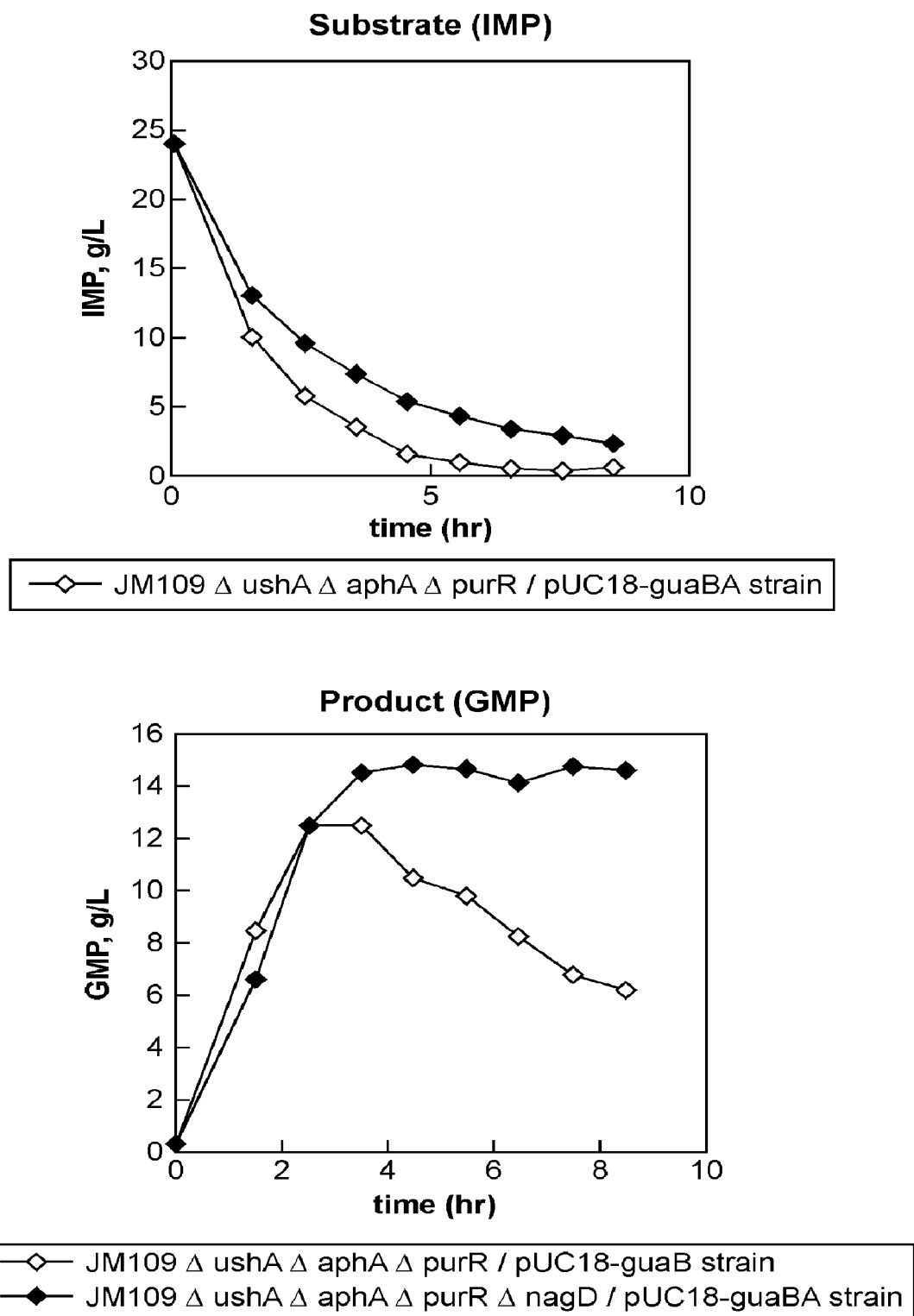
FIG. 2 is a graph showing the change in the concentration of IMP (A) and GMP (B) when the JM109ΔushAΔaphAΔpurR/pUC18-guaBA strain and the JM109ΔushAΔaphAΔpurRΔnagD/pUC18-guaBA strain were reacted with IMP.

Conditions of the Analysis are as Follows:

Column: Two of Asahipak GS-220 (diameter 7.6 mm, 50 cm) were connected.
Eluent: 0.2 M $NaH_2PO_4$ (pH 3.98)
Temperature: 55° C.
Flow rate: 1 ml/min
Detection: Ultraviolet (254 nm) absorption The results are shown in FIG. 2. It was shown that the JM109ΔushAΔaphAΔpurR/pUC18-guaBA strain produced a maximum of about 12.5 g/L of GMP in the reaction solution whereas the JM109ΔushAΔaphAΔpurRΔnagD/pUC18-guaBA strain produced a maximum of about 14.81 g/L of GMP.

Example 3

Conversion from IMP to GMP and from XMP to GMP using the JM109ΔushAΔaphAΔpurRΔnagD/pUC18-guaBA Strain Described in Example 2 and Comparison Thereof For the JM109ΔushAΔaphAΔpurRΔnagD/pUC18-guaBA strain described in Example 2, the conversion reaction from IMP to GMP and conversion reaction from XMP to GMP were evaluated. The method for preparing bacterial cells, method for reaction, composition of a solution for a conversion reaction from IMP to GMP and method of analysis for the evaluation of the conversion reaction were employed in accordance with Example 2. In the conversion reaction from XMP to GMP, the same concentration of XMP, instead of IMP in the solution for the conversion reaction from IMP to GMP, was used.

Figure 3A:
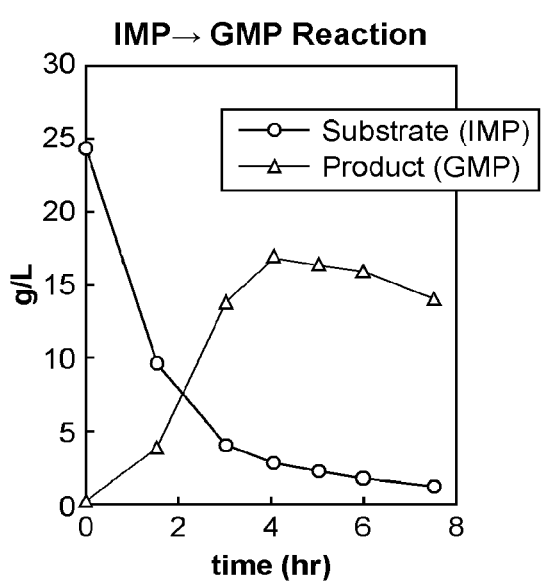
FIG. 3A shows a graph showing the change in the concentration of IMP and GMP when the JM109ΔushAΔaphAΔpurRΔnagD/pUC18-guaBA strain was reacted with IMP.
Figure 3B:
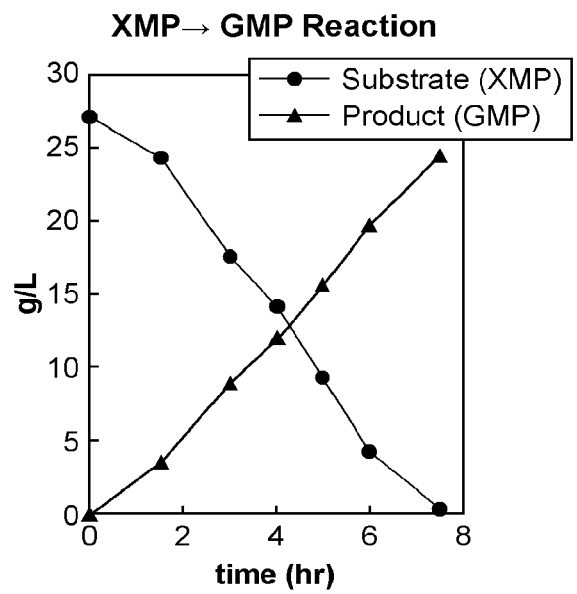
FIG. 3B shows a graph showing the change in the concentration of XMP and GMP when the JM109ΔushAΔaphAΔpurRΔnagD/pUC18-guaBA strain was reacted with XMP.
Figure 3C:
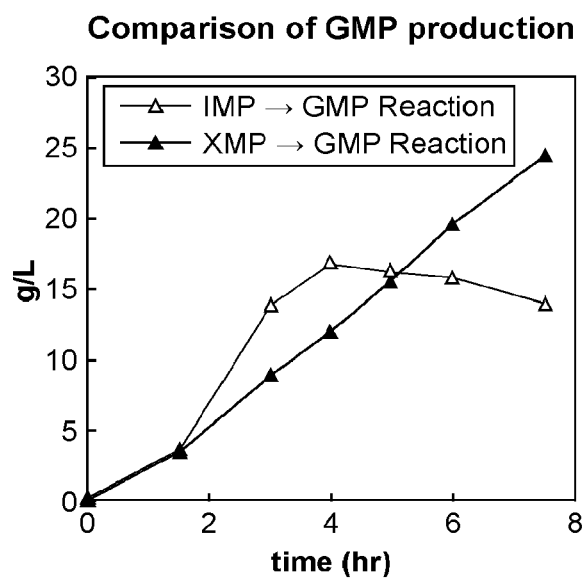
FIG. 3C shows a graph showing the accumulated amount of GMP when the JM109ΔushAΔaphAΔpurRΔnagD/pUC18-guaBA strain was reacted with IMP or XMP.

The results are shown in FIG. 3. It was shown that up to about 16.9 g/L of GMP was produced in the reaction solution by 4 hours of the reaction in the conversion from IMP to GMP whereas a maximum of about 24.4 g/L of GMP was produced in the reaction solution by 7.5 hours of the reaction in the conversion from XMP to GMP, and thus the production rate of GMP in the reaction with IMP as a substrate is higher than that in the reaction with XMP as the substrate.

Example 4

<4-1> Construction of 5'-nucleotidase Encoding ushA and aphA Disrupted Strain from the MG1655 Strain Using *Escherichia coli* wild type MG1655 strain as a parent strain, a strain which does not produce 5'-nucleotidase, UshA and AphA was constructed. The ushA and aphA genes encoding 5'-nucleotidase were deleted by a method called "Red-driven integration" and an excision system derived from λ phage in accordance with Example 1. The produced strain was named MG1655ΔushAΔaphA.

<4-2> Construction of succinyl AMP Synthase Encoding purA Gene Disrupted Strain from MG1655ΔushAΔaphA Strain Subsequently, using the MG1655ΔushAΔaphA strain as a parent strain, a strain which does not produce succinyl AMP synthase was constructed. Succinyl AMP synthase of *E. coli* is encoded by the purA gene (Genbank Accession J04199, SEQ ID NO: 33). The construction was carried out according to the method of disruption of ushA, aphA and purR genes shown in Example 1 and using primers of SEQ ID NOs: 35 and 36 for purA disruption. Thereby, MG1655ΔushAΔaphAΔpurA was obtained.

<4-3> Construction of the purR Gene (a Gene Encoding Repressor of Purine Operon and guaBA Operon) Disrupted Strain from the MG1655ΔushAΔaphAΔpurA Strain Subsequently, using the MG1655ΔushAΔaphAΔpurA strain as a parent strain, a strain which does not produce a repressor of the guaBA operon, PurR was constructed. The purR gene was disrupted in accordance with Example 1 and using primers of SEQ ID NOs: 29 and 30 for purR disruption. Thereby, MG1655ΔushAΔaphAΔpurAΔpurR was obtained.

<4-4> Construction of adenosine deaminase Encoding Add Gene Disrupted Strain from MG1655ΔushAΔaphAΔpurR Strain Subsequently, using the MG1655ΔushAΔaphAΔpurAΔpurR strain as a parent strain, a strain that does not produce adenosine deaminase was constructed. Adenosine deaminase of *E. coli* is encoded by the add gene (Genbank Accession No. M59033, SEQ ID NO: 37). The construction was carried out according to the method of disruption of ushA, aphA and purR genes shown in Example 1 and using primers of SEQ ID NOs: 39 and 40 for add disruption. Thereby, MG1655ΔushAΔaphAΔpurAΔpurRΔadd strain was obtained.

<4-5> Introduction of the Plasmid pUC18-guaBA for Expression of IMP dehydrogenase and GMP Synthetase into the MG1655ΔushAΔaphAΔpurAΔpurRΔadd Strain pUC18-guaBA shown in Example 1 was introduced into the above-mentioned MG1655ΔushAΔaphAΔpurAΔpurRΔadd strain to obtain the MG1655ΔushAΔaphAΔpurAΔpurRΔadd/pUC18-guaBA strain.

<4-6> Conversion from IMP or XMP to GMP using the MG1655ΔushAΔaphAΔpurAΔpurRΔadd/pUC18-guaBA Strain As for the above-mentioned bacterial cells, the conversion reaction from IMP or XMP to GMP was evaluated. Hereinafter, the method for preparing bacterial cells, method for reaction, composition of a reaction solution and method of analysis for the evaluation of the conversion reaction are described.

Method for Preparing Bacterial Cells:

The MG1655ΔushAΔaphAΔpurAΔpurRΔadd/pUC18-guaBA strain was evenly spread on an LB medium plate and cultured at 37° C. overnight Next day, bacterial cells corresponding to ⅟₃₂ of the plate were seeded in a 500-ml Sakaguchi flask containing 20 ml of LB medium and cultured at 37° C. overnight Bacterial cells obtained by centrifuging the culture solution of LB (600 ml) were used for a 60 ml of a reaction solution.

Method for Reaction:

The above-described bacterial cells from 600 ml of LB after culturing were scraped with a medicine spoon and thereafter seeded in 60 ml of the reaction solution described later to initiate a reaction, The reaction was carried out at 42° C. while pH was maintained at 7.2 by adding sodium hydroxide.

Composition of Reaction Solution:

50 mM IMP or 50 mM XMP
50 g/L Glucose
9.2 g/L Sodium hexametaphosphate
5 g/L MgSO$_4$.7H$_2$O
6.6 g/L (NH$_4$)$_2$SO$_4$
10 g/L KH$_2$PO$_4$
5 ml/L Xylene Method of Analysis:

The reaction solution (500 μk) was sampled with time and diluted with NaOH to terminate the reaction. The resulting solution was filtered and 300 μl of the filtrate was subjected to HPLC analysis.

Conditions of the Analysis are as Follows:

Column: Two of Asahipak GS-220 (diameter 7.6 mm, 50 cm) were connected.

Eluent: 0.2 M $NaH_2PO_4$ (pH 3.98)

Temperature: 55° C.

Flow rate: 1 ml/min

Detection: Ultraviolet (254 nm) absorption

Figure 4A:
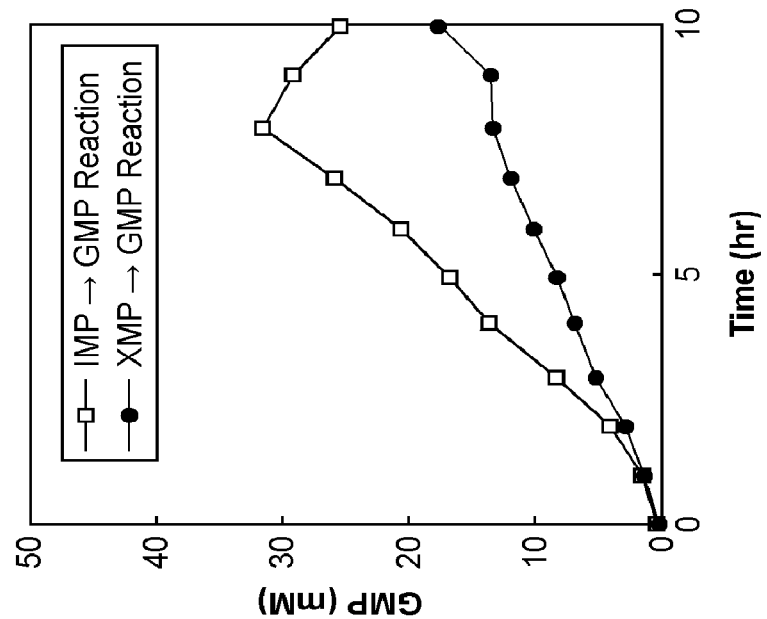
FIG. 4A shows a graph showing the change in the concentration of IMP, XMP and GMP when the MG1655ΔushAΔaphAΔpurAΔpurRΔadd/pUC18-guaBA strain was reacted with IMP.
Figure 4B:
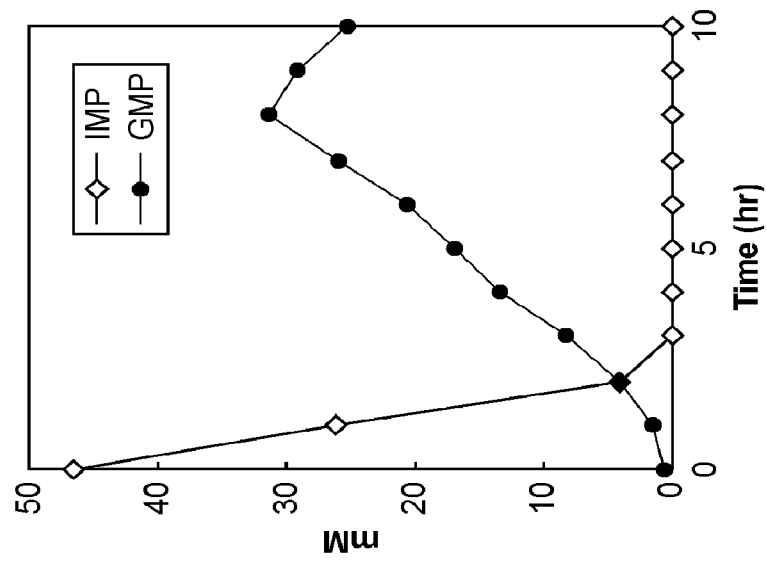
FIG. 4B shows a graph showing the amount of GMP produced when the MG1655ΔushAΔaphAΔpurAΔpurRΔadd/pUC18-guaBA strain was reacted with IMP or XMP.

The results are shown in FIG. 4. It was shown that the production rate of GMP in the reaction with IMP as a substrate is higher than that in the reaction with XMP as the substrate.

INDUSTRIAL APPLICABILITY

According to the present invention, GMP which is useful as a seasoning, in pharmaceuticals and for raw materials thereof can be efficiently produced.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

Explanation of the Sequence Listing:

SEQ ID NO: 1: Nucleotide sequence of *E. coli* GMP synthetase (GMPS) gene (guaA)

SEQ ID NO: 2: Amino acid sequence of *E. coli* GMPS

SEQ ID NO: 3: Nucleotide sequence of *B. subtilis* GMPS gene (guaA)

SEQ ID NO: 4: Amino acid sequence of *B. subtilis* GMPS

SEQ ID NO: 5: Nucleotide sequence of *C. glutamicum* GMPS gene (guaA)

SEQ ID NO: 6: Amino acid sequence of *C. glutamicum* GMPS

SEQ ID NO: 7: Nucleotide sequence of *C. ammoniagenes* GMPS gene (guaA)

SEQ ID NO: 8: Amino acid sequence of *C. ammoniagenes* GMPS

SEQ ID NO: 9: Nucleotide sequence of *E. coli* IMP dehydrogenase (IMPDH) gene (guaB)

SEQ ID NO: 10: Amino acid sequence of *E. coli* IMPDH

SEQ ID NO: 11: Nucleotide sequence of *B. subtilis* IMPDH gene (guaB)

SEQ ID NO: 12: Amino acid sequence of *B. subtilis* IMPDH

SEQ ID NO: 13: Nucleotide sequence of *C. glutamicum* IMPDH gene (guaB)

SEQ ID NO: 14: Amino acid sequence of *C. glutamicum* IMPDH

SEQ ID NO: 15: Nucleotide sequence of *C. ammoniagenes* IMPDH gene (guaB)

SEQ ID NO: 16: Amino acid sequence of *C. ammoniagenes* IMPDH

SEQ ID NO: 17: Nucleotide sequence of *E. coli* purr

SEQ ID NO: 18: Amino acid sequence of *E. coli* PurR

SEQ ID NO: 19: Primer sequence for cloning of *E. coli* purr

SEQ ID NO: 20: Primer sequence for cloning of *E. coli* purr

SEQ ID NO: 21: Nucleotide sequence of *E. coli* ushA

SEQ ID NO: 22: Amino acid sequence of *E. coli* UshA

SEQ ID NO: 23: Nucleotide sequence of *E. coli* aphA

SEQ ID NO: 24: Amino acid sequence of *E. coli* AphA

SEQ ID NO: 25: Primer sequence for disruption of *E. coli* ushA gene

SEQ ID NO: 26: Primer sequence for disruption of *E. coli* ushA gene

SEQ ID NO: 27: Primer sequence for disruption of *E. coli* aphA gene

SEQ ID NO: 28: Primer sequence for disruption of *E. coli* aphA gene

SEQ ID NO: 29: Primer sequence for disruption of *E. coli* purR gene

SEQ ID NO: 30: Primer sequence for disruption of *E. coli* purR gene

SEQ ID NO: 31: Primer sequence for cloning of *E. coli* guaBA

SEQ ID NO: 32: Primer sequence for cloning of *E. coli* guaBA

SEQ ID NO: 33: Nucleotide sequence of *E. coli* purA

SEQ ID NO: 34: Amino acid sequence of *E. coli* PurA

SEQ ID NO: 35: Primer sequence for disruption of *E. coli* purA gene

SEQ ID NO: 36: Primer sequence for disruption of *E. coli* purA gene

SEQ ID NO: 37: Nucleotide sequence of *E. coli* add

SEQ ID NO: 38: Amino acid sequence of *E. coli* Add

SEQ ID NO: 39: Primer sequence for disruption of *E. coli* add gene

SEQ ID NO: 40: Primer sequence for disruption of *E. coli* add gene

SEQ ID NO: 41: Nucleotide sequence of *E. coli* nagD

SEQ ID NO: 42: Amino acid sequence of *E. coli* NagD

SEQ ID NO: 43: Primer sequence for disruption of *E. coli* nagD gene

SEQ ID NO: 44: Primer sequence for disruption of *E. coli* nagD gene

The invention claimed is:

1. A method for producing 5'-guanylic acid comprising:
  A) reacting inosinic acid with a microorganism which is able to convert inosinic acid into 5'-guanylic acid in a reaction solution comprising an organic solvent, wherein permeability of said microorganism's cells to nucleotide is activated by the presence of an organic solvent; and
  B) collecting 5'-guanylic acid;
wherein said microorganism has been modified so that inosinic acid dehydrogenase activity and 5'-guanylic acid synthetase activity are enhanced by increasing expression of a guaB gene and guaA gene,
wherein said guaA gene encodes a protein selected from the group consisting of:
  (A) a protein comprising the amino acid sequence of SEQ ID NO: 2, and
  (B) a protein comprising an amino acid sequence which has a sequence identity of not less than 95% to that of SEQ ID NO: 2, and has 5' guanylic acid synthetase activity,
wherein said guaB gene encodes a protein selected from the group consisting of:
  (C) a protein comprising the amino acid sequence of SEQ ID NO: 10, and
  (D) a protein comprising an amino acid sequence which has a sequence identity of not less than 95% to that of SEQ ID NO: 10, and has inosinic acid dehydrogenase activity, and
wherein said microorganism is selected from the group consisting of *Escherichia* bacteria, *Bacillus* bacteria and coryneform bacteria.

2. The method according to claim 1, wherein said microorganism has been further modified so that a gene selected from the group consisting of ushA, aphA, and combinations thereof do not function normally.

3. The method according to claim 1, wherein said microorganism has been further modified so that a gene selected from the group consisting of purR, add, purA, and combinations thereof do not function normally.

4. The method according to claim 1, wherein said microorganism has been further modified so that a nagD gene does not function normally.

5. The method according to claim 1, wherein said microorganism is an *Escherichia* bacterium.

6. The method according to claim 5, wherein said microorganism is *Escherichia coli*.

* * * * *

SEQUENCE LISTING

```
<160> NUMBER OF SEQ ID NOS: 44

<210> SEQ ID NO 1
<211> LENGTH: 1578
<212> TYPE: DNA
<213> ORGANISM: Escherichia coli
<220> FEATURE:
<221> NAME/KEY: CDS
<222> LOCATION: (1)..(1575)

<400> SEQUENCE: 1 atg acg gaa aac att cat aag cat cgc atc ctc att ctg gac ttc ggt      48
Met Thr Glu Asn Ile His Lys His Arg Ile Leu Ile Leu Asp Phe Gly
```

-continued

```
1               5                   10                  15
tct cag tac act caa ctg gtt gcg cgc cgc gtg cgt gag ctg ggt gtt        96
Ser Gln Tyr Thr Gln Leu Val Ala Arg Arg Val Arg Glu Leu Gly Val
             20                  25                  30 tac tgc gaa ctg tgg gcg tgg gat gtg aca gaa gca caa att cgt gac       144
Tyr Cys Glu Leu Trp Ala Trp Asp Val Thr Glu Ala Gln Ile Arg Asp
         35                  40                  45 ttc aat cca agc ggc att att ctt tcc ggc ggc ccg gaa agt act act       192
Phe Asn Pro Ser Gly Ile Ile Leu Ser Gly Gly Pro Glu Ser Thr Thr
     50                  55                  60 gaa gaa aac agt ccg cgt gcg ccg cag tat gtc ttt gaa gca ggc gta       240
Glu Glu Asn Ser Pro Arg Ala Pro Gln Tyr Val Phe Glu Ala Gly Val
65                  70                  75                  80 ccg gta ttc ggc gtt tgc tat ggc atg cag acc atg gca atg cag ttg       288
Pro Val Phe Gly Val Cys Tyr Gly Met Gln Thr Met Ala Met Gln Leu
                 85                  90                  95 ggc ggt cac gtt gaa gcc tct aac gaa cgt gaa ttt ggc tac gcg cag       336
Gly Gly His Val Glu Ala Ser Asn Glu Arg Glu Phe Gly Tyr Ala Gln
             100                 105                 110 gtt gaa gtc gta aac gac agc gca ctg gtt cgc ggt atc gaa gat gcg       384
Val Glu Val Val Asn Asp Ser Ala Leu Val Arg Gly Ile Glu Asp Ala
         115                 120                 125 ctg acc gca gac ggt aaa ccg ctg ctc gat gtc tgg atg agc cac ggc       432
Leu Thr Ala Asp Gly Lys Pro Leu Leu Asp Val Trp Met Ser His Gly
     130                 135                 140 gat aaa gtt acc gct att ccg tcc gac ttc atc acc gta gcc agc acc       480
Asp Lys Val Thr Ala Ile Pro Ser Asp Phe Ile Thr Val Ala Ser Thr
145                 150                 155                 160 gaa agc tgc ccg ttt gcc att atg gct aac gaa gaa aaa cgc ttc tat       528
Glu Ser Cys Pro Phe Ala Ile Met Ala Asn Glu Glu Lys Arg Phe Tyr
                 165                 170                 175 ggc gta cag ttc cac ccg gaa gtg act cat acc cgc cag ggt atg cgc       576
Gly Val Gln Phe His Pro Glu Val Thr His Thr Arg Gln Gly Met Arg
             180                 185                 190 atg ctg gag cgt ttt gtg cgt gat atc tgc cag tgt gaa gcc ctg tgg       624
Met Leu Glu Arg Phe Val Arg Asp Ile Cys Gln Cys Glu Ala Leu Trp
         195                 200                 205 acg cca gcg aaa att atc gac gat gct gta gct cgc atc cgc gag cag       672
Thr Pro Ala Lys Ile Ile Asp Asp Ala Val Ala Arg Ile Arg Glu Gln
     210                 215                 220 gta ggc gac gat aaa gtc atc ctc ggc ctc tct ggt ggt gtg gat tcc       720
Val Gly Asp Asp Lys Val Ile Leu Gly Leu Ser Gly Gly Val Asp Ser
225                 230                 235                 240 tcc gta acc gca atg ctg ctg cac cgc gct atc ggt aaa aac ctg act       768
Ser Val Thr Ala Met Leu Leu His Arg Ala Ile Gly Lys Asn Leu Thr
                 245                 250                 255 tgc gta ttc gtc gac aac ggc ctg ctg cgc ctc aac gaa gca gag cag       816
Cys Val Phe Val Asp Asn Gly Leu Leu Arg Leu Asn Glu Ala Glu Gln
             260                 265                 270 gtt ctg gat atg ttt ggc gat cac ttt ggt ctt aac att gtt cac gta       864
Val Leu Asp Met Phe Gly Asp His Phe Gly Leu Asn Ile Val His Val
         275                 280                 285 ccg gca gaa gat cgc ttc ctg tca gcg ctg gct ggc gaa aac gat ccg       912
Pro Ala Glu Asp Arg Phe Leu Ser Ala Leu Ala Gly Glu Asn Asp Pro
     290                 295                 300 gaa gca aaa cgt aaa atc atc ggt cgc gtt ttc gtt gaa gta ttc gat       960
Glu Ala Lys Arg Lys Ile Ile Gly Arg Val Phe Val Glu Val Phe Asp
305                 310                 315                 320 gaa gaa gcg ctg aaa ctg gaa gac gtg aag tgg ctg gcg cag ggc acc      1008
Glu Glu Ala Leu Lys Leu Glu Asp Val Lys Trp Leu Ala Gln Gly Thr
```

```
                     325                 330                 335
atc tac cct gac gtt atc gaa tct gcg gcg tct gca acc ggt aaa gca    1056
Ile Tyr Pro Asp Val Ile Glu Ser Ala Ala Ser Ala Thr Gly Lys Ala
             340                 345                 350 cac gtc atc aaa tct cac cac aac gtg ggc ggc ctg ccg aaa gag atg    1104
His Val Ile Lys Ser His His Asn Val Gly Gly Leu Pro Lys Glu Met
         355                 360                 365 aag atg ggc ctg gtt gaa ccg ctg aaa gag ctg ttc aaa gac gaa gtg    1152
Lys Met Gly Leu Val Glu Pro Leu Lys Glu Leu Phe Lys Asp Glu Val
     370                 375                 380 cgt aag att ggt ctg gag ctg ggc ctg ccg tac gac atg ctg tac cgt    1200
Arg Lys Ile Gly Leu Glu Leu Gly Leu Pro Tyr Asp Met Leu Tyr Arg
385                 390                 395                 400 cac ccg ttc ccg gga cca ggc ctt ggc gtt cgt gtt ctg ggt gaa gtg    1248
His Pro Phe Pro Gly Pro Gly Leu Gly Val Arg Val Leu Gly Glu Val
                 405                 410                 415 aag aaa gag tac tgt gac ctg ctg cgc cgt gct gac gcc atc ttc att    1296
Lys Lys Glu Tyr Cys Asp Leu Leu Arg Arg Ala Asp Ala Ile Phe Ile
             420                 425                 430 gaa gaa ctg cgt aaa gcg gac ctg tac gac aaa gtc agc cag gcg ttc    1344
Glu Glu Leu Arg Lys Ala Asp Leu Tyr Asp Lys Val Ser Gln Ala Phe
         435                 440                 445 act gtg ttc ctg ccg gta cgt tcc gtt ggc gta atg ggc gat ggt cgt    1392
Thr Val Phe Leu Pro Val Arg Ser Val Gly Val Met Gly Asp Gly Arg
     450                 455                 460 aag tat gac tgg gtt gtc tct ctg cgt gct gtc gaa acc atc gac ttt    1440
Lys Tyr Asp Trp Val Val Ser Leu Arg Ala Val Glu Thr Ile Asp Phe
465                 470                 475                 480 atg acc gca cac tgg gcg cat ctg ccg tac gat ttc ctc ggt cgc gtt    1488
Met Thr Ala His Trp Ala His Leu Pro Tyr Asp Phe Leu Gly Arg Val
                 485                 490                 495 tcc aac cgc att atc aat gaa gtg aac ggt att tcc cgc gtg gtg tat    1536
Ser Asn Arg Ile Ile Asn Glu Val Asn Gly Ile Ser Arg Val Val Tyr
             500                 505                 510 gac atc agc ggc aag ccg cca gct acc att gag tgg gaa tga            1578
Asp Ile Ser Gly Lys Pro Pro Ala Thr Ile Glu Trp Glu
         515                 520                 525

<210> SEQ ID NO 2
<211> LENGTH: 525
<212> TYPE: PRT
<213> ORGANISM: Escherichia coli

<400> SEQUENCE: 2

Met Thr Glu Asn Ile His Lys His Arg Ile Leu Ile Leu Asp Phe Gly
1               5                   10                  15

Ser Gln Tyr Thr Gln Leu Val Ala Arg Arg Val Arg Glu Leu Gly Val
            20                  25                  30

Tyr Cys Glu Leu Trp Ala Trp Asp Val Thr Glu Ala Gln Ile Arg Asp
        35                  40                  45

Phe Asn Pro Ser Gly Ile Ile Leu Ser Gly Gly Pro Glu Ser Thr Thr
    50                  55                  60

Glu Glu Asn Ser Pro Arg Ala Pro Gln Tyr Val Phe Glu Ala Gly Val
65                  70                  75                  80

Pro Val Phe Gly Val Cys Tyr Gly Met Gln Thr Met Ala Met Gln Leu
                85                  90                  95

Gly Gly His Val Glu Ala Ser Asn Glu Arg Glu Phe Gly Tyr Ala Gln
            100                 105                 110

Val Glu Val Val Asn Asp Ser Ala Leu Val Arg Gly Ile Glu Asp Ala
```

```
                115                 120                 125
Leu Thr Ala Asp Gly Lys Pro Leu Leu Asp Val Trp Met Ser His Gly
130                 135                 140

Asp Lys Val Thr Ala Ile Pro Ser Asp Phe Ile Thr Val Ala Ser Thr
145                 150                 155                 160

Glu Ser Cys Pro Phe Ala Ile Met Ala Asn Glu Lys Arg Phe Tyr
            165                 170                 175

Gly Val Gln Phe His Pro Glu Val Thr His Thr Arg Gln Gly Met Arg
                180                 185                 190

Met Leu Glu Arg Phe Val Arg Asp Ile Cys Gln Cys Glu Ala Leu Trp
            195                 200                 205

Thr Pro Ala Lys Ile Ile Asp Asp Ala Val Ala Arg Ile Arg Glu Gln
210                 215                 220

Val Gly Asp Asp Lys Val Ile Leu Gly Leu Ser Gly Gly Val Asp Ser
225                 230                 235                 240

Ser Val Thr Ala Met Leu Leu His Arg Ala Ile Gly Lys Asn Leu Thr
                245                 250                 255

Cys Val Phe Val Asp Asn Gly Leu Leu Arg Leu Asn Glu Ala Glu Gln
            260                 265                 270

Val Leu Asp Met Phe Gly Asp His Phe Gly Leu Asn Ile Val His Val
                275                 280                 285

Pro Ala Glu Asp Arg Phe Leu Ser Ala Leu Ala Gly Glu Asn Asp Pro
290                 295                 300

Glu Ala Lys Arg Lys Ile Ile Gly Arg Val Phe Val Glu Val Phe Asp
305                 310                 315                 320

Glu Glu Ala Leu Lys Leu Glu Asp Val Lys Trp Leu Ala Gln Gly Thr
                325                 330                 335

Ile Tyr Pro Asp Val Ile Glu Ser Ala Ala Ser Ala Thr Gly Lys Ala
            340                 345                 350

His Val Ile Lys Ser His His Asn Val Gly Gly Leu Pro Lys Glu Met
                355                 360                 365

Lys Met Gly Leu Val Glu Pro Leu Lys Glu Leu Phe Lys Asp Glu Val
370                 375                 380

Arg Lys Ile Gly Leu Glu Leu Gly Leu Pro Tyr Asp Met Leu Tyr Arg
385                 390                 395                 400

His Pro Phe Pro Gly Pro Gly Leu Gly Val Arg Val Leu Gly Glu Val
                405                 410                 415

Lys Lys Glu Tyr Cys Asp Leu Leu Arg Arg Ala Asp Ala Ile Phe Ile
            420                 425                 430

Glu Glu Leu Arg Lys Ala Asp Leu Tyr Asp Lys Val Ser Gln Ala Phe
                435                 440                 445

Thr Val Phe Leu Pro Val Arg Ser Val Gly Val Met Gly Asp Gly Arg
450                 455                 460

Lys Tyr Asp Trp Val Val Ser Leu Arg Ala Val Glu Thr Ile Asp Phe
465                 470                 475                 480

Met Thr Ala His Trp Ala His Leu Pro Tyr Asp Phe Leu Gly Arg Val
                485                 490                 495

Ser Asn Arg Ile Ile Asn Glu Val Asn Gly Ile Ser Arg Val Val Tyr
            500                 505                 510

Asp Ile Ser Gly Lys Pro Pro Ala Thr Ile Glu Trp Glu
515                 520                 525

<210> SEQ ID NO 3
<211> LENGTH: 1542
```

```
<212> TYPE: DNA
<213> ORGANISM: Bacillus subtilis
<220> FEATURE:
<221> NAME/KEY: CDS
<222> LOCATION: (1)..(1539)

<400> SEQUENCE: 3 atg aca aag tta gtg aat gaa atg att ctt gtc ctt gat ttc ggc agt     48
Met Thr Lys Leu Val Asn Glu Met Ile Leu Val Leu Asp Phe Gly Ser
1               5                  10                  15 cag tat aac cag ctg att aca cgc cgt atc cgt gaa ttc ggt gtt tac     96
Gln Tyr Asn Gln Leu Ile Thr Arg Arg Ile Arg Glu Phe Gly Val Tyr
            20                  25                  30 agc gag ctg cat cca cat aca ttg acg gct gaa gaa att aaa aaa atg    144
Ser Glu Leu His Pro His Thr Leu Thr Ala Glu Glu Ile Lys Lys Met
        35                  40                  45 aat cca aaa gga att att tta tcc ggc ggt cca aac agt gtg tat gat    192
Asn Pro Lys Gly Ile Ile Leu Ser Gly Gly Pro Asn Ser Val Tyr Asp
    50                  55                  60 gaa aac tct ttc cgc tgt gac gag aaa atc ttc gag ctt gat att cct    240
Glu Asn Ser Phe Arg Cys Asp Glu Lys Ile Phe Glu Leu Asp Ile Pro
65                  70                  75                  80 gtt ttg gga att tgc tac ggc atg cag ctg atg act cat tac ctt ggc    288
Val Leu Gly Ile Cys Tyr Gly Met Gln Leu Met Thr His Tyr Leu Gly
                85                  90                  95 ggt aaa gtt gaa gcg gca agc cag cgt gaa tac gga aaa gca aac atc    336
Gly Lys Val Glu Ala Ala Ser Gln Arg Glu Tyr Gly Lys Ala Asn Ile
            100                 105                 110 cgc atc gaa ggc aca cct gat ttg ttc aga gat ctt ccg aat gaa caa    384
Arg Ile Glu Gly Thr Pro Asp Leu Phe Arg Asp Leu Pro Asn Glu Gln
        115                 120                 125 gtg gtt tgg atg agc cac ggc gat ttg gtt gta gaa gtt cct gaa ggc    432
Val Val Trp Met Ser His Gly Asp Leu Val Val Glu Val Pro Glu Gly
    130                 135                 140 ttc act gtt gac gcg aca agc cat cac tgc ccg aac tca gca atg agc    480
Phe Thr Val Asp Ala Thr Ser His His Cys Pro Asn Ser Ala Met Ser
145                 150                 155                 160 aaa gcg gac aaa aaa tgg tat ggc gtt cag ttc cac ccg gaa gtg cgc    528
Lys Ala Asp Lys Lys Trp Tyr Gly Val Gln Phe His Pro Glu Val Arg
                165                 170                 175 cac tct gaa tac ggc aat gat ctt ctg aaa aac ttt gta ttc ggt gtt    576
His Ser Glu Tyr Gly Asn Asp Leu Leu Lys Asn Phe Val Phe Gly Val
            180                 185                 190 tgc gaa tgc gaa ggc gaa tgg tca atg gag aac ttt atc gaa atc gaa    624
Cys Glu Cys Glu Gly Glu Trp Ser Met Glu Asn Phe Ile Glu Ile Glu
        195                 200                 205 atg caa aaa atc cgt gaa acg tcg gga gac aaa cag gtt ctt tgc gcg    672
Met Gln Lys Ile Arg Glu Thr Val Gly Asp Lys Gln Val Leu Cys Ala
    210                 215                 220 cta agc ggc ggc gtt gat tcc tct gtt gtt gct gtt ttg att cat aaa    720
Leu Ser Gly Gly Val Asp Ser Ser Val Val Ala Val Leu Ile His Lys
225                 230                 235                 240 gcg atc ggc gac cag ctg act tgt atc ttt gta gac cat ggt ctt ctc    768
Ala Ile Gly Asp Gln Leu Thr Cys Ile Phe Val Asp His Gly Leu Leu
                245                 250                 255 cgt aaa ggc gaa gct gag ggt gtt atg aaa aca ttc agc gaa ggc ttt    816
Arg Lys Gly Glu Ala Glu Gly Val Met Lys Thr Phe Ser Glu Gly Phe
            260                 265                 270 aac atg aat gtg att aaa gta gac gca aaa gat cga ttc tta aac aaa    864
Asn Met Asn Val Ile Lys Val Asp Ala Lys Asp Arg Phe Leu Asn Lys
        275                 280                 285
```

```
cta aaa ggc gtt tct gat cct gag caa aaa cgc aaa atc atc ggt aat    912
Leu Lys Gly Val Ser Asp Pro Glu Gln Lys Arg Lys Ile Ile Gly Asn
    290             295                 300 gaa ttc att tac gtg ttt gat gat gaa gcg gac aag ctc aaa ggc atc    960
Glu Phe Ile Tyr Val Phe Asp Asp Glu Ala Asp Lys Leu Lys Gly Ile
305                 310                 315                 320 gac tac ctt gca caa ggt acg ctt tac aca gat atc atc gag agc ggt   1008
Asp Tyr Leu Ala Gln Gly Thr Leu Tyr Thr Asp Ile Ile Glu Ser Gly
                325                 330                 335 aca gca acg gcg caa acg atc aaa tct cac cac aat gtc ggc gga ctt   1056
Thr Ala Thr Ala Gln Thr Ile Lys Ser His His Asn Val Gly Gly Leu
            340                 345                 350 cct gaa gac atg cag ttt gag ctg atc gag ccg tta aat acg ctc ttc   1104
Pro Glu Asp Met Gln Phe Glu Leu Ile Glu Pro Leu Asn Thr Leu Phe
        355                 360                 365 aaa gac gaa gtg cgc gcg ctt ggc aca gag ctc ggc att ccg gat gaa   1152
Lys Asp Glu Val Arg Ala Leu Gly Thr Glu Leu Gly Ile Pro Asp Glu
    370                 375                 380 atc gta tgg cgt cag ccg ttc cca gga ccg gga ctc gga atc cgc gtt   1200
Ile Val Trp Arg Gln Pro Phe Pro Gly Pro Gly Leu Gly Ile Arg Val
385                 390                 395                 400 ctt ggc gaa gta aca gaa gaa aaa ctt gaa atc gtt cgt gaa tca gat   1248
Leu Gly Glu Val Thr Glu Glu Lys Leu Glu Ile Val Arg Glu Ser Asp
                405                 410                 415 gca atc ttg cgt gaa gaa att gca aat cac ggc tta gag cgt gat atc   1296
Ala Ile Leu Arg Glu Glu Ile Ala Asn His Gly Leu Glu Arg Asp Ile
            420                 425                 430 tgg caa tac ttc act gtt ctt cct gac atc cgc agc gtt ggt gtt atg   1344
Trp Gln Tyr Phe Thr Val Leu Pro Asp Ile Arg Ser Val Gly Val Met
        435                 440                 445 ggt gac gca aga aca tat gat tac aca atc gga atc cgc gcc gtt aca   1392
Gly Asp Ala Arg Thr Tyr Asp Tyr Thr Ile Gly Ile Arg Ala Val Thr
    450                 455                 460 tca atc gac ggc atg aca tct gac tgg gcg cgt atc ccg tgg gat gtg   1440
Ser Ile Asp Gly Met Thr Ser Asp Trp Ala Arg Ile Pro Trp Asp Val
465                 470                 475                 480 ctt gaa gtc att tcg aca cgt atc gta aac gaa gtg aag cac att aac   1488
Leu Glu Val Ile Ser Thr Arg Ile Val Asn Glu Val Lys His Ile Asn
                485                 490                 495 cgc gtg gtg tat gat att aca agt aag ccg cct gcg acg att gag tgg   1536
Arg Val Val Tyr Asp Ile Thr Ser Lys Pro Pro Ala Thr Ile Glu Trp
            500                 505                 510 gaa taa                                                            1542
Glu
```

<210> SEQ ID NO 4
<211> LENGTH: 513
<212> TYPE: PRT
<213> ORGANISM: Bacillus subtilis

<400> SEQUENCE: 4

```
Met Thr Lys Leu Val Asn Glu Met Ile Leu Val Leu Asp Phe Gly Ser
1               5                   10                  15

Gln Tyr Asn Gln Leu Ile Thr Arg Arg Ile Arg Glu Phe Gly Val Tyr
            20                  25                  30

Ser Glu Leu His Pro His Thr Leu Thr Ala Glu Glu Ile Lys Lys Met
        35                  40                  45

Asn Pro Lys Gly Ile Ile Leu Ser Gly Gly Pro Asn Ser Val Tyr Asp
    50                  55                  60

Glu Asn Ser Phe Arg Cys Asp Glu Lys Ile Phe Glu Leu Asp Ile Pro
```

```
                65                  70                  75                  80
Val Leu Gly Ile Cys Tyr Gly Met Gln Leu Met Thr His Tyr Leu Gly
                        85                  90                  95
Gly Lys Val Glu Ala Ala Ser Gln Arg Glu Tyr Gly Lys Ala Asn Ile
            100                 105                 110
Arg Ile Glu Gly Thr Pro Asp Leu Phe Arg Asp Leu Pro Asn Glu Gln
        115                 120                 125
Val Val Trp Met Ser His Gly Asp Leu Val Val Glu Val Pro Glu Gly
    130                 135                 140
Phe Thr Val Asp Ala Thr Ser His His Cys Pro Asn Ser Ala Met Ser
145                 150                 155                 160
Lys Ala Asp Lys Lys Trp Tyr Gly Val Gln Phe His Pro Glu Val Arg
                165                 170                 175
His Ser Glu Tyr Gly Asn Asp Leu Leu Lys Asn Phe Val Phe Gly Val
            180                 185                 190
Cys Glu Cys Glu Gly Glu Trp Ser Met Glu Asn Phe Ile Glu Ile Glu
        195                 200                 205
Met Gln Lys Ile Arg Glu Thr Val Gly Asp Lys Gln Val Leu Cys Ala
    210                 215                 220
Leu Ser Gly Gly Val Asp Ser Ser Val Val Ala Val Leu Ile His Lys
225                 230                 235                 240
Ala Ile Gly Asp Gln Leu Thr Cys Ile Phe Val Asp His Gly Leu Leu
                245                 250                 255
Arg Lys Gly Glu Ala Glu Gly Val Met Lys Thr Phe Ser Glu Gly Phe
            260                 265                 270
Asn Met Asn Val Ile Lys Val Asp Ala Lys Asp Arg Phe Leu Asn Lys
        275                 280                 285
Leu Lys Gly Val Ser Asp Pro Glu Gln Lys Arg Lys Ile Ile Gly Asn
    290                 295                 300
Glu Phe Ile Tyr Val Phe Asp Asp Glu Ala Asp Lys Leu Lys Gly Ile
305                 310                 315                 320
Asp Tyr Leu Ala Gln Gly Thr Leu Tyr Thr Asp Ile Ile Glu Ser Gly
                325                 330                 335
Thr Ala Thr Ala Gln Thr Ile Lys Ser His His Asn Val Gly Gly Leu
            340                 345                 350
Pro Glu Asp Met Gln Phe Glu Leu Ile Glu Pro Leu Asn Thr Leu Phe
        355                 360                 365
Lys Asp Glu Val Arg Ala Leu Gly Thr Glu Leu Gly Ile Pro Asp Glu
    370                 375                 380
Ile Val Trp Arg Gln Pro Phe Pro Gly Pro Gly Leu Gly Ile Arg Val
385                 390                 395                 400
Leu Gly Glu Val Thr Glu Glu Lys Leu Glu Ile Val Arg Glu Ser Asp
                405                 410                 415
Ala Ile Leu Arg Glu Glu Ile Ala Asn His Gly Leu Glu Arg Asp Ile
            420                 425                 430
Trp Gln Tyr Phe Thr Val Leu Pro Asp Ile Arg Ser Val Gly Val Met
        435                 440                 445
Gly Asp Ala Arg Thr Tyr Asp Tyr Thr Ile Gly Ile Arg Ala Val Thr
    450                 455                 460
Ser Ile Asp Gly Met Thr Ser Asp Trp Ala Arg Ile Pro Trp Asp Val
465                 470                 475                 480
Leu Glu Val Ile Ser Thr Arg Ile Val Asn Glu Val Lys His Ile Asn
                485                 490                 495
```

```
                    Arg Val Val Tyr Asp Ile Thr Ser Lys Pro Pro Ala Thr Ile Glu Trp
                                500                 505                 510

Glu

<210> SEQ ID NO 5
<211> LENGTH: 1572
<212> TYPE: DNA
<213> ORGANISM: Corynebacterium glutamicum
<220> FEATURE:
<221> NAME/KEY: CDS
<222> LOCATION: (1)..(1569)

<400> SEQUENCE: 5 gtg agc ctt cag aca aat cat cgc cca gta ctc gtc gtt gac ttc ggc         48
Val Ser Leu Gln Thr Asn His Arg Pro Val Leu Val Val Asp Phe Gly
1               5                   10                  15 gca cag tac gcg cag ctg atc gca cgt cgt gtg cgt gag gcc ggc atc         96
Ala Gln Tyr Ala Gln Leu Ile Ala Arg Arg Val Arg Glu Ala Gly Ile
            20                  25                  30 tac tcc gaa gtc atc ccg cac acc gcc acc gca gac gat gtg cgc gct        144
Tyr Ser Glu Val Ile Pro His Thr Ala Thr Ala Asp Asp Val Arg Ala
        35                  40                  45 aaa aat gca gca gcc ctc gtc ctt tcc ggt ggc cca tcc tcc gtg tat        192
Lys Asn Ala Ala Ala Leu Val Leu Ser Gly Gly Pro Ser Ser Val Tyr
    50                  55                  60 gcc gag gga gca cca tcc ctt gac gct gag att ctt gat ctc gga ttg        240
Ala Glu Gly Ala Pro Ser Leu Asp Ala Glu Ile Leu Asp Leu Gly Leu
65                  70                  75                  80 cca gta ttt ggc att tgc tac ggc ttc caa gcc atg acc cac gcg ctt        288
Pro Val Phe Gly Ile Cys Tyr Gly Phe Gln Ala Met Thr His Ala Leu
                85                  90                  95 ggt ggc acc gtt gcc aac acc ggt aag cgc gaa tac gga cgc acc gac        336
Gly Gly Thr Val Ala Asn Thr Gly Lys Arg Glu Tyr Gly Arg Thr Asp
            100                 105                 110 atc aac gtt gcc ggt ggc gtc ctc cac gaa ggc ctc gaa gcc tgc cac        384
Ile Asn Val Ala Gly Gly Val Leu His Glu Gly Leu Glu Ala Cys His
        115                 120                 125 aag gtg tgg atg agc cac ggc gac gcc gtc tct gaa gcc cca gaa ggt        432
Lys Val Trp Met Ser His Gly Asp Ala Val Ser Glu Ala Pro Glu Gly
    130                 135                 140 ttc gta gtc acc gcg tcc tcc gaa ggt gcg cct gtc gca gct ttc gaa        480
Phe Val Val Thr Ala Ser Ser Glu Gly Ala Pro Val Ala Ala Phe Glu
145                 150                 155                 160 aac aag gaa cgc aaa atg gct ggc gtg cag tac cac cca gag gta ttg        528
Asn Lys Glu Arg Lys Met Ala Gly Val Gln Tyr His Pro Glu Val Leu
                165                 170                 175 cac tca cca cac ggc cag gca gtt ctg acc cgc ttc ctc act gag atc        576
His Ser Pro His Gly Gln Ala Val Leu Thr Arg Phe Leu Thr Glu Ile
            180                 185                 190 gca ggt cta gag cag aac tgg acc gca gca aac atc gct gaa gaa ctc        624
Ala Gly Leu Glu Gln Asn Trp Thr Ala Ala Asn Ile Ala Glu Glu Leu
        195                 200                 205 atc gaa aag gtc cgc gag cag atc ggc gaa gat ggc cgc gct att tgt        672
Ile Glu Lys Val Arg Glu Gln Ile Gly Glu Asp Gly Arg Ala Ile Cys
    210                 215                 220 ggc cta tcc ggt ggt gtg gac tcc gct gtt gcc ggt gct ttg gtg cag        720
Gly Leu Ser Gly Gly Val Asp Ser Ala Val Ala Gly Ala Leu Val Gln
225                 230                 235                 240 cgc gcc att ggt gac cgt ttg acc tgt gtc ttt gtt gac cac ggt ctg        768
Arg Ala Ile Gly Asp Arg Leu Thr Cys Val Phe Val Asp His Gly Leu
                245                 250                 255
```

```
ctg cgt gcc ggt gag cgc gag cag gtg gaa aaa gac ttc gtc gca gca    816
Leu Arg Ala Gly Glu Arg Glu Gln Val Glu Lys Asp Phe Val Ala Ala
        260                 265                 270 acc ggc gcc aag ctg gtt acc gtt gat gag cgc cag gca ttc cta tcc    864
Thr Gly Ala Lys Leu Val Thr Val Asp Glu Arg Gln Ala Phe Leu Ser
    275                 280                 285 aag ctg gcc gga gtt acc gaa cca gaa gca aag cgc aag gct atc ggc    912
Lys Leu Ala Gly Val Thr Glu Pro Glu Ala Lys Arg Lys Ala Ile Gly
290                 295                 300 gct gag ttc atc cgc tcc ttc gag cgc gca gtt gcc ggt gtg ctg gaa    960
Ala Glu Phe Ile Arg Ser Phe Glu Arg Ala Val Ala Gly Val Leu Glu
305                 310                 315                 320 gaa gct cca gaa ggt tcc acc gtg gac ttc ctg gtt cag ggc acc ctg   1008
Glu Ala Pro Glu Gly Ser Thr Val Asp Phe Leu Val Gln Gly Thr Leu
            325                 330                 335 tac cca gac gtc gtg gaa tcc ggt ggt gga tct ggt acc gca aac atc   1056
Tyr Pro Asp Val Val Glu Ser Gly Gly Gly Ser Gly Thr Ala Asn Ile
        340                 345                 350 aag agc cac cac aac gtc ggt gga ctg cca gac gat gtg gaa ttc aag   1104
Lys Ser His His Asn Val Gly Gly Leu Pro Asp Asp Val Glu Phe Lys
    355                 360                 365 ctt gtt gag cca ctg cgt gac ctc ttc aaa gac gaa gtc cgt gcc gtt   1152
Leu Val Glu Pro Leu Arg Asp Leu Phe Lys Asp Glu Val Arg Ala Val
370                 375                 380 ggc cgt gaa ctt ggc ctg cct gag gaa atc gtt ggc cgc cag cca ttc   1200
Gly Arg Glu Leu Gly Leu Pro Glu Glu Ile Val Gly Arg Gln Pro Phe
385                 390                 395                 400 cca gga cca gga ctt ggt atc cgc atc atc ggt gaa gtc acc gaa gat   1248
Pro Gly Pro Gly Leu Gly Ile Arg Ile Ile Gly Glu Val Thr Glu Asp
            405                 410                 415 cgc cta gaa acc ctc cgc cac gct gac ctg atc gcc cgc acc gag ctc   1296
Arg Leu Glu Thr Leu Arg His Ala Asp Leu Ile Ala Arg Thr Glu Leu
        420                 425                 430 acc gaa gcc gga ctt gac ggc gtg atc tgg cag tgc cca gta gtc ctc   1344
Thr Glu Ala Gly Leu Asp Gly Val Ile Trp Gln Cys Pro Val Val Leu
    435                 440                 445 ctg gca gat gtc cgc tct gtt ggt gtt caa ggc gat ggc cgc acc tac   1392
Leu Ala Asp Val Arg Ser Val Gly Val Gln Gly Asp Gly Arg Thr Tyr
450                 455                 460 gga cac cca atc gtg ctg cgc cca gtg tct tcc gaa gac gca atg acc   1440
Gly His Pro Ile Val Leu Arg Pro Val Ser Ser Glu Asp Ala Met Thr
465                 470                 475                 480 gcc gac tgg acc cgc ctg cca tac gag gtt ctg gag aag atc tcc acc   1488
Ala Asp Trp Thr Arg Leu Pro Tyr Glu Val Leu Glu Lys Ile Ser Thr
            485                 490                 495 cgc atc acc aac gaa gtt cca gat gtg aac cgc gtg gtg ctg gac gta   1536
Arg Ile Thr Asn Glu Val Pro Asp Val Asn Arg Val Val Leu Asp Val
        500                 505                 510 acc tcc aag cca cca gga acc atc gaa tgg gag tag                    1572
Thr Ser Lys Pro Pro Gly Thr Ile Glu Trp Glu
    515                 520

<210> SEQ ID NO 6
<211> LENGTH: 523
<212> TYPE: PRT
<213> ORGANISM: Corynebacterium glutamicum

<400> SEQUENCE: 6

Val Ser Leu Gln Thr Asn His Arg Pro Val Leu Val Val Asp Phe Gly
1               5                   10                  15

Ala Gln Tyr Ala Gln Leu Ile Ala Arg Arg Val Arg Glu Ala Gly Ile
```

```
                    20                  25                  30
Tyr Ser Glu Val Ile Pro His Thr Ala Thr Ala Asp Asp Val Arg Ala
                35                  40                  45

Lys Asn Ala Ala Ala Leu Val Leu Ser Gly Gly Pro Ser Ser Val Tyr
         50                  55                  60

Ala Glu Gly Ala Pro Ser Leu Asp Ala Glu Ile Leu Asp Leu Gly Leu
 65                  70                  75                  80

Pro Val Phe Gly Ile Cys Tyr Gly Phe Gln Ala Met Thr His Ala Leu
                85                  90                  95

Gly Gly Thr Val Ala Asn Thr Gly Lys Arg Glu Tyr Gly Arg Thr Asp
               100                 105                 110

Ile Asn Val Ala Gly Gly Val Leu His Glu Gly Leu Glu Ala Cys His
               115                 120                 125

Lys Val Trp Met Ser His Gly Asp Ala Val Ser Glu Ala Pro Glu Gly
               130                 135                 140

Phe Val Val Thr Ala Ser Ser Glu Gly Ala Pro Val Ala Phe Glu
145                 150                 155                 160

Asn Lys Glu Arg Lys Met Ala Gly Val Gln Tyr His Pro Glu Val Leu
               165                 170                 175

His Ser Pro His Gly Gln Ala Val Leu Thr Arg Phe Leu Thr Glu Ile
               180                 185                 190

Ala Gly Leu Glu Gln Asn Trp Thr Ala Ala Asn Ile Ala Glu Glu Leu
               195                 200                 205

Ile Glu Lys Val Arg Glu Gln Ile Gly Glu Asp Gly Arg Ala Ile Cys
               210                 215                 220

Gly Leu Ser Gly Gly Val Asp Ser Ala Val Ala Gly Ala Leu Val Gln
225                 230                 235                 240

Arg Ala Ile Gly Asp Arg Leu Thr Cys Val Phe Val Asp His Gly Leu
               245                 250                 255

Leu Arg Ala Gly Glu Arg Glu Gln Val Glu Lys Asp Phe Val Ala Ala
               260                 265                 270

Thr Gly Ala Lys Leu Val Thr Val Asp Glu Arg Gln Ala Phe Leu Ser
               275                 280                 285

Lys Leu Ala Gly Val Thr Glu Pro Glu Ala Lys Arg Lys Ala Ile Gly
               290                 295                 300

Ala Glu Phe Ile Arg Ser Phe Glu Arg Ala Val Ala Gly Val Leu Glu
305                 310                 315                 320

Glu Ala Pro Glu Gly Ser Thr Val Asp Phe Leu Val Gln Gly Thr Leu
               325                 330                 335

Tyr Pro Asp Val Val Glu Ser Gly Gly Ser Gly Thr Ala Asn Ile
               340                 345                 350

Lys Ser His His Asn Val Gly Gly Leu Pro Asp Asp Val Glu Phe Lys
               355                 360                 365

Leu Val Glu Pro Leu Arg Asp Leu Phe Lys Asp Glu Val Arg Ala Val
               370                 375                 380

Gly Arg Glu Leu Gly Leu Pro Glu Glu Ile Val Gly Arg Gln Pro Phe
385                 390                 395                 400

Pro Gly Pro Gly Leu Gly Ile Arg Ile Ile Gly Glu Val Thr Glu Asp
               405                 410                 415

Arg Leu Glu Thr Leu Arg His Ala Asp Leu Ile Ala Arg Thr Glu Leu
               420                 425                 430

Thr Glu Ala Gly Leu Asp Gly Val Ile Trp Gln Cys Pro Val Val Leu
               435                 440                 445
```

```
Leu Ala Asp Val Arg Ser Val Gly Val Gln Gly Asp Gly Arg Thr Tyr
    450                 455                 460

Gly His Pro Ile Val Leu Arg Pro Val Ser Ser Glu Asp Ala Met Thr
465                 470                 475                 480

Ala Asp Trp Thr Arg Leu Pro Tyr Glu Val Leu Glu Lys Ile Ser Thr
                    485                 490                 495

Arg Ile Thr Asn Glu Val Pro Asp Val Asn Arg Val Val Leu Asp Val
                500                 505                 510

Thr Ser Lys Pro Pro Gly Thr Ile Glu Trp Glu
            515                 520

<210> SEQ ID NO 7
<211> LENGTH: 1575
<212> TYPE: DNA
<213> ORGANISM: Corynebacterium ammoniagenes
<220> FEATURE:
<221> NAME/KEY: CDS
<222> LOCATION: (1)..(1572)

<400> SEQUENCE: 7
```

| | | | | | | | | | | | | | | | | |
|---|---|---|---|---|---|---|---|---|---|---|---|---|---|---|---|---|
| gtg | act | caa | cct | gca | aca | act | ccg | cgc | cca | gtc | ctc | gtg | gtg | gat | ttc | 48 |
| Val | Thr | Gln | Pro | Ala | Thr | Thr | Pro | Arg | Pro | Val | Leu | Val | Val | Asp | Phe | |
| 1 | | | | 5 | | | | | 10 | | | | | 15 | | |
| ggt | gcc | caa | tac | gca | cag | ctg | att | gct | cgt | cgc | gta | cgt | gag | gca | tcg | 96 |
| Gly | Ala | Gln | Tyr | Ala | Gln | Leu | Ile | Ala | Arg | Arg | Val | Arg | Glu | Ala | Ser | |
| | | 20 | | | | | 25 | | | | | 30 | | | | |
| att | tac | tcc | gag | gta | gtc | cca | cat | tcc | gcc | acc | gtt | aaa | gag | att | aaa | 144 |
| Ile | Tyr | Ser | Glu | Val | Val | Pro | His | Ser | Ala | Thr | Val | Lys | Glu | Ile | Lys | |
| | | | 35 | | | | | 40 | | | | | 45 | | | |
| gct | aaa | aac | cct | gca | gct | ttg | att | ttg | tcc | ggt | ggc | ccg | tcc | tct | gtt | 192 |
| Ala | Lys | Asn | Pro | Ala | Ala | Leu | Ile | Leu | Ser | Gly | Gly | Pro | Ser | Ser | Val | |
| | 50 | | | | | 55 | | | | | 60 | | | | | |
| tat | gcc | gat | ggc | gcc | ccg | caa | tta | aag | cct | gaa | ctg | ctc | gag | ctt | ggt | 240 |
| Tyr | Ala | Asp | Gly | Ala | Pro | Gln | Leu | Lys | Pro | Glu | Leu | Leu | Glu | Leu | Gly | |
| 65 | | | | | 70 | | | | | 75 | | | | | 80 | |
| gtg | cca | gtc | ttt | ggc | atc | tgc | tac | ggc | ttc | caa | gcc | atg | aac | cat | gct | 288 |
| Val | Pro | Val | Phe | Gly | Ile | Cys | Tyr | Gly | Phe | Gln | Ala | Met | Asn | His | Ala | |
| | | | | 85 | | | | | 90 | | | | | 95 | | |
| ttg | ggt | ggc | aac | gtt | gcg | caa | acc | ggt | gac | cgt | gaa | tac | ggc | cgc | acc | 336 |
| Leu | Gly | Gly | Asn | Val | Ala | Gln | Thr | Gly | Asp | Arg | Glu | Tyr | Gly | Arg | Thr | |
| | | | 100 | | | | | 105 | | | | | 110 | | | |
| gaa | atc | acc | cat | acc | ggt | ggt | gtg | ctg | cac | gac | ggc | tta | gaa | gaa | aac | 384 |
| Glu | Ile | Thr | His | Thr | Gly | Gly | Val | Leu | His | Asp | Gly | Leu | Glu | Glu | Asn | |
| | | 115 | | | | | 120 | | | | | 125 | | | | |
| cac | aag | gtc | tgg | atg | tcc | cac | ggt | gat | gct | gtg | gat | aag | gca | cct | gag | 432 |
| His | Lys | Val | Trp | Met | Ser | His | Gly | Asp | Ala | Val | Asp | Lys | Ala | Pro | Glu | |
| | 130 | | | | | 135 | | | | | 140 | | | | | |
| ggc | ttt | acc | gtg | acc | gca | tcg | tcg | gct | ggt | gcg | ccg | gtt | gca | gcg | atg | 480 |
| Gly | Phe | Thr | Val | Thr | Ala | Ser | Ser | Ala | Gly | Ala | Pro | Val | Ala | Ala | Met | |
| 145 | | | | | 150 | | | | | 155 | | | | | 160 | |
| gaa | tgc | gtg | gcc | aag | caa | atg | gct | ggt | gtg | caa | tac | cac | ccc | gag | gtt | 528 |
| Glu | Cys | Val | Ala | Lys | Gln | Met | Ala | Gly | Val | Gln | Tyr | His | Pro | Glu | Val | |
| | | | | 165 | | | | | 170 | | | | | 175 | | |
| atg | cat | tcc | cca | cac | gga | cag | gaa | gta | ctc | gtt | cgc | ttc | ctc | acc | gag | 576 |
| Met | His | Ser | Pro | His | Gly | Gln | Glu | Val | Leu | Val | Arg | Phe | Leu | Thr | Glu | |
| | | | 180 | | | | | 185 | | | | | 190 | | | |
| gta | gca | ggg | cta | gag | cag | acc | tgg | acc | tcg | gca | aat | att | gcg | cag | cag | 624 |
| Val | Ala | Gly | Leu | Glu | Gln | Thr | Trp | Thr | Ser | Ala | Asn | Ile | Ala | Gln | Gln | |
| | | 195 | | | | | 200 | | | | | 205 | | | | |
| ctt | atc | gat | gat | gtc | cgc | gcg | caa | atc | ggc | cct | gaa | ggc | cgc | gct | att | 672 |
| Leu | Ile | Asp | Asp | Val | Arg | Ala | Gln | Ile | Gly | Pro | Glu | Gly | Arg | Ala | Ile | |

```
              210                 215                 220
tgt ggc ctg tcg ggc ggc gtg gac tcc gca gtc gct gca gcg ctc gtg    720
Cys Gly Leu Ser Gly Gly Val Asp Ser Ala Val Ala Ala Ala Leu Val
225                 230                 235                 240 cag cgc gcc att ggc gac cgt ttg acc tgt gtg ttc gtg gac cac ggt    768
Gln Arg Ala Ile Gly Asp Arg Leu Thr Cys Val Phe Val Asp His Gly
            245                 250                 255 ctg ctg cgc gcc ggt gag cgt gag cag gta gaa aag gac ttc gtg gct    816
Leu Leu Arg Ala Gly Glu Arg Glu Gln Val Glu Lys Asp Phe Val Ala
        260                 265                 270 tcg act ggt gcg aag ctg att acc gcg cat gaa gct gat gct ttc ttg    864
Ser Thr Gly Ala Lys Leu Ile Thr Ala His Glu Ala Asp Ala Phe Leu
    275                 280                 285 tct aag ctc gcc ggt gtt acc gat cct gag gct aag cgc aag gct atc    912
Ser Lys Leu Ala Gly Val Thr Asp Pro Glu Ala Lys Arg Lys Ala Ile
290                 295                 300 ggc gcg gaa ttc atc cgt tcc ttt gag cgt gct gtg gca cag gct ttg    960
Gly Ala Glu Phe Ile Arg Ser Phe Glu Arg Ala Val Ala Gln Ala Leu
305                 310                 315                 320 gaa gaa tct cct gaa gac tcc aca gtg gac ttc ctg gtc cag ggc acc    1008
Glu Glu Ser Pro Glu Asp Ser Thr Val Asp Phe Leu Val Gln Gly Thr
            325                 330                 335 ttg tat ccg gat gtg gtt gaa tcc ggc ggc ggt gac ggc acc gca aat    1056
Leu Tyr Pro Asp Val Val Glu Ser Gly Gly Gly Asp Gly Thr Ala Asn
        340                 345                 350 atc aag tcc cac cac aat gtt ggc ggc ctg cca gac gat gtc gaa ttc    1104
Ile Lys Ser His His Asn Val Gly Gly Leu Pro Asp Asp Val Glu Phe
    355                 360                 365 gaa ctc gtc gag cca cta cgc ctg ctg ttt aag gac gaa gtc cgt gcc    1152
Glu Leu Val Glu Pro Leu Arg Leu Leu Phe Lys Asp Glu Val Arg Ala
370                 375                 380 gtc ggc cgc gag ctc ggc ctg cct gag gaa atc gtt gcc cgc cag cca    1200
Val Gly Arg Glu Leu Gly Leu Pro Glu Glu Ile Val Ala Arg Gln Pro
385                 390                 395                 400 ttc cct ggc cct ggc cta ggc atc cgc atc atc ggt gaa gtc acc gag    1248
Phe Pro Gly Pro Gly Leu Gly Ile Arg Ile Ile Gly Glu Val Thr Glu
            405                 410                 415 gag cgt cta gaa atc ctg cgt caa gca gac ctg att gcg cgt acc gag    1296
Glu Arg Leu Glu Ile Leu Arg Gln Ala Asp Leu Ile Ala Arg Thr Glu
        420                 425                 430 ctg acc aac gct ggc ctc gac ggt gat atc tgg cag tgc cca gtc gta    1344
Leu Thr Asn Ala Gly Leu Asp Gly Asp Ile Trp Gln Cys Pro Val Val
    435                 440                 445 ctg ctt gcc gat gtc cgc tcc gtc gga gtc caa ggc gac ggc cgc acc    1392
Leu Leu Ala Asp Val Arg Ser Val Gly Val Gln Gly Asp Gly Arg Thr
450                 455                 460 tac ggc cac cca atc gtg ctg cgc cca gtg tca tcc gag gat gcc atg    1440
Tyr Gly His Pro Ile Val Leu Arg Pro Val Ser Ser Glu Asp Ala Met
465                 470                 475                 480 acc gcc gac tgg acc cgc gtt cct tac gac gtc cta gag aaa atc tcc    1488
Thr Ala Asp Trp Thr Arg Val Pro Tyr Asp Val Leu Glu Lys Ile Ser
            485                 490                 495 acc cgc att acc aac gaa gtc aac gac gtc aac cgc gtg gtc gtc gac    1536
Thr Arg Ile Thr Asn Glu Val Asn Asp Val Asn Arg Val Val Val Asp
        500                 505                 510 atc acc tcc aag cca ccg gga acc atc gag tgg gag taa                1575
Ile Thr Ser Lys Pro Pro Gly Thr Ile Glu Trp Glu
    515                 520
```

<210> SEQ ID NO 8

```
<211> LENGTH: 524
<212> TYPE: PRT
<213> ORGANISM: Corynebacterium ammoniagenes

<400> SEQUENCE: 8

Val Thr Gln Pro Ala Thr Thr Pro Arg Pro Val Leu Val Val Asp Phe
1               5                   10                  15

Gly Ala Gln Tyr Ala Gln Leu Ile Ala Arg Arg Val Arg Glu Ala Ser
                20                  25                  30

Ile Tyr Ser Glu Val Val Pro His Ser Ala Thr Val Lys Glu Ile Lys
            35                  40                  45

Ala Lys Asn Pro Ala Ala Leu Ile Leu Ser Gly Gly Pro Ser Ser Val
50                  55                  60

Tyr Ala Asp Gly Ala Pro Gln Leu Lys Pro Glu Leu Leu Glu Leu Gly
65                  70                  75                  80

Val Pro Val Phe Gly Ile Cys Tyr Gly Phe Gln Ala Met Asn His Ala
                85                  90                  95

Leu Gly Gly Asn Val Ala Gln Thr Gly Asp Arg Glu Tyr Gly Arg Thr
                100                 105                 110

Glu Ile Thr His Thr Gly Gly Val Leu His Asp Gly Leu Glu Glu Asn
            115                 120                 125

His Lys Val Trp Met Ser His Gly Asp Ala Val Asp Lys Ala Pro Glu
130                 135                 140

Gly Phe Thr Val Thr Ala Ser Ser Ala Gly Ala Pro Val Ala Ala Met
145                 150                 155                 160

Glu Cys Val Ala Lys Gln Met Ala Gly Val Gln Tyr His Pro Glu Val
                165                 170                 175

Met His Ser Pro His Gly Gln Glu Val Leu Val Arg Phe Leu Thr Glu
            180                 185                 190

Val Ala Gly Leu Glu Gln Thr Trp Thr Ser Ala Asn Ile Ala Gln Gln
        195                 200                 205

Leu Ile Asp Asp Val Arg Ala Gln Ile Gly Pro Glu Gly Arg Ala Ile
210                 215                 220

Cys Gly Leu Ser Gly Gly Val Asp Ser Ala Val Ala Ala Ala Leu Val
225                 230                 235                 240

Gln Arg Ala Ile Gly Asp Arg Leu Thr Cys Val Phe Val Asp His Gly
                245                 250                 255

Leu Leu Arg Ala Gly Glu Arg Glu Gln Val Glu Lys Asp Phe Val Ala
            260                 265                 270

Ser Thr Gly Ala Lys Leu Ile Thr Ala His Glu Ala Asp Ala Phe Leu
        275                 280                 285

Ser Lys Leu Ala Gly Val Thr Asp Pro Glu Ala Lys Arg Lys Ala Ile
290                 295                 300

Gly Ala Glu Phe Ile Arg Ser Phe Glu Arg Ala Val Ala Gln Ala Leu
305                 310                 315                 320

Glu Glu Ser Pro Glu Asp Ser Thr Val Asp Phe Leu Val Gln Gly Thr
                325                 330                 335

Leu Tyr Pro Asp Val Val Glu Ser Gly Gly Asp Gly Thr Ala Asn
            340                 345                 350

Ile Lys Ser His His Asn Val Gly Gly Leu Pro Asp Asp Val Glu Phe
        355                 360                 365

Glu Leu Val Glu Pro Leu Arg Leu Leu Phe Lys Asp Glu Val Arg Ala
370                 375                 380

Val Gly Arg Glu Leu Gly Leu Pro Glu Glu Ile Val Ala Arg Gln Pro
385                 390                 395                 400
```

```
Phe Pro Gly Pro Gly Leu Gly Ile Arg Ile Ile Gly Glu Val Thr Glu
            405                 410                 415

Glu Arg Leu Glu Ile Leu Arg Gln Ala Asp Leu Ile Ala Arg Thr Glu
        420                 425                 430

Leu Thr Asn Ala Gly Leu Asp Gly Asp Ile Trp Gln Cys Pro Val Val
            435                 440                 445

Leu Leu Ala Asp Val Arg Ser Val Gly Val Gln Gly Asp Gly Arg Thr
450                 455                 460

Tyr Gly His Pro Ile Val Leu Arg Pro Val Ser Ser Glu Asp Ala Met
465                 470                 475                 480

Thr Ala Asp Trp Thr Arg Val Pro Tyr Asp Val Leu Glu Lys Ile Ser
                485                 490                 495

Thr Arg Ile Thr Asn Glu Val Asn Asp Val Asn Arg Val Val Val Asp
            500                 505                 510

Ile Thr Ser Lys Pro Pro Gly Thr Ile Glu Trp Glu
        515                 520
```

<210> SEQ ID NO 9
<211> LENGTH: 1467
<212> TYPE: DNA
<213> ORGANISM: Escherichia coli
<220> FEATURE:
<221> NAME/KEY: CDS
<222> LOCATION: (1)..(1464)

<400> SEQUENCE: 9

```
atg cta cgt atc gct aaa gaa gct ctg acg ttt gac gac gtt ctc ctc    48
Met Leu Arg Ile Ala Lys Glu Ala Leu Thr Phe Asp Asp Val Leu Leu
1               5                   10                  15 gtt cct gct cac tct acc gtt ctg ccg aat act gct gac ctc agc acc    96
Val Pro Ala His Ser Thr Val Leu Pro Asn Thr Ala Asp Leu Ser Thr
            20                  25                  30 cag ctg acg aaa act att cgt ctg aat atc cct atg ctt tcc gca gca   144
Gln Leu Thr Lys Thr Ile Arg Leu Asn Ile Pro Met Leu Ser Ala Ala
        35                  40                  45 atg gat acc gta acg gaa gcg cgc ctg gct att gct ctg gct cag gaa   192
Met Asp Thr Val Thr Glu Ala Arg Leu Ala Ile Ala Leu Ala Gln Glu
50                  55                  60 ggc ggt atc ggc ttt atc cac aaa aac atg tcc att gaa cgc cag gca   240
Gly Gly Ile Gly Phe Ile His Lys Asn Met Ser Ile Glu Arg Gln Ala
65                  70                  75                  80 gaa gaa gtt cgc cgt gtg aaa aaa cac gaa tct ggt gtg gtg act gat   288
Glu Glu Val Arg Arg Val Lys Lys His Glu Ser Gly Val Val Thr Asp
                85                  90                  95 ccg cag act gtt ctg cca acc acg acg ctg cgc gaa gtg aaa gaa ctg   336
Pro Gln Thr Val Leu Pro Thr Thr Thr Leu Arg Glu Val Lys Glu Leu
            100                 105                 110 acc gag cgt aac ggt ttt gcg ggc tat ccg gtc gtt acc gaa gaa aac   384
Thr Glu Arg Asn Gly Phe Ala Gly Tyr Pro Val Val Thr Glu Glu Asn
        115                 120                 125 gaa ctg gtg ggt att atc acc ggt cgt gac gtg cgt ttt gtt acc gac   432
Glu Leu Val Gly Ile Ile Thr Gly Arg Asp Val Arg Phe Val Thr Asp
130                 135                 140 ctg aac cag ccg gtt agc gtt tac atg acg ccg aaa gag cgt ctg gtc   480
Leu Asn Gln Pro Val Ser Val Tyr Met Thr Pro Lys Glu Arg Leu Val
145                 150                 155                 160 acc gtg cgt gaa ggt gaa gcc cgt gaa gtg gtg ctg gca aaa atg cac   528
Thr Val Arg Glu Gly Glu Ala Arg Glu Val Val Leu Ala Lys Met His
                165                 170                 175
```

```
gaa aaa cgc gtt gaa aaa gcg ctg gtg gtt gat gac gaa ttc cac ctg      576
Glu Lys Arg Val Glu Lys Ala Leu Val Val Asp Asp Glu Phe His Leu
            180                 185                 190 atc ggc atg atc acc gtg aaa gac ttc cag aaa gcg gaa cgt aaa ccg      624
Ile Gly Met Ile Thr Val Lys Asp Phe Gln Lys Ala Glu Arg Lys Pro
        195                 200                 205 aac gcc tgt aaa gac gag caa ggc cgt ctg cgt gtt ggt gca gcg gtt      672
Asn Ala Cys Lys Asp Glu Gln Gly Arg Leu Arg Val Gly Ala Ala Val
        210                 215                 220 ggc gca ggt gcg ggt aac gaa gag cgt gtt gac gcg ctg gtt gcc gca      720
Gly Ala Gly Ala Gly Asn Glu Glu Arg Val Asp Ala Leu Val Ala Ala
225                 230                 235                 240 ggc gtt gac gtt ctg ctg atc gac tcc tcc cac ggt cac tca gaa ggt      768
Gly Val Asp Val Leu Leu Ile Asp Ser Ser His Gly His Ser Glu Gly
                245                 250                 255 gta ctg caa cgt atc cgt gaa acc cgt gct aaa tat ccg gat ctg caa      816
Val Leu Gln Arg Ile Arg Glu Thr Arg Ala Lys Tyr Pro Asp Leu Gln
            260                 265                 270 att atc ggc ggc aac gtg gca aca gct gca ggt gca cgc gct ctg gca      864
Ile Ile Gly Gly Asn Val Ala Thr Ala Ala Gly Ala Arg Ala Leu Ala
        275                 280                 285 gaa gct ggt tgc agt gcg gtt aaa gtc ggc att ggc cct ggc tct atc      912
Glu Ala Gly Cys Ser Ala Val Lys Val Gly Ile Gly Pro Gly Ser Ile
        290                 295                 300 tgt aca act cgt atc gtg act ggc gtc ggt gtt ccg cag att acc gct      960
Cys Thr Thr Arg Ile Val Thr Gly Val Gly Val Pro Gln Ile Thr Ala
305                 310                 315                 320 gtt gct gac gca gta gaa gcc ctg gaa ggc acc ggt att ccg gtt atc     1008
Val Ala Asp Ala Val Glu Ala Leu Glu Gly Thr Gly Ile Pro Val Ile
                325                 330                 335 gct gat ggc ggt att cgc ttc tcc ggc gac atc gcc aaa gct atc gcc     1056
Ala Asp Gly Gly Ile Arg Phe Ser Gly Asp Ile Ala Lys Ala Ile Ala
            340                 345                 350 gct ggc gca agc gcg gtg atg gta ggt tcc atg ctg gcg ggt act gaa     1104
Ala Gly Ala Ser Ala Val Met Val Gly Ser Met Leu Ala Gly Thr Glu
        355                 360                 365 gaa tct ccg ggt gaa atc gaa ctc tac cag ggc cgt tct tac aaa tct     1152
Glu Ser Pro Gly Glu Ile Glu Leu Tyr Gln Gly Arg Ser Tyr Lys Ser
370                 375                 380 tac cgt ggt atg ggt tcc ctg ggc gcg atg tcc aaa ggt tcc tct gac     1200
Tyr Arg Gly Met Gly Ser Leu Gly Ala Met Ser Lys Gly Ser Ser Asp
385                 390                 395                 400 cgt tat ttc cag agc gat aac gct gcc gac aaa ctg gtg ccg gaa ggt     1248
Arg Tyr Phe Gln Ser Asp Asn Ala Ala Asp Lys Leu Val Pro Glu Gly
                405                 410                 415 atc gaa ggt cgc gta gcc tat aaa ggt cgc ctg aaa gag atc att cac     1296
Ile Glu Gly Arg Val Ala Tyr Lys Gly Arg Leu Lys Glu Ile Ile His
            420                 425                 430 cag cag atg ggc ggc ctg cgc tcc tgt atg ggt ctg acc ggc tgt ggt     1344
Gln Gln Met Gly Gly Leu Arg Ser Cys Met Gly Leu Thr Gly Cys Gly
        435                 440                 445 act atc gac gaa ctg cgt act aaa gcg gag ttt gta cgt atc agc ggt     1392
Thr Ile Asp Glu Leu Arg Thr Lys Ala Glu Phe Val Arg Ile Ser Gly
        450                 455                 460 gcg ggc att cag gaa agc cac gtt cac gac gtg acc att act aaa gag     1440
Ala Gly Ile Gln Glu Ser His Val His Asp Val Thr Ile Thr Lys Glu
465                 470                 475                 480 tcc ccg aac tac cgt ctg ggc tcc tga                                 1467
Ser Pro Asn Tyr Arg Leu Gly Ser
            485
```

<210> SEQ ID NO 10
<211> LENGTH: 488
<212> TYPE: PRT
<213> ORGANISM: Escherichia coli

<400> SEQUENCE: 10

Met Leu Arg Ile Ala Lys Glu Ala Leu Thr Phe Asp Asp Val Leu Leu
1               5                   10                  15

Val Pro Ala His Ser Thr Val Leu Pro Asn Thr Ala Asp Leu Ser Thr
            20                  25                  30

Gln Leu Thr Lys Thr Ile Arg Leu Asn Ile Pro Met Leu Ser Ala Ala
        35                  40                  45

Met Asp Thr Val Thr Glu Ala Arg Leu Ala Ile Ala Leu Ala Gln Glu
50                  55                  60

Gly Gly Ile Gly Phe Ile His Lys Asn Met Ser Ile Glu Arg Gln Ala
65                  70                  75                  80

Glu Glu Val Arg Arg Val Lys Lys His Glu Ser Gly Val Val Thr Asp
                85                  90                  95

Pro Gln Thr Val Leu Pro Thr Thr Thr Leu Arg Glu Val Lys Glu Leu
            100                 105                 110

Thr Glu Arg Asn Gly Phe Ala Gly Tyr Pro Val Val Thr Glu Glu Asn
        115                 120                 125

Glu Leu Val Gly Ile Ile Thr Gly Arg Asp Val Arg Phe Val Thr Asp
130                 135                 140

Leu Asn Gln Pro Val Ser Val Tyr Met Thr Pro Lys Glu Arg Leu Val
145                 150                 155                 160

Thr Val Arg Glu Gly Glu Ala Arg Glu Val Val Leu Ala Lys Met His
                165                 170                 175

Glu Lys Arg Val Glu Lys Ala Leu Val Val Asp Asp Glu Phe His Leu
            180                 185                 190

Ile Gly Met Ile Thr Val Lys Asp Phe Gln Lys Ala Glu Arg Lys Pro
        195                 200                 205

Asn Ala Cys Lys Asp Glu Gln Gly Arg Leu Arg Val Gly Ala Ala Val
210                 215                 220

Gly Ala Gly Ala Gly Asn Glu Glu Arg Val Asp Ala Leu Val Ala Ala
225                 230                 235                 240

Gly Val Asp Val Leu Leu Ile Asp Ser Ser His Gly His Ser Glu Gly
                245                 250                 255

Val Leu Gln Arg Ile Arg Glu Thr Arg Ala Lys Tyr Pro Asp Leu Gln
            260                 265                 270

Ile Ile Gly Gly Asn Val Ala Thr Ala Ala Gly Ala Arg Ala Leu Ala
        275                 280                 285

Glu Ala Gly Cys Ser Ala Val Lys Val Gly Ile Gly Pro Gly Ser Ile
290                 295                 300

Cys Thr Thr Arg Ile Val Thr Gly Val Gly Val Pro Gln Ile Thr Ala
305                 310                 315                 320

Val Ala Asp Ala Val Glu Ala Leu Glu Gly Thr Gly Ile Pro Val Ile
                325                 330                 335

Ala Asp Gly Gly Ile Arg Phe Ser Gly Asp Ile Ala Lys Ala Ile Ala
            340                 345                 350

Ala Gly Ala Ser Ala Val Met Val Gly Ser Met Leu Ala Gly Thr Glu
        355                 360                 365

Glu Ser Pro Gly Glu Ile Glu Leu Tyr Gln Gly Arg Ser Tyr Lys Ser
370                 375                 380

```
Tyr Arg Gly Met Gly Ser Leu Gly Ala Met Ser Lys Gly Ser Ser Asp
            385                 390                 395                 400

Arg Tyr Phe Gln Ser Asp Asn Ala Ala Asp Lys Leu Val Pro Glu Gly
                    405                 410                 415

Ile Glu Gly Arg Val Ala Tyr Lys Gly Arg Leu Lys Glu Ile Ile His
                420                 425                 430

Gln Gln Met Gly Gly Leu Arg Ser Cys Met Gly Leu Thr Gly Cys Gly
            435                 440                 445

Thr Ile Asp Glu Leu Arg Thr Lys Ala Glu Phe Val Arg Ile Ser Gly
450                 455                 460

Ala Gly Ile Gln Glu Ser His Val His Asp Val Thr Ile Thr Lys Glu
465                 470                 475                 480

Ser Pro Asn Tyr Arg Leu Gly Ser
                485

<210> SEQ ID NO 11
<211> LENGTH: 1467
<212> TYPE: DNA
<213> ORGANISM: Bacillus subtilis
<220> FEATURE:
<221> NAME/KEY: CDS
<222> LOCATION: (1)..(1464)

<400> SEQUENCE: 11 atg tgg gaa agt aaa ttt tca aaa gaa ggc tta acg ttc gac gat gtg          48
Met Trp Glu Ser Lys Phe Ser Lys Glu Gly Leu Thr Phe Asp Asp Val
1               5                   10                  15 ctt ctt gta cca gca aag tct gag gta ctt ccg cgt gat gtg gat tta         96
Leu Leu Val Pro Ala Lys Ser Glu Val Leu Pro Arg Asp Val Asp Leu
            20                  25                  30 tct gta gaa ctt aca aaa acg tta aag cta aat att cct gtc atc agc        144
Ser Val Glu Leu Thr Lys Thr Leu Lys Leu Asn Ile Pro Val Ile Ser
        35                  40                  45 gca ggt atg gac act gta aca gaa tca gca atg gca att gca atg gca        192
Ala Gly Met Asp Thr Val Thr Glu Ser Ala Met Ala Ile Ala Met Ala
    50                  55                  60 aga cag ggc ggt ttg ggc atc att cac aaa aat atg tcc att gaa cag        240
Arg Gln Gly Gly Leu Gly Ile Ile His Lys Asn Met Ser Ile Glu Gln
65                  70                  75                  80 cag gct gaa caa gtt gat aaa gta aag cgt tct gag cgc ggc gtt atc        288
Gln Ala Glu Gln Val Asp Lys Val Lys Arg Ser Glu Arg Gly Val Ile
                85                  90                  95 aca aat ccc ttc ttt tta act cct gat cac caa gta ttt gat gcg gag        336
Thr Asn Pro Phe Phe Leu Thr Pro Asp His Gln Val Phe Asp Ala Glu
            100                 105                 110 cat ttg atg ggg aaa tac aga att tcc ggt gtt ccg att gta aat aac        384
His Leu Met Gly Lys Tyr Arg Ile Ser Gly Val Pro Ile Val Asn Asn
        115                 120                 125 gaa gaa gac cag aag ctt gtt gga att att aca aac cgt gac ctt cgt        432
Glu Glu Asp Gln Lys Leu Val Gly Ile Ile Thr Asn Arg Asp Leu Arg
    130                 135                 140 ttt att tct gac tac tca atg aaa atc agc gac gtc atg acg aaa gaa        480
Phe Ile Ser Asp Tyr Ser Met Lys Ile Ser Asp Val Met Thr Lys Glu
145                 150                 155                 160 gag cta gtt act gca tct gta gga act act ctg gat gaa gct gaa aag        528
Glu Leu Val Thr Ala Ser Val Gly Thr Thr Leu Asp Glu Ala Glu Lys
                165                 170                 175 att ttg cag aaa cat aaa att gaa aag ctt cct ctc gta gat gac cag        576
Ile Leu Gln Lys His Lys Ile Glu Lys Leu Pro Leu Val Asp Asp Gln
            180                 185                 190
```

```
aat aaa tta aaa ggt ctt atc aca att aaa gac att gaa aaa gtc att    624
Asn Lys Leu Lys Gly Leu Ile Thr Ile Lys Asp Ile Glu Lys Val Ile
        195                 200                 205 gag ttc ccg aac tca tct aaa gac att cac ggc cgc ctg atc gtt ggc    672
Glu Phe Pro Asn Ser Ser Lys Asp Ile His Gly Arg Leu Ile Val Gly
    210                 215                 220 gcg gca gtt ggt gta act ggc gat aca atg act cgc gtc aaa aag ctt    720
Ala Ala Val Gly Val Thr Gly Asp Thr Met Thr Arg Val Lys Lys Leu
225                 230                 235                 240 gtt gaa gcc aat gtt gat gtg att gtt atc gat aca gct cac gga cac    768
Val Glu Ala Asn Val Asp Val Ile Val Ile Asp Thr Ala His Gly His
                245                 250                 255 tct caa ggc gtt tta aac aca gtc aca aaa atc cgt gaa acg tat ccc    816
Ser Gln Gly Val Leu Asn Thr Val Thr Lys Ile Arg Glu Thr Tyr Pro
        260                 265                 270 gaa tta aac att att gct gga aac gtg gca aca gct gaa gcg aca aga    864
Glu Leu Asn Ile Ile Ala Gly Asn Val Ala Thr Ala Glu Ala Thr Arg
    275                 280                 285 gcg ctt atc gaa gct gga gca gac gtt gtc aaa gtt gga ata ggg cct    912
Ala Leu Ile Glu Ala Gly Ala Asp Val Val Lys Val Gly Ile Gly Pro
290                 295                 300 ggt tca att tgt act aca cgt gtt gta gcc ggc gtg ggt gtt ccg caa    960
Gly Ser Ile Cys Thr Thr Arg Val Val Ala Gly Val Gly Val Pro Gln
305                 310                 315                 320 att aca gca att tat gat tgt gcg act gaa gca aga aaa cac ggc aaa   1008
Ile Thr Ala Ile Tyr Asp Cys Ala Thr Glu Ala Arg Lys His Gly Lys
                325                 330                 335 aca atc atc gcc gac ggt ggg att aaa ttc tct ggc gat atc act aaa   1056
Thr Ile Ile Ala Asp Gly Gly Ile Lys Phe Ser Gly Asp Ile Thr Lys
        340                 345                 350 gca ttg gca gcc ggc gga cat gct gtt atg ctc gga agc ttg ctt gca   1104
Ala Leu Ala Ala Gly Gly His Ala Val Met Leu Gly Ser Leu Leu Ala
    355                 360                 365 ggc aca tca gaa agc cct ggt gaa act gaa atc tac caa ggc aga aga   1152
Gly Thr Ser Glu Ser Pro Gly Glu Thr Glu Ile Tyr Gln Gly Arg Arg
370                 375                 380 ttt aag gta tac cgc ggc atg gga tca gtt gct gca atg gaa aaa gga   1200
Phe Lys Val Tyr Arg Gly Met Gly Ser Val Ala Ala Met Glu Lys Gly
385                 390                 395                 400 agt aaa gac cgt tac ttc caa gaa gaa aac aaa aaa ttt gtt cct gaa   1248
Ser Lys Asp Arg Tyr Phe Gln Glu Glu Asn Lys Lys Phe Val Pro Glu
                405                 410                 415 gga att gaa gga cgc aca cct tac aaa ggg cca gtt gaa gaa acc gtt   1296
Gly Ile Glu Gly Arg Thr Pro Tyr Lys Gly Pro Val Glu Glu Thr Val
        420                 425                 430 tat cag cta gtc gga ggc ctt cgt tct ggt atg ggg tat tgc ggg tcc   1344
Tyr Gln Leu Val Gly Gly Leu Arg Ser Gly Met Gly Tyr Cys Gly Ser
    435                 440                 445 aaa gat ctg cgt gcg cta aga gaa gaa gct cag ttc att cgc atg act   1392
Lys Asp Leu Arg Ala Leu Arg Glu Glu Ala Gln Phe Ile Arg Met Thr
450                 455                 460 ggc gca gga ctt cgc gaa agc cat ccg cat gac gta cag att aca aaa   1440
Gly Ala Gly Leu Arg Glu Ser His Pro His Asp Val Gln Ile Thr Lys
465                 470                 475                 480 gaa tca cct aac tat aca att tca taa                               1467
Glu Ser Pro Asn Tyr Thr Ile Ser
                485

<210> SEQ ID NO 12
<211> LENGTH: 488
<212> TYPE: PRT
```

<213> ORGANISM: Bacillus subtilis

<400> SEQUENCE: 12

```
Met Trp Glu Ser Lys Phe Ser Lys Glu Gly Leu Thr Phe Asp Asp Val
1               5                   10                  15

Leu Leu Val Pro Ala Lys Ser Glu Val Leu Pro Arg Asp Val Asp Leu
            20                  25                  30

Ser Val Glu Leu Thr Lys Thr Leu Lys Leu Asn Ile Pro Val Ile Ser
        35                  40                  45

Ala Gly Met Asp Thr Val Thr Glu Ser Ala Met Ala Ile Ala Met Ala
50                  55                  60

Arg Gln Gly Gly Leu Gly Ile Ile His Lys Asn Met Ser Ile Glu Gln
65                  70                  75                  80

Gln Ala Glu Gln Val Asp Lys Val Lys Arg Ser Glu Arg Gly Val Ile
            85                  90                  95

Thr Asn Pro Phe Phe Leu Thr Pro Asp His Gln Val Phe Asp Ala Glu
        100                 105                 110

His Leu Met Gly Lys Tyr Arg Ile Ser Gly Val Pro Ile Val Asn Asn
    115                 120                 125

Glu Glu Asp Gln Lys Leu Val Gly Ile Ile Thr Asn Arg Asp Leu Arg
130                 135                 140

Phe Ile Ser Asp Tyr Ser Met Lys Ile Ser Asp Val Met Thr Lys Glu
145                 150                 155                 160

Glu Leu Val Thr Ala Ser Val Gly Thr Thr Leu Asp Glu Ala Glu Lys
                165                 170                 175

Ile Leu Gln Lys His Lys Ile Glu Lys Leu Pro Leu Val Asp Asp Gln
            180                 185                 190

Asn Lys Leu Lys Gly Leu Ile Thr Ile Lys Asp Ile Glu Lys Val Ile
        195                 200                 205

Glu Phe Pro Asn Ser Ser Lys Asp Ile His Gly Arg Leu Ile Val Gly
    210                 215                 220

Ala Ala Val Gly Val Thr Gly Asp Thr Met Thr Arg Val Lys Lys Leu
225                 230                 235                 240

Val Glu Ala Asn Val Asp Val Ile Val Ile Asp Thr Ala His Gly His
                245                 250                 255

Ser Gln Gly Val Leu Asn Thr Val Thr Lys Ile Arg Glu Thr Tyr Pro
            260                 265                 270

Glu Leu Asn Ile Ile Ala Gly Asn Val Ala Thr Ala Glu Ala Thr Arg
        275                 280                 285

Ala Leu Ile Glu Ala Gly Ala Asp Val Val Lys Val Gly Ile Gly Pro
    290                 295                 300

Gly Ser Ile Cys Thr Thr Arg Val Val Ala Gly Val Gly Val Pro Gln
305                 310                 315                 320

Ile Thr Ala Ile Tyr Asp Cys Ala Thr Glu Ala Arg Lys His Gly Lys
                325                 330                 335

Thr Ile Ile Ala Asp Gly Gly Ile Lys Phe Ser Gly Asp Ile Thr Lys
            340                 345                 350

Ala Leu Ala Ala Gly Gly His Ala Val Met Leu Gly Ser Leu Leu Ala
        355                 360                 365

Gly Thr Ser Glu Ser Pro Gly Glu Thr Glu Ile Tyr Gln Gly Arg Arg
    370                 375                 380

Phe Lys Val Tyr Arg Gly Met Gly Ser Val Ala Ala Met Glu Lys Gly
385                 390                 395                 400

Ser Lys Asp Arg Tyr Phe Gln Glu Glu Asn Lys Lys Phe Val Pro Glu
```

```
                       405                 410                 415
Gly Ile Glu Gly Arg Thr Pro Tyr Lys Gly Pro Val Glu Glu Thr Val
                420                 425                 430

Tyr Gln Leu Val Gly Gly Leu Arg Ser Gly Met Gly Tyr Cys Gly Ser
            435                 440                 445

Lys Asp Leu Arg Ala Leu Arg Glu Glu Ala Gln Phe Ile Arg Met Thr
        450                 455                 460

Gly Ala Gly Leu Arg Glu Ser His Pro His Asp Val Gln Ile Thr Lys
465                 470                 475                 480

Glu Ser Pro Asn Tyr Thr Ile Ser
                485

<210> SEQ ID NO 13
<211> LENGTH: 1521
<212> TYPE: DNA
<213> ORGANISM: Corynebacterium glutamicum
<220> FEATURE:
<221> NAME/KEY: CDS
<222> LOCATION: (1)..(1518)

<400> SEQUENCE: 13 atg aca acc cag agc cga gtt tct acc gga gga gac aac cca aac aag      48
Met Thr Thr Gln Ser Arg Val Ser Thr Gly Gly Asp Asn Pro Asn Lys
1               5                   10                  15 gtt gcc ctt gtt gga tta acc ttt gat gac gta ctt ttg ctt cca gat      96
Val Ala Leu Val Gly Leu Thr Phe Asp Asp Val Leu Leu Leu Pro Asp
            20                  25                  30 gcg tcg gac gtt gtt cct tca gag gta gat acc tcg acg cag tta aca     144
Ala Ser Asp Val Val Pro Ser Glu Val Asp Thr Ser Thr Gln Leu Thr
        35                  40                  45 cgt aat att cgc ctt aac acc cct att ctt tct gcc gca atg gat act     192
Arg Asn Ile Arg Leu Asn Thr Pro Ile Leu Ser Ala Ala Met Asp Thr
    50                  55                  60 gtc acc gag gct cgc atg gct atc ggc atg gca cgc cat ggc ggc att     240
Val Thr Glu Ala Arg Met Ala Ile Gly Met Ala Arg His Gly Gly Ile
65                  70                  75                  80 ggt gtt ttg cac cgc aac ctg tct att caa gag cag gca gaa aac gtt     288
Gly Val Leu His Arg Asn Leu Ser Ile Gln Glu Gln Ala Glu Asn Val
                85                  90                  95 gag ctg gtg aag cgt tct gag tct gga atg gtc act gat cct gtt acc     336
Glu Leu Val Lys Arg Ser Glu Ser Gly Met Val Thr Asp Pro Val Thr
            100                 105                 110 tgt act cct gac atg agc atc caa gaa gtg gat gat ctg tgt gca cgc     384
Cys Thr Pro Asp Met Ser Ile Gln Glu Val Asp Asp Leu Cys Ala Arg
        115                 120                 125 ttc cgc att tcc ggt ctg cct gtt gtt gat gag gcc gga aag ttg gtt     432
Phe Arg Ile Ser Gly Leu Pro Val Val Asp Glu Ala Gly Lys Leu Val
    130                 135                 140 ggt att tgc acc aac cgc gat atg cgt ttt gaa agc gac atg aac cgt     480
Gly Ile Cys Thr Asn Arg Asp Met Arg Phe Glu Ser Asp Met Asn Arg
145                 150                 155                 160 cgt gtc gct gaa gtt atg acc cca atg cct ttg gtt gtt gct gaa gag     528
Arg Val Ala Glu Val Met Thr Pro Met Pro Leu Val Val Ala Glu Glu
                165                 170                 175 ggc gtc acc aag gag cag gct ctt gct ttg ctg tct gca aac aag gtg     576
Gly Val Thr Lys Glu Gln Ala Leu Ala Leu Leu Ser Ala Asn Lys Val
            180                 185                 190 gag aag ctt cct atc atc gca aag gac ggc aag ctt gtc ggt ctg atc     624
Glu Lys Leu Pro Ile Ile Ala Lys Asp Gly Lys Leu Val Gly Leu Ile
        195                 200                 205
```

```
acg gtg aag gac ttc gtt aag act gag cag cac ccg aac gca tcc aag      672
Thr Val Lys Asp Phe Val Lys Thr Glu Gln His Pro Asn Ala Ser Lys
    210                 215                 220 gat gca tca ggt cgt ctg ctg gtt gcg gct ggc atc ggc acg ggc gag      720
Asp Ala Ser Gly Arg Leu Leu Val Ala Ala Gly Ile Gly Thr Gly Glu
225                 230                 235                 240 gag tca ttc cag cga gct ggt gcg ctt gcc gac gcc ggc gtc gac att      768
Glu Ser Phe Gln Arg Ala Gly Ala Leu Ala Asp Ala Gly Val Asp Ile
                245                 250                 255 ttg gtc gta gac tct gca cac gcc cat agc cgt gga gtt ttg gac atg      816
Leu Val Val Asp Ser Ala His Ala His Ser Arg Gly Val Leu Asp Met
            260                 265                 270 gtg tcc cgc gtg aag aag tcg ttc ccc aag gtc gat atc gtt ggc ggc      864
Val Ser Arg Val Lys Lys Ser Phe Pro Lys Val Asp Ile Val Gly Gly
        275                 280                 285 aac ttg gcg acc cgc gag gct gcg cag gcc atg att gaa gct ggc gca      912
Asn Leu Ala Thr Arg Glu Ala Ala Gln Ala Met Ile Glu Ala Gly Ala
    290                 295                 300 gac gct atc aag gtg ggt att ggc cca ggt tct att tgc acc act cgc      960
Asp Ala Ile Lys Val Gly Ile Gly Pro Gly Ser Ile Cys Thr Thr Arg
305                 310                 315                 320 gtt gtc gca ggt gtc ggt gca cct cag atc act gcg atc atg gag gca     1008
Val Val Ala Gly Val Gly Ala Pro Gln Ile Thr Ala Ile Met Glu Ala
                325                 330                 335 gct gtt cca gct cac aag gct ggc gtt cct atc atc gcc gat ggc ggc     1056
Ala Val Pro Ala His Lys Ala Gly Val Pro Ile Ile Ala Asp Gly Gly
            340                 345                 350 atg cag ttc tct ggt gat atc gct aag gct ttg gct gct ggc gct aac     1104
Met Gln Phe Ser Gly Asp Ile Ala Lys Ala Leu Ala Ala Gly Ala Asn
        355                 360                 365 tcc gtg atg ctg ggc tcc atg ctg gct ggt acc gct gag gct cct ggt     1152
Ser Val Met Leu Gly Ser Met Leu Ala Gly Thr Ala Glu Ala Pro Gly
    370                 375                 380 gag acc atc acc atc aac ggc aag cag tac aag cgt tac cgc ggc atg     1200
Glu Thr Ile Thr Ile Asn Gly Lys Gln Tyr Lys Arg Tyr Arg Gly Met
385                 390                 395                 400 ggc tcc atg ggc gct atg cag ggc cgt gga ctt agt ggt gag aag cgt     1248
Gly Ser Met Gly Ala Met Gln Gly Arg Gly Leu Ser Gly Glu Lys Arg
                405                 410                 415 tcc tac tcc aag gac cgt tac ttc cag tct gac gtt aag agc gaa gac     1296
Ser Tyr Ser Lys Asp Arg Tyr Phe Gln Ser Asp Val Lys Ser Glu Asp
            420                 425                 430 aag ctc gtt cca gaa ggc atc gaa ggt cgc gtg cct ttc cgc ggt ccc     1344
Lys Leu Val Pro Glu Gly Ile Glu Gly Arg Val Pro Phe Arg Gly Pro
        435                 440                 445 atc gga gac atc att cac cag cag gtc ggt gga ctt cgt gca gca atg     1392
Ile Gly Asp Ile Ile His Gln Gln Val Gly Gly Leu Arg Ala Ala Met
    450                 455                 460 ggc tac acc ggt tcc tcc acc att gaa gag ctg cac aac gct cgt ttc     1440
Gly Tyr Thr Gly Ser Ser Thr Ile Glu Glu Leu His Asn Ala Arg Phe
465                 470                 475                 480 gtg cag atc acc agc gcg ggt ctg aag gaa tcc cac ccg cac cac atc     1488
Val Gln Ile Thr Ser Ala Gly Leu Lys Glu Ser His Pro His His Ile
                485                 490                 495 cag cag act gtg gaa gct cct aac tac cac tag                          1521
Gln Gln Thr Val Glu Ala Pro Asn Tyr His
            500                 505

<210> SEQ ID NO 14
<211> LENGTH: 506
<212> TYPE: PRT
```

<213> ORGANISM: Corynebacterium glutamicum

<400> SEQUENCE: 14

```
Met Thr Thr Gln Ser Arg Val Ser Thr Gly Gly Asp Asn Pro Asn Lys
1               5                   10                  15

Val Ala Leu Val Gly Leu Thr Phe Asp Asp Val Leu Leu Pro Asp
            20                  25                  30

Ala Ser Asp Val Val Pro Ser Glu Val Asp Thr Ser Thr Gln Leu Thr
            35                  40                  45

Arg Asn Ile Arg Leu Asn Thr Pro Ile Leu Ser Ala Ala Met Asp Thr
        50                  55                  60

Val Thr Glu Ala Arg Met Ala Ile Gly Met Ala Arg His Gly Gly Ile
65                  70                  75                  80

Gly Val Leu His Arg Asn Leu Ser Ile Gln Glu Gln Ala Glu Asn Val
                85                  90                  95

Glu Leu Val Lys Arg Ser Glu Ser Gly Met Val Thr Asp Pro Val Thr
            100                 105                 110

Cys Thr Pro Asp Met Ser Ile Gln Glu Val Asp Asp Leu Cys Ala Arg
            115                 120                 125

Phe Arg Ile Ser Gly Leu Pro Val Val Asp Glu Ala Gly Lys Leu Val
130                 135                 140

Gly Ile Cys Thr Asn Arg Asp Met Arg Phe Glu Ser Asp Met Asn Arg
145                 150                 155                 160

Arg Val Ala Glu Val Met Thr Pro Met Pro Leu Val Val Ala Glu Glu
                165                 170                 175

Gly Val Thr Lys Glu Gln Ala Leu Ala Leu Leu Ser Ala Asn Lys Val
            180                 185                 190

Glu Lys Leu Pro Ile Ile Ala Lys Asp Gly Lys Leu Val Gly Leu Ile
            195                 200                 205

Thr Val Lys Asp Phe Val Lys Thr Glu Gln His Pro Asn Ala Ser Lys
        210                 215                 220

Asp Ala Ser Gly Arg Leu Leu Val Ala Ala Gly Ile Gly Thr Gly Glu
225                 230                 235                 240

Glu Ser Phe Gln Arg Ala Gly Ala Leu Ala Asp Ala Gly Val Asp Ile
                245                 250                 255

Leu Val Val Asp Ser Ala His Ala His Ser Arg Gly Val Leu Asp Met
            260                 265                 270

Val Ser Arg Val Lys Lys Ser Phe Pro Lys Val Asp Ile Val Gly Gly
        275                 280                 285

Asn Leu Ala Thr Arg Glu Ala Ala Gln Ala Met Ile Glu Ala Gly Ala
290                 295                 300

Asp Ala Ile Lys Val Gly Ile Gly Pro Gly Ser Ile Cys Thr Thr Arg
305                 310                 315                 320

Val Val Ala Gly Val Gly Ala Pro Gln Ile Thr Ala Ile Met Glu Ala
                325                 330                 335

Ala Val Pro Ala His Lys Ala Gly Val Pro Ile Ile Ala Asp Gly Gly
            340                 345                 350

Met Gln Phe Ser Gly Asp Ile Ala Lys Ala Leu Ala Ala Gly Ala Asn
            355                 360                 365

Ser Val Met Leu Gly Ser Met Leu Ala Gly Thr Ala Glu Ala Pro Gly
        370                 375                 380

Glu Thr Ile Thr Ile Asn Gly Lys Gln Tyr Lys Arg Tyr Arg Gly Met
385                 390                 395                 400

Gly Ser Met Gly Ala Met Gln Gly Arg Gly Leu Ser Gly Glu Lys Arg
```

```
                       405                 410                 415
Ser Tyr Ser Lys Asp Arg Tyr Phe Gln Ser Asp Val Lys Ser Glu Asp
                420                 425                 430

Lys Leu Val Pro Glu Gly Ile Glu Gly Arg Val Pro Phe Arg Gly Pro
            435                 440                 445

Ile Gly Asp Ile Ile His Gln Gln Val Gly Gly Leu Arg Ala Ala Met
        450                 455                 460

Gly Tyr Thr Gly Ser Ser Thr Ile Glu Glu Leu His Asn Ala Arg Phe
465                 470                 475                 480

Val Gln Ile Thr Ser Ala Gly Leu Lys Glu Ser His Pro His Ile
                485                 490                 495

Gln Gln Thr Val Glu Ala Pro Asn Tyr His
                500                 505

<210> SEQ ID NO 15
<211> LENGTH: 1542
<212> TYPE: DNA
<213> ORGANISM: Corynebacterium ammoniagenes
<220> FEATURE:
<221> NAME/KEY: CDS
<222> LOCATION: (1)..(1539)

<400> SEQUENCE: 15
```

| | | | | | | | | | | | | | | | | |
|---|---|---|---|---|---|---|---|---|---|---|---|---|---|---|---|---|
| gtg | cga | agg | aga | aga | ccc | gta | atg | acc | gaa | aat | cgt | gtt | tct | acc | ggt | 48 |
| Val | Arg | Arg | Arg | Arg | Pro | Val | Met | Thr | Glu | Asn | Arg | Val | Ser | Thr | Gly | |
| 1 | | | | 5 | | | | | 10 | | | | | 15 | | |
| gga | gat | gac | cca | aat | aag | gtt | gca | ttg | cat | ggc | ttg | acg | ttt | gat | gac | 96 |
| Gly | Asp | Asp | Pro | Asn | Lys | Val | Ala | Leu | His | Gly | Leu | Thr | Phe | Asp | Asp | |
| | | | 20 | | | | | 25 | | | | | 30 | | | |
| gtg | ctg | ctg | cta | cct | gcc | gaa | tcc | aat | gtt | gtt | ccg | tcg | gaa | gta | gac | 144 |
| Val | Leu | Leu | Leu | Pro | Ala | Glu | Ser | Asn | Val | Val | Pro | Ser | Glu | Val | Asp | |
| | 35 | | | | | 40 | | | | | 45 | | | | | |
| act | tcg | gcg | cag | ttc | acc | cgc | aat | act | cgt | tta | ggt | att | cct | ttg | gca | 192 |
| Thr | Ser | Ala | Gln | Phe | Thr | Arg | Asn | Thr | Arg | Leu | Gly | Ile | Pro | Leu | Ala | |
| 50 | | | | | 55 | | | | | 60 | | | | | | |
| tcg | gct | gcg | atg | gac | acg | gtt | act | gag | gcg | cgc | atg | gct | att | gcc | atg | 240 |
| Ser | Ala | Ala | Met | Asp | Thr | Val | Thr | Glu | Ala | Arg | Met | Ala | Ile | Ala | Met | |
| 65 | | | | | 70 | | | | | 75 | | | | | 80 | |
| gca | cgc | cag | ggt | ggc | att | ggt | gtc | ttg | cac | cgc | aac | ttg | tcc | tcg | caa | 288 |
| Ala | Arg | Gln | Gly | Gly | Ile | Gly | Val | Leu | His | Arg | Asn | Leu | Ser | Ser | Gln | |
| | | | | 85 | | | | | 90 | | | | | 95 | | |
| gag | cag | gcg | gag | cag | gtc | gaa | atc | gtc | aag | cgc | tct | gag | tcc | ggc | atg | 336 |
| Glu | Gln | Ala | Glu | Gln | Val | Glu | Ile | Val | Lys | Arg | Ser | Glu | Ser | Gly | Met | |
| | | | 100 | | | | | 105 | | | | | 110 | | | |
| gtc | acc | gac | cct | gtg | acc | gcg | aat | cca | gac | atg | act | atc | cag | gaa | gtt | 384 |
| Val | Thr | Asp | Pro | Val | Thr | Ala | Asn | Pro | Asp | Met | Thr | Ile | Gln | Glu | Val | |
| | 115 | | | | | 120 | | | | | 125 | | | | | |
| gat | gac | ctg | tgt | gca | cgc | ttc | cgc | atc | tct | ggt | ctt | cct | gtg | gtc | aac | 432 |
| Asp | Asp | Leu | Cys | Ala | Arg | Phe | Arg | Ile | Ser | Gly | Leu | Pro | Val | Val | Asn | |
| 130 | | | | | 135 | | | | | 140 | | | | | | |
| gaa | gac | ggc | acc | ttg | ttg | ggc | att | tgc | acc | aac | cgc | gat | atg | cgc | ttt | 480 |
| Glu | Asp | Gly | Thr | Leu | Leu | Gly | Ile | Cys | Thr | Asn | Arg | Asp | Met | Arg | Phe | |
| 145 | | | | | 150 | | | | | 155 | | | | | 160 | |
| gag | cgc | gac | tat | tcc | cgc | aag | gtt | tct | gac | atc | atg | acc | gct | atg | ccg | 528 |
| Glu | Arg | Asp | Tyr | Ser | Arg | Lys | Val | Ser | Asp | Ile | Met | Thr | Ala | Met | Pro | |
| | | | | 165 | | | | | 170 | | | | | 175 | | |
| ctg | gtt | gtg | gca | aaa | gaa | ggc | gtc | agc | aag | gaa | gaa | gcc | ctg | gat | ctg | 576 |
| Leu | Val | Val | Ala | Lys | Glu | Gly | Val | Ser | Lys | Glu | Glu | Ala | Leu | Asp | Leu | |
| | | | 180 | | | | | 185 | | | | | 190 | | | |
| ctg | tcg | acg | aac | aag | gta | gaa | aag | cta | cct | atc | gtt | gat | aaa | aac | aac | 624 |

```
Leu Ser Thr Asn Lys Val Glu Lys Leu Pro Ile Val Asp Lys Asn Asn
        195                 200                 205 aag ctg gtc ggt ctg att acc gtt aaa gac ttt gtt aag acc gaa cag      672
Lys Leu Val Gly Leu Ile Thr Val Lys Asp Phe Val Lys Thr Glu Gln
    210                 215                 220 ttc ccg aat tcc tcc aag gat gct tcg ggc cgc ttg cta gta gca gca      720
Phe Pro Asn Ser Ser Lys Asp Ala Ser Gly Arg Leu Leu Val Ala Ala
225                 230                 235                 240 ggt att ggt acc ggc gag gag tct tat gag cgt gca ggc ttg ctt gtc      768
Gly Ile Gly Thr Gly Glu Glu Ser Tyr Glu Arg Ala Gly Leu Leu Val
                245                 250                 255 gat gcc ggc gtg gac gtt ctc att gtc gac tcc gca cac gcg cac aat      816
Asp Ala Gly Val Asp Val Leu Ile Val Asp Ser Ala His Ala His Asn
            260                 265                 270 aac cgc gtg ctg gaa atg gtc tcg cgc gtc aag aat gac ttc ggc tcc      864
Asn Arg Val Leu Glu Met Val Ser Arg Val Lys Asn Asp Phe Gly Ser
        275                 280                 285 aag att gat gtt gtc ggc ggc aac ctg gca aca cgc tcg gca gca aag      912
Lys Ile Asp Val Val Gly Gly Asn Leu Ala Thr Arg Ser Ala Ala Lys
    290                 295                 300 gcg atg att gag gct ggc gca gac gcc atc aag gtg ggt att ggt cct      960
Ala Met Ile Glu Ala Gly Ala Asp Ala Ile Lys Val Gly Ile Gly Pro
305                 310                 315                 320 ggt tct atc tgc acc acc cgt gtg gtt gct ggt gtt ggt gca cca cag     1008
Gly Ser Ile Cys Thr Thr Arg Val Val Ala Gly Val Gly Ala Pro Gln
                325                 330                 335 att acc gcg atc atg gaa gca gct acc gtg gct tct gct gcg ggc gtg     1056
Ile Thr Ala Ile Met Glu Ala Ala Thr Val Ala Ser Ala Ala Gly Val
            340                 345                 350 cct ttg att gca gac ggc ggc atg cag tac tcc ggt gac gtt gct aag     1104
Pro Leu Ile Ala Asp Gly Gly Met Gln Tyr Ser Gly Asp Val Ala Lys
        355                 360                 365 gct ttg gct gct ggc gcg gac tcg gtc atg ctg ggc tcg atg ttc gca     1152
Ala Leu Ala Ala Gly Ala Asp Ser Val Met Leu Gly Ser Met Phe Ala
    370                 375                 380 ggc acc ctg gag gct cct ggt gac atc gtg att gtc ggc ggc aag cag     1200
Gly Thr Leu Glu Ala Pro Gly Asp Ile Val Ile Val Gly Gly Lys Gln
385                 390                 395                 400 tac aag cgc tac cgc ggc atg ggt tcg atg ggc gct atg caa ggc cgt     1248
Tyr Lys Arg Tyr Arg Gly Met Gly Ser Met Gly Ala Met Gln Gly Arg
                405                 410                 415 ggc ctc tcc ggc gag aag cgt tct tac tcc aag gac cgc tac ttc cag     1296
Gly Leu Ser Gly Glu Lys Arg Ser Tyr Ser Lys Asp Arg Tyr Phe Gln
            420                 425                 430 gca gat gtg cgc agc gaa gat aag ctg gtt cca gaa ggc gtg gaa ggc     1344
Ala Asp Val Arg Ser Glu Asp Lys Leu Val Pro Glu Gly Val Glu Gly
        435                 440                 445 aag gtt cct tac cgc ggc gaa att ggt cag att acc cac cag att gtg     1392
Lys Val Pro Tyr Arg Gly Glu Ile Gly Gln Ile Thr His Gln Ile Val
    450                 455                 460 ggc ggt ttg cgc gcg gca atg ggc tac act ggc tcc gct act att gaa     1440
Gly Gly Leu Arg Ala Ala Met Gly Tyr Thr Gly Ser Ala Thr Ile Glu
465                 470                 475                 480 gag ctg aag acc aag cag ttc gtg cgt att acc act gct ggc ttg gct     1488
Glu Leu Lys Thr Lys Gln Phe Val Arg Ile Thr Thr Ala Gly Leu Ala
                485                 490                 495 gag tcg cac ccg cac cac ctg cag caa act gta gaa gct ccg aac tac     1536
Glu Ser His Pro His His Leu Gln Gln Thr Val Glu Ala Pro Asn Tyr
            500                 505                 510 cgt taa                                                             1542
```

Arg

<210> SEQ ID NO 16
<211> LENGTH: 513
<212> TYPE: PRT
<213> ORGANISM: Corynebacterium ammoniagenes

<400> SEQUENCE: 16

```
Val Arg Arg Arg Pro Val Met Thr Glu Asn Arg Val Ser Thr Gly
  1               5                  10                  15

Gly Asp Asp Pro Asn Lys Val Ala Leu His Gly Leu Thr Phe Asp Asp
                 20                  25                  30

Val Leu Leu Leu Pro Ala Glu Ser Asn Val Val Pro Ser Glu Val Asp
             35                  40                  45

Thr Ser Ala Gln Phe Thr Arg Asn Thr Arg Leu Gly Ile Pro Leu Ala
         50                  55                  60

Ser Ala Ala Met Asp Thr Val Thr Glu Ala Arg Met Ala Ile Ala Met
 65                  70                  75                  80

Ala Arg Gln Gly Gly Ile Gly Val Leu His Arg Asn Leu Ser Ser Gln
                 85                  90                  95

Glu Gln Ala Glu Gln Val Glu Ile Val Lys Arg Ser Glu Ser Gly Met
            100                 105                 110

Val Thr Asp Pro Val Thr Ala Asn Pro Asp Met Thr Ile Gln Glu Val
        115                 120                 125

Asp Asp Leu Cys Ala Arg Phe Arg Ile Ser Gly Leu Pro Val Val Asn
130                 135                 140

Glu Asp Gly Thr Leu Leu Gly Ile Cys Thr Asn Arg Asp Met Arg Phe
145                 150                 155                 160

Glu Arg Asp Tyr Ser Arg Lys Val Ser Asp Ile Met Thr Ala Met Pro
                165                 170                 175

Leu Val Val Ala Lys Glu Gly Val Ser Lys Glu Glu Ala Leu Asp Leu
            180                 185                 190

Leu Ser Thr Asn Lys Val Glu Lys Leu Pro Ile Val Asp Lys Asn Asn
        195                 200                 205

Lys Leu Val Gly Leu Ile Thr Val Lys Asp Phe Val Lys Thr Glu Gln
210                 215                 220

Phe Pro Asn Ser Ser Lys Asp Ala Ser Gly Arg Leu Leu Val Ala Ala
225                 230                 235                 240

Gly Ile Gly Thr Gly Glu Glu Ser Tyr Glu Arg Ala Gly Leu Leu Val
                245                 250                 255

Asp Ala Gly Val Asp Val Leu Ile Val Asp Ser Ala His Ala His Asn
            260                 265                 270

Asn Arg Val Leu Glu Met Val Ser Arg Val Lys Asn Asp Phe Gly Ser
        275                 280                 285

Lys Ile Asp Val Val Gly Gly Asn Leu Ala Thr Arg Ser Ala Ala Lys
290                 295                 300

Ala Met Ile Glu Ala Gly Ala Asp Ala Ile Lys Val Gly Ile Gly Pro
305                 310                 315                 320

Gly Ser Ile Cys Thr Thr Arg Val Val Ala Gly Val Gly Ala Pro Gln
                325                 330                 335

Ile Thr Ala Ile Met Glu Ala Ala Thr Val Ala Ser Ala Ala Gly Val
            340                 345                 350

Pro Leu Ile Ala Asp Gly Gly Met Gln Tyr Ser Gly Asp Val Ala Lys
        355                 360                 365

Ala Leu Ala Ala Gly Ala Asp Ser Val Met Leu Gly Ser Met Phe Ala
```

```
            370               375               380
Gly Thr Leu Glu Ala Pro Gly Asp Ile Val Ile Val Gly Gly Lys Gln
385               390               395               400

Tyr Lys Arg Tyr Arg Gly Met Gly Ser Met Gly Ala Met Gln Gly Arg
            405               410               415

Gly Leu Ser Gly Glu Lys Arg Ser Tyr Ser Lys Asp Arg Tyr Phe Gln
                420               425               430

Ala Asp Val Arg Ser Glu Asp Lys Leu Val Pro Glu Gly Val Glu Gly
            435               440               445

Lys Val Pro Tyr Arg Gly Glu Ile Gly Gln Ile Thr His Gln Ile Val
        450               455               460

Gly Gly Leu Arg Ala Ala Met Gly Tyr Thr Gly Ser Ala Thr Ile Glu
465               470               475               480

Glu Leu Lys Thr Lys Gln Phe Val Arg Ile Thr Thr Ala Gly Leu Ala
                485               490               495

Glu Ser His Pro His His Leu Gln Gln Thr Val Glu Ala Pro Asn Tyr
            500               505               510

Arg

<210> SEQ ID NO 17
<211> LENGTH: 1026
<212> TYPE: DNA
<213> ORGANISM: Escherichia coli
<220> FEATURE:
<221> NAME/KEY: CDS
<222> LOCATION: (1)..(1023)

<400> SEQUENCE: 17 atg gca aca ata aaa gat gta gcg aaa cga gca aac gtt tcc act aca    48
Met Ala Thr Ile Lys Asp Val Ala Lys Arg Ala Asn Val Ser Thr Thr
1               5                  10                  15 act gtg tca cac gtg atc aac aaa aca cgt ttc gtc gct gaa gaa acg    96
Thr Val Ser His Val Ile Asn Lys Thr Arg Phe Val Ala Glu Glu Thr
            20                  25                  30 cgc aac gcc gtg tgg gca gcg att aaa gaa tta cac tac tcc cct agc   144
Arg Asn Ala Val Trp Ala Ala Ile Lys Glu Leu His Tyr Ser Pro Ser
        35                  40                  45 gcg gtg gcg cgt agc ctg aag gtt aac cac acc aag tct atc ggt ttg   192
Ala Val Ala Arg Ser Leu Lys Val Asn His Thr Lys Ser Ile Gly Leu
    50                  55                  60 ctg gcg acc agc agc gaa gcg gcc tat ttt gcc gag atc att gaa gca   240
Leu Ala Thr Ser Ser Glu Ala Ala Tyr Phe Ala Glu Ile Ile Glu Ala
65                  70                  75                  80 gtt gaa aaa aat tgc ttc cag aaa ggt tac acc ctg att ctg ggc aat   288
Val Glu Lys Asn Cys Phe Gln Lys Gly Tyr Thr Leu Ile Leu Gly Asn
                85                  90                  95 gcg tgg aac aat ctt gag aaa cag cgg gct tat ctg tcg atg atg gcg   336
Ala Trp Asn Asn Leu Glu Lys Gln Arg Ala Tyr Leu Ser Met Met Ala
            100                 105                 110 caa aaa cgc gtc gat ggt ctg ctg gtg atg tgt tct gag tac cca gag   384
Gln Lys Arg Val Asp Gly Leu Leu Val Met Cys Ser Glu Tyr Pro Glu
        115                 120                 125 ccg ttg ctg gcg atg ctg gaa gag tat cgc cat atc cca atg gtg gtc   432
Pro Leu Leu Ala Met Leu Glu Glu Tyr Arg His Ile Pro Met Val Val
    130                 135                 140 atg gac tgg ggt gaa gca aaa gct gac ttc acc gat gcg gtc att gat   480
Met Asp Trp Gly Glu Ala Lys Ala Asp Phe Thr Asp Ala Val Ile Asp
145                 150                 155                 160 aac gcg ttc gaa ggc ggc tac atg gcc ggg cgt tat ctg att gaa cgc   528
```

```
                Asn Ala Phe Glu Gly Gly Tyr Met Ala Gly Arg Tyr Leu Ile Glu Arg
                                165                 170                 175 ggt cac cgc gaa atc ggc gtc atc ccc ggc ccg ctg gaa cgt aac acc          576
Gly His Arg Glu Ile Gly Val Ile Pro Gly Pro Leu Glu Arg Asn Thr
            180                 185                 190 ggc gca ggc cgc ctt gcc ggt ttt atg aag gcg atg gaa gaa gcg atg          624
Gly Ala Gly Arg Leu Ala Gly Phe Met Lys Ala Met Glu Glu Ala Met
        195                 200                 205 atc aag gtg ccg gaa agc tgg att gtg cag ggt gac ttt gaa cct gaa          672
Ile Lys Val Pro Glu Ser Trp Ile Val Gln Gly Asp Phe Glu Pro Glu
    210                 215                 220 tcc ggt tat cgc gcc atg cag caa atc ctg tcg cag ccg cat cgc cct          720
Ser Gly Tyr Arg Ala Met Gln Gln Ile Leu Ser Gln Pro His Arg Pro
225                 230                 235                 240 act gcc gtc ttc tgt ggt ggc gat atc atg gca atg ggc gca ctt tgt          768
Thr Ala Val Phe Cys Gly Gly Asp Ile Met Ala Met Gly Ala Leu Cys
                245                 250                 255 gct gct gat gaa atg ggc ctg cgc gtc ccg cag gat gtt tcg ctg atc          816
Ala Ala Asp Glu Met Gly Leu Arg Val Pro Gln Asp Val Ser Leu Ile
            260                 265                 270 ggt tat gat aac gtg cgc aac gcg cgc tat ttt acg ccg gcg ctg acc          864
Gly Tyr Asp Asn Val Arg Asn Ala Arg Tyr Phe Thr Pro Ala Leu Thr
        275                 280                 285 acg atc cat cag cca aaa gat tcg ctg ggt gaa aca gcg ttc aac atg          912
Thr Ile His Gln Pro Lys Asp Ser Leu Gly Glu Thr Ala Phe Asn Met
    290                 295                 300 ctg ttg gat cgt atc gtc aac aaa cgt gaa gaa ccg cag tct att gaa          960
Leu Leu Asp Arg Ile Val Asn Lys Arg Glu Glu Pro Gln Ser Ile Glu
305                 310                 315                 320 gtg cat ccg cgc ttg att gaa cgc cgc tcc gtg gct gac ggc ccg ttc         1008
Val His Pro Arg Leu Ile Glu Arg Arg Ser Val Ala Asp Gly Pro Phe
                325                 330                 335 cgc gac tat cgt cgt taa                                                 1026
Arg Asp Tyr Arg Arg
            340

<210> SEQ ID NO 18
<211> LENGTH: 341
<212> TYPE: PRT
<213> ORGANISM: Escherichia coli

<400> SEQUENCE: 18

Met Ala Thr Ile Lys Asp Val Ala Lys Arg Ala Asn Val Ser Thr Thr
1               5                   10                  15

Thr Val Ser His Val Ile Asn Lys Thr Arg Phe Val Ala Glu Glu Thr
                20                  25                  30

Arg Asn Ala Val Trp Ala Ala Ile Lys Glu Leu His Tyr Ser Pro Ser
            35                  40                  45

Ala Val Ala Arg Ser Leu Lys Val Asn His Thr Lys Ser Ile Gly Leu
        50                  55                  60

Leu Ala Thr Ser Ser Glu Ala Ala Tyr Phe Ala Glu Ile Ile Glu Ala
65                  70                  75                  80

Val Glu Lys Asn Cys Phe Gln Lys Gly Tyr Thr Leu Ile Leu Gly Asn
                85                  90                  95

Ala Trp Asn Asn Leu Glu Lys Gln Arg Ala Tyr Leu Ser Met Met Ala
            100                 105                 110

Gln Lys Arg Val Asp Gly Leu Leu Val Met Cys Ser Glu Tyr Pro Glu
        115                 120                 125

Pro Leu Leu Ala Met Leu Glu Glu Tyr Arg His Ile Pro Met Val Val
```

```
                130                 135                 140
Met Asp Trp Gly Glu Ala Lys Ala Asp Phe Thr Asp Ala Val Ile Asp
145                 150                 155                 160

Asn Ala Phe Glu Gly Gly Tyr Met Ala Gly Arg Tyr Leu Ile Glu Arg
                165                 170                 175

Gly His Arg Glu Ile Gly Val Ile Pro Gly Pro Leu Glu Arg Asn Thr
            180                 185                 190

Gly Ala Gly Arg Leu Ala Gly Phe Met Lys Ala Met Glu Glu Ala Met
        195                 200                 205

Ile Lys Val Pro Glu Ser Trp Ile Val Gln Gly Asp Phe Glu Pro Glu
    210                 215                 220

Ser Gly Tyr Arg Ala Met Gln Gln Ile Leu Ser Gln Pro His Arg Pro
225                 230                 235                 240

Thr Ala Val Phe Cys Gly Gly Asp Ile Met Ala Met Gly Ala Leu Cys
                245                 250                 255

Ala Ala Asp Glu Met Gly Leu Arg Val Pro Gln Asp Val Ser Leu Ile
            260                 265                 270

Gly Tyr Asp Asn Val Arg Asn Ala Arg Tyr Phe Thr Pro Ala Leu Thr
        275                 280                 285

Thr Ile His Gln Pro Lys Asp Ser Leu Gly Glu Thr Ala Phe Asn Met
    290                 295                 300

Leu Leu Asp Arg Ile Val Asn Lys Arg Glu Glu Pro Gln Ser Ile Glu
305                 310                 315                 320

Val His Pro Arg Leu Ile Glu Arg Arg Ser Val Ala Asp Gly Pro Phe
                325                 330                 335

Arg Asp Tyr Arg Arg
            340

<210> SEQ ID NO 19
<211> LENGTH: 25
<212> TYPE: DNA
<213> ORGANISM: Artificial sequence
<220> FEATURE:
<223> OTHER INFORMATION: primer1 for cloning purR

<400> SEQUENCE: 19
ttgccatttt gctaacaaac aggaa                                    25

<210> SEQ ID NO 20
<211> LENGTH: 25
<212> TYPE: DNA
<213> ORGANISM: Artificial sequence
<220> FEATURE:
<223> OTHER INFORMATION: primer2 for cloning purR

<400> SEQUENCE: 20
tttcaggaag tgttcaacgg tgtct                                    25

<210> SEQ ID NO 21
<211> LENGTH: 1653
<212> TYPE: DNA
<213> ORGANISM: Escherichia coli
<220> FEATURE:
<221> NAME/KEY: CDS
<222> LOCATION: (1)..(1650)

<400> SEQUENCE: 21 atg aaa tta ttg cag cgg ggc gtg gcg tta gcg ctg tta acc aca ttt    48
Met Lys Leu Leu Gln Arg Gly Val Ala Leu Ala Leu Leu Thr Thr Phe
1               5                   10                  15
```

| | | |
|---|---|---|
| aca ctg gcg agt gaa act gct ctg gcg tat gag cag gat aaa acc tac<br>Thr Leu Ala Ser Glu Thr Ala Leu Ala Tyr Glu Gln Asp Lys Thr Tyr<br>20                  25                  30 | 96 | |
| aaa att aca gtt ctg cat acc aat gat cat cat ggg cat ttt tgg cgc<br>Lys Ile Thr Val Leu His Thr Asn Asp His His Gly His Phe Trp Arg<br>35                  40                  45 | 144 | |
| aat gaa tat ggc gaa tat ggt ctg gcg gcg caa aaa acg ctg gtg gat<br>Asn Glu Tyr Gly Glu Tyr Gly Leu Ala Ala Gln Lys Thr Leu Val Asp<br>50                  55                  60 | 192 | |
| ggt atc cgc aaa gag gtt gcg gct gaa ggc ggt agc gtg ctg cta ctt<br>Gly Ile Arg Lys Glu Val Ala Ala Glu Gly Gly Ser Val Leu Leu Leu<br>65                  70                  75                  80 | 240 | |
| tcc ggt ggc gac att aac act ggc gtg ccc gag tct gac tta cag gat<br>Ser Gly Gly Asp Ile Asn Thr Gly Val Pro Glu Ser Asp Leu Gln Asp<br>85                  90                  95 | 288 | |
| gcc gaa cct gat ttt cgc ggt atg aat ctg gtg ggc tat gac gcg atg<br>Ala Glu Pro Asp Phe Arg Gly Met Asn Leu Val Gly Tyr Asp Ala Met<br>100                 105                 110 | 336 | |
| gcg atc ggt aat cat gaa ttt gat aat ccg ctc acc gta tta cgc cag<br>Ala Ile Gly Asn His Glu Phe Asp Asn Pro Leu Thr Val Leu Arg Gln<br>115                 120                 125 | 384 | |
| cag gaa aag tgg gcc aag ttc ccg ttg ctt tcc gcg aat atc tac cag<br>Gln Glu Lys Trp Ala Lys Phe Pro Leu Leu Ser Ala Asn Ile Tyr Gln<br>130                 135                 140 | 432 | |
| aaa agt act ggc gag cgc ctg ttt aaa ccg tgg gcg ctg ttt aag cgt<br>Lys Ser Thr Gly Glu Arg Leu Phe Lys Pro Trp Ala Leu Phe Lys Arg<br>145                 150                 155                 160 | 480 | |
| cag gat ctg aaa att gcc gtt att ggg ctg aca acc gat gac aca gca<br>Gln Asp Leu Lys Ile Ala Val Ile Gly Leu Thr Thr Asp Asp Thr Ala<br>165                 170                 175 | 528 | |
| aaa att ggt aac ccg gaa tac ttc act gat atc gaa ttt cgt aag ccc<br>Lys Ile Gly Asn Pro Glu Tyr Phe Thr Asp Ile Glu Phe Arg Lys Pro<br>180                 185                 190 | 576 | |
| gcc gat gaa gcg aag ctg gtg att cag gag ctg caa cag aca gaa aag<br>Ala Asp Glu Ala Lys Leu Val Ile Gln Glu Leu Gln Gln Thr Glu Lys<br>195                 200                 205 | 624 | |
| cca gac att att atc gcg gcg acc cat atg ggg cat tac gat aat ggt<br>Pro Asp Ile Ile Ile Ala Ala Thr His Met Gly His Tyr Asp Asn Gly<br>210                 215                 220 | 672 | |
| gag cac ggc tct aac gca ccg ggc gat gtg gag atg gca cgc gcg ctg<br>Glu His Gly Ser Asn Ala Pro Gly Asp Val Glu Met Ala Arg Ala Leu<br>225                 230                 235                 240 | 720 | |
| cct gcc gga tcg ctg gcg atg atc gtc ggt ggt cac tcg caa gat ccg<br>Pro Ala Gly Ser Leu Ala Met Ile Val Gly Gly His Ser Gln Asp Pro<br>245                 250                 255 | 768 | |
| gtc tgc atg gcg gca gaa aac aaa aaa cag gtc gat tac gtg ccg ggt<br>Val Cys Met Ala Ala Glu Asn Lys Lys Gln Val Asp Tyr Val Pro Gly<br>260                 265                 270 | 816 | |
| acg cca tgc aaa cca gat caa caa aac ggc atc tgg att gtg cag gcg<br>Thr Pro Cys Lys Pro Asp Gln Gln Asn Gly Ile Trp Ile Val Gln Ala<br>275                 280                 285 | 864 | |
| cat gag tgg ggc aaa tac gtg gga cgg gct gat ttt gag ttt cgt aat<br>His Glu Trp Gly Lys Tyr Val Gly Arg Ala Asp Phe Glu Phe Arg Asn<br>290                 295                 300 | 912 | |
| ggc gaa atg aaa atg gtt aac tac cag ctg att ccg gtg aac ctg aag<br>Gly Glu Met Lys Met Val Asn Tyr Gln Leu Ile Pro Val Asn Leu Lys<br>305                 310                 315                 320 | 960 | |
| aag aaa gtg acc tgg gaa gac ggg aaa agc gag cgc gtg ctt tac act<br>Lys Lys Val Thr Trp Glu Asp Gly Lys Ser Glu Arg Val Leu Tyr Thr<br>325                 330                 335 | 1008 | |

| | | | | | | | | | | | | | | | | |
|---|---|---|---|---|---|---|---|---|---|---|---|---|---|---|---|---|
| cct | gaa | atc | gct | gaa | aac | cag | caa | atg | atc | tcg | ctg | tta | tca | ccg | ttc | 1056 |
| Pro | Glu | Ile | Ala | Glu | Asn | Gln | Gln | Met | Ile | Ser | Leu | Leu | Ser | Pro | Phe | |
| | | | 340 | | | | | 345 | | | | | 350 | | | |
| cag | aac | aaa | ggc | aaa | gcg | cag | ctg | gaa | gtg | aaa | ata | ggc | gaa | acc | aat | 1104 |
| Gln | Asn | Lys | Gly | Lys | Ala | Gln | Leu | Glu | Val | Lys | Ile | Gly | Glu | Thr | Asn | |
| | | 355 | | | | | 360 | | | | | 365 | | | | |
| ggt | cgt | ctg | gaa | ggc | gat | cgt | gac | aaa | gtg | cgt | ttt | gta | cag | acc | aat | 1152 |
| Gly | Arg | Leu | Glu | Gly | Asp | Arg | Asp | Lys | Val | Arg | Phe | Val | Gln | Thr | Asn | |
| | 370 | | | | | 375 | | | | | 380 | | | | | |
| atg | ggg | cgg | ttg | att | ctg | gca | gcc | caa | atg | gat | cgc | act | ggt | gcc | gac | 1200 |
| Met | Gly | Arg | Leu | Ile | Leu | Ala | Ala | Gln | Met | Asp | Arg | Thr | Gly | Ala | Asp | |
| 385 | | | | | 390 | | | | | 395 | | | | | 400 | |
| ttt | gcg | gtg | atg | agc | gga | ggc | gga | att | cgt | gat | tct | atc | gaa | gca | ggc | 1248 |
| Phe | Ala | Val | Met | Ser | Gly | Gly | Gly | Ile | Arg | Asp | Ser | Ile | Glu | Ala | Gly | |
| | | | | 405 | | | | | 410 | | | | | 415 | | |
| gat | atc | agc | tat | aaa | aac | gtg | ctg | aaa | gtg | cag | cca | ttc | ggc | aat | gtg | 1296 |
| Asp | Ile | Ser | Tyr | Lys | Asn | Val | Leu | Lys | Val | Gln | Pro | Phe | Gly | Asn | Val | |
| | | | 420 | | | | | 425 | | | | | 430 | | | |
| gtg | tat | gcc | gac | atg | acc | ggt | aaa | gag | gtg | att | gat | tac | ctg | acc | | 1344 |
| Val | Val | Tyr | Ala | Asp | Met | Thr | Gly | Lys | Glu | Val | Ile | Asp | Tyr | Leu | Thr | |
| | | 435 | | | | | 440 | | | | | 445 | | | | |
| gcc | gtc | gcg | cag | atg | aag | cca | gat | tca | ggt | gcc | tac | ccg | caa | ttt | gcc | 1392 |
| Ala | Val | Ala | Gln | Met | Lys | Pro | Asp | Ser | Gly | Ala | Tyr | Pro | Gln | Phe | Ala | |
| | 450 | | | | | 455 | | | | | 460 | | | | | |
| aac | gtt | agc | ttt | gtg | gcg | aaa | gac | ggc | aaa | ctg | aac | gac | ctt | aaa | atc | 1440 |
| Asn | Val | Ser | Phe | Val | Ala | Lys | Asp | Gly | Lys | Leu | Asn | Asp | Leu | Lys | Ile | |
| 465 | | | | | 470 | | | | | 475 | | | | | 480 | |
| aaa | ggc | gaa | ccg | gtc | gat | ccg | gcg | aaa | act | tac | cgt | atg | gcg | aca | tta | 1488 |
| Lys | Gly | Glu | Pro | Val | Asp | Pro | Ala | Lys | Thr | Tyr | Arg | Met | Ala | Thr | Leu | |
| | | | | 485 | | | | | 490 | | | | | 495 | | |
| aac | ttc | aat | gcc | acc | ggc | ggt | gat | gga | tat | ccg | cgc | ctt | gat | aac | aaa | 1536 |
| Asn | Phe | Asn | Ala | Thr | Gly | Gly | Asp | Gly | Tyr | Pro | Arg | Leu | Asp | Asn | Lys | |
| | | | 500 | | | | | 505 | | | | | 510 | | | |
| ccg | ggc | tat | gtg | aat | acc | ggc | ttt | att | gat | gcc | gaa | gtg | ctg | aaa | gcg | 1584 |
| Pro | Gly | Tyr | Val | Asn | Thr | Gly | Phe | Ile | Asp | Ala | Glu | Val | Leu | Lys | Ala | |
| | | 515 | | | | | 520 | | | | | 525 | | | | |
| tat | atc | cag | aaa | agc | tcg | ccg | ctg | gat | gtg | agt | gtt | tat | gaa | ccg | aaa | 1632 |
| Tyr | Ile | Gln | Lys | Ser | Ser | Pro | Leu | Asp | Val | Ser | Val | Tyr | Glu | Pro | Lys | |
| | 530 | | | | | 535 | | | | | 540 | | | | | |
| ggt | gag | gtg | agc | tgg | cag | taa | | | | | | | | | | 1653 |
| Gly | Glu | Val | Ser | Trp | Gln | | | | | | | | | | | |
| 545 | | | | | 550 | | | | | | | | | | | |

<210> SEQ ID NO 22
<211> LENGTH: 550
<212> TYPE: PRT
<213> ORGANISM: Escherichia coli

<400> SEQUENCE: 22

Met Lys Leu Leu Gln Arg Gly Val Ala Leu Ala Leu Leu Thr Thr Phe
1               5                   10                  15

Thr Leu Ala Ser Glu Thr Ala Leu Ala Tyr Glu Gln Asp Lys Thr Tyr
                20                  25                  30

Lys Ile Thr Val Leu His Thr Asn Asp His His Gly His Phe Trp Arg
            35                  40                  45

Asn Glu Tyr Gly Glu Tyr Gly Leu Ala Ala Gln Lys Thr Leu Val Asp
        50                  55                  60

Gly Ile Arg Lys Glu Val Ala Ala Glu Gly Gly Ser Val Leu Leu Leu
65                  70                  75                  80

Ser Gly Gly Asp Ile Asn Thr Gly Val Pro Glu Ser Asp Leu Gln Asp

```
                 85                  90                  95
Ala Glu Pro Asp Phe Arg Gly Met Asn Leu Val Gly Tyr Asp Ala Met
            100                 105                 110

Ala Ile Gly Asn His Glu Phe Asp Asn Pro Leu Thr Val Leu Arg Gln
        115                 120                 125

Gln Glu Lys Trp Ala Lys Phe Pro Leu Leu Ser Ala Asn Ile Tyr Gln
    130                 135                 140

Lys Ser Thr Gly Glu Arg Leu Phe Lys Pro Trp Ala Leu Phe Lys Arg
145                 150                 155                 160

Gln Asp Leu Lys Ile Ala Val Ile Gly Leu Thr Thr Asp Asp Thr Ala
                165                 170                 175

Lys Ile Gly Asn Pro Glu Tyr Phe Thr Asp Ile Glu Phe Arg Lys Pro
            180                 185                 190

Ala Asp Glu Ala Lys Leu Val Ile Gln Glu Leu Gln Gln Thr Glu Lys
        195                 200                 205

Pro Asp Ile Ile Ile Ala Ala Thr His Met Gly His Tyr Asp Asn Gly
    210                 215                 220

Glu His Gly Ser Asn Ala Pro Gly Asp Val Glu Met Ala Arg Ala Leu
225                 230                 235                 240

Pro Ala Gly Ser Leu Ala Met Ile Val Gly Gly His Ser Gln Asp Pro
                245                 250                 255

Val Cys Met Ala Ala Glu Asn Lys Lys Gln Val Asp Tyr Val Pro Gly
            260                 265                 270

Thr Pro Cys Lys Pro Asp Gln Gln Asn Gly Ile Trp Ile Val Gln Ala
        275                 280                 285

His Glu Trp Gly Lys Tyr Val Gly Arg Ala Asp Phe Glu Phe Arg Asn
    290                 295                 300

Gly Glu Met Lys Met Val Asn Tyr Gln Leu Ile Pro Val Asn Leu Lys
305                 310                 315                 320

Lys Lys Val Thr Trp Glu Asp Gly Lys Ser Glu Arg Val Leu Tyr Thr
                325                 330                 335

Pro Glu Ile Ala Glu Asn Gln Gln Met Ile Ser Leu Leu Ser Pro Phe
            340                 345                 350

Gln Asn Lys Gly Lys Ala Gln Leu Glu Val Lys Ile Gly Glu Thr Asn
        355                 360                 365

Gly Arg Leu Glu Gly Asp Arg Asp Lys Val Arg Phe Val Gln Thr Asn
    370                 375                 380

Met Gly Arg Leu Ile Leu Ala Ala Gln Met Asp Arg Thr Gly Ala Asp
385                 390                 395                 400

Phe Ala Val Met Ser Gly Gly Gly Ile Arg Asp Ser Ile Glu Ala Gly
                405                 410                 415

Asp Ile Ser Tyr Lys Asn Val Leu Lys Val Gln Pro Phe Gly Asn Val
            420                 425                 430

Val Val Tyr Ala Asp Met Thr Gly Lys Glu Val Ile Asp Tyr Leu Thr
        435                 440                 445

Ala Val Ala Gln Met Lys Pro Asp Ser Gly Ala Tyr Pro Gln Phe Ala
    450                 455                 460

Asn Val Ser Phe Val Ala Lys Asp Gly Lys Leu Asn Asp Leu Lys Ile
465                 470                 475                 480

Lys Gly Glu Pro Val Asp Pro Ala Lys Thr Tyr Arg Met Ala Thr Leu
                485                 490                 495

Asn Phe Asn Ala Thr Gly Gly Asp Gly Tyr Pro Arg Leu Asp Asn Lys
            500                 505                 510
```

```
Pro Gly Tyr Val Asn Thr Gly Phe Ile Asp Ala Glu Val Leu Lys Ala
        515                 520                 525

Tyr Ile Gln Lys Ser Ser Pro Leu Asp Val Ser Val Tyr Glu Pro Lys
    530                 535                 540

Gly Glu Val Ser Trp Gln
545                 550

<210> SEQ ID NO 23
<211> LENGTH: 714
<212> TYPE: DNA
<213> ORGANISM: Escherichia coli
<220> FEATURE:
<221> NAME/KEY: CDS
<222> LOCATION: (1)..(711)

<400> SEQUENCE: 23 atg cgc aag atc aca cag gca atc agt gcc gtt tgc tta ttg ttc gct      48
Met Arg Lys Ile Thr Gln Ala Ile Ser Ala Val Cys Leu Leu Phe Ala
1               5                   10                  15 cta aac agt tcc gct gtt gcc ctg gcc tca tct cct tca ccg ctt aac      96
Leu Asn Ser Ser Ala Val Ala Leu Ala Ser Ser Pro Ser Pro Leu Asn
            20                  25                  30 cct ggg act aac gtt gcc agg ctt gct gaa cag gca ccc att cat tgg     144
Pro Gly Thr Asn Val Ala Arg Leu Ala Glu Gln Ala Pro Ile His Trp
        35                  40                  45 gtt tcg gtc gca caa att gaa aat agc ctc gca ggg cgt ccg cca atg     192
Val Ser Val Ala Gln Ile Glu Asn Ser Leu Ala Gly Arg Pro Pro Met
    50                  55                  60 gcg gtg ggg ttt gat atc gat gac acg gta ctt ttt tcc agt ccg ggc     240
Ala Val Gly Phe Asp Ile Asp Asp Thr Val Leu Phe Ser Ser Pro Gly
65                  70                  75                  80 ttc tgg cgc ggc aaa aaa acc ttc tcg cca gaa agc gaa gat tat ctg     288
Phe Trp Arg Gly Lys Lys Thr Phe Ser Pro Glu Ser Glu Asp Tyr Leu
                85                  90                  95 aaa aat cct gtg ttc tgg gaa aaa atg aac aat ggc tgg gat gaa ttc     336
Lys Asn Pro Val Phe Trp Glu Lys Met Asn Asn Gly Trp Asp Glu Phe
            100                 105                 110 agc att cca aaa gag gtc gct cgc cag ctg att gat atg cat gta cgc     384
Ser Ile Pro Lys Glu Val Ala Arg Gln Leu Ile Asp Met His Val Arg
        115                 120                 125 cgc ggt gac gcg atc ttc ttt gtg act ggt cgt agc ccg acg aaa aca     432
Arg Gly Asp Ala Ile Phe Phe Val Thr Gly Arg Ser Pro Thr Lys Thr
    130                 135                 140 gaa acg gtt tca aaa acg ctg gcg gat aat ttt cat att cct gcc acc     480
Glu Thr Val Ser Lys Thr Leu Ala Asp Asn Phe His Ile Pro Ala Thr
145                 150                 155                 160 aac atg aat ccg gtg atc ttt gcg ggc gat aaa cca ggg caa aat aca     528
Asn Met Asn Pro Val Ile Phe Ala Gly Asp Lys Pro Gly Gln Asn Thr
                165                 170                 175 aaa tcg caa tgg ctg cag gat aaa aat atc cga att ttt tat ggc gat     576
Lys Ser Gln Trp Leu Gln Asp Lys Asn Ile Arg Ile Phe Tyr Gly Asp
            180                 185                 190 tct gat aat gat att acc gcc gca cgc gat gtc ggc gct cgt ggt atc     624
Ser Asp Asn Asp Ile Thr Ala Ala Arg Asp Val Gly Ala Arg Gly Ile
        195                 200                 205 cgc att ctg cgc gcc tcc aac tct acc tac aaa ccc ttg cca caa gcg     672
Arg Ile Leu Arg Ala Ser Asn Ser Thr Tyr Lys Pro Leu Pro Gln Ala
    210                 215                 220 ggt gcg ttt ggt gaa gag gtg atc gtc aat tca gaa tac tga             714
Gly Ala Phe Gly Glu Glu Val Ile Val Asn Ser Glu Tyr
225                 230                 235
```

```
<210> SEQ ID NO 24
<211> LENGTH: 237
<212> TYPE: PRT
<213> ORGANISM: Escherichia coli

<400> SEQUENCE: 24

Met Arg Lys Ile Thr Gln Ala Ile Ser Ala Val Cys Leu Leu Phe Ala
1               5                   10                  15

Leu Asn Ser Ser Ala Val Ala Leu Ala Ser Ser Pro Ser Pro Leu Asn
            20                  25                  30

Pro Gly Thr Asn Val Ala Arg Leu Ala Glu Gln Ala Pro Ile His Trp
        35                  40                  45

Val Ser Val Ala Gln Ile Glu Asn Ser Leu Ala Gly Arg Pro Pro Met
    50                  55                  60

Ala Val Gly Phe Asp Ile Asp Asp Thr Val Leu Phe Ser Ser Pro Gly
65                  70                  75                  80

Phe Trp Arg Gly Lys Lys Thr Phe Ser Pro Glu Ser Glu Asp Tyr Leu
                85                  90                  95

Lys Asn Pro Val Phe Trp Glu Lys Met Asn Asn Gly Trp Asp Glu Phe
            100                 105                 110

Ser Ile Pro Lys Glu Val Ala Arg Gln Leu Ile Asp Met His Val Arg
        115                 120                 125

Arg Gly Asp Ala Ile Phe Phe Val Thr Gly Arg Ser Pro Thr Lys Thr
    130                 135                 140

Glu Thr Val Ser Lys Thr Leu Ala Asp Asn Phe His Ile Pro Ala Thr
145                 150                 155                 160

Asn Met Asn Pro Val Ile Phe Ala Gly Asp Lys Pro Gly Gln Asn Thr
                165                 170                 175

Lys Ser Gln Trp Leu Gln Asp Lys Asn Ile Arg Ile Phe Tyr Gly Asp
            180                 185                 190

Ser Asp Asn Asp Ile Thr Ala Ala Arg Asp Val Gly Ala Arg Gly Ile
        195                 200                 205

Arg Ile Leu Arg Ala Ser Asn Ser Thr Tyr Lys Pro Leu Pro Gln Ala
    210                 215                 220

Gly Ala Phe Gly Glu Glu Val Ile Val Asn Ser Glu Tyr
225                 230                 235

<210> SEQ ID NO 25
<211> LENGTH: 54
<212> TYPE: DNA
<213> ORGANISM: Artificial sequence
<220> FEATURE:
<223> OTHER INFORMATION: primer1 for disrupting ushA

<400> SEQUENCE: 25
ggagagaagt atgaaattat tgcagcgggg cgtggccgct caagttagta taaa          54

<210> SEQ ID NO 26
<211> LENGTH: 54
<212> TYPE: DNA
<213> ORGANISM: Artificial sequence
<220> FEATURE:
<223> OTHER INFORMATION: primer2 for disrupting ushA

<400> SEQUENCE: 26
ccagctcacc tcacctttcg gttcataaac actcactgaa gcctgctttt ttat          54

<210> SEQ ID NO 27
<211> LENGTH: 54
```

```
<212> TYPE: DNA
<213> ORGANISM: Artificial sequence
<220> FEATURE:
<223> OTHER INFORMATION: primer1 for disrupting aphA

<400> SEQUENCE: 27
agggaaaaat atgcgcaaga tcacacaggc aatcagcgct caagttagta taaa          54

<210> SEQ ID NO 28
<211> LENGTH: 54
<212> TYPE: DNA
<213> ORGANISM: Artificial sequence
<220> FEATURE:
<223> OTHER INFORMATION: primer2 for disrupting aphA

<400> SEQUENCE: 28
ttctgaattg acgatcacct cttcaccaaa cgcacctgaa gcctgctttt ttat          54

<210> SEQ ID NO 29
<211> LENGTH: 54
<212> TYPE: DNA
<213> ORGANISM: Artificial sequence
<220> FEATURE:
<223> OTHER INFORMATION: primer1 for disrupting purR

<400> SEQUENCE: 29
gtgaaatgga atggcaacaa taaaagatgt agcgaacgct caagttagta taaa          54

<210> SEQ ID NO 30
<211> LENGTH: 54
<212> TYPE: DNA
<213> ORGANISM: Artificial sequence
<220> FEATURE:
<223> OTHER INFORMATION: primer2 for disrupting purR

<400> SEQUENCE: 30
acgatagtcg cggaacgggc cgtcagccac ggagcgtgaa gcctgctttt ttat          54

<210> SEQ ID NO 31
<211> LENGTH: 29
<212> TYPE: DNA
<213> ORGANISM: Artificial sequence
<220> FEATURE:
<223> OTHER INFORMATION: primer1 for cloning guaBA

<400> SEQUENCE: 31
cgcgagctct attcagtcga tagtaaccc                                       29

<210> SEQ ID NO 32
<211> LENGTH: 29
<212> TYPE: DNA
<213> ORGANISM: Artificial sequence
<220> FEATURE:
<223> OTHER INFORMATION: primer2 for cloning guaBA

<400> SEQUENCE: 32
cgcggtacct caatcctata attcttgaa                                       29

<210> SEQ ID NO 33
<211> LENGTH: 1299
<212> TYPE: DNA
<213> ORGANISM: Escherichia coli
<220> FEATURE:
<221> NAME/KEY: CDS
<222> LOCATION: (1)..(1296)

<400> SEQUENCE: 33
```

```
atg ggt aac aac gtc gtc gta ctg ggc acc caa tgg ggt gac gaa ggt      48
Met Gly Asn Asn Val Val Val Leu Gly Thr Gln Trp Gly Asp Glu Gly
1               5                  10                  15 aaa ggt aag atc gtc gat ctt ctg act gaa cgg gct aaa tat gtt gta      96
Lys Gly Lys Ile Val Asp Leu Leu Thr Glu Arg Ala Lys Tyr Val Val
            20                  25                  30 cgc tac cag ggc ggt cac aac gca ggc cat act ctc gta atc aac ggt     144
Arg Tyr Gln Gly Gly His Asn Ala Gly His Thr Leu Val Ile Asn Gly
        35                  40                  45 gaa aaa acc gtt ctc cat ctt att cca tca ggt att ctc cgc gag aat     192
Glu Lys Thr Val Leu His Leu Ile Pro Ser Gly Ile Leu Arg Glu Asn
    50                  55                  60 gta acc agc atc atc ggt aac ggt gtt gtg ctg tct ccg gcc gcg ctg     240
Val Thr Ser Ile Ile Gly Asn Gly Val Val Leu Ser Pro Ala Ala Leu
65                  70                  75                  80 atg aaa gag atg aaa gaa ctg gaa gac cgt ggc atc ccc gtt cgt gag     288
Met Lys Glu Met Lys Glu Leu Glu Asp Arg Gly Ile Pro Val Arg Glu
                85                  90                  95 cgt ctg ctg ctg tct gaa gca tgt ccg ctg atc ctt gat tat cac gtt     336
Arg Leu Leu Leu Ser Glu Ala Cys Pro Leu Ile Leu Asp Tyr His Val
            100                 105                 110 gcg ctg gat aac gcg cgt gag aaa gcg cgt ggc gcg aaa gcg atc ggc     384
Ala Leu Asp Asn Ala Arg Glu Lys Ala Arg Gly Ala Lys Ala Ile Gly
        115                 120                 125 acc acc ggt cgt ggt atc ggg cct gct tat gaa gat aaa gta gca cgt     432
Thr Thr Gly Arg Gly Ile Gly Pro Ala Tyr Glu Asp Lys Val Ala Arg
    130                 135                 140 cgc ggt ctg cgt gtt ggc gac ctt ttc gac aaa gaa acc ttc gct gaa     480
Arg Gly Leu Arg Val Gly Asp Leu Phe Asp Lys Glu Thr Phe Ala Glu
145                 150                 155                 160 aaa ctg aaa gaa gtg atg gaa tat cac aac ttc cag ttg gtt aac tac     528
Lys Leu Lys Glu Val Met Glu Tyr His Asn Phe Gln Leu Val Asn Tyr
                165                 170                 175 tac aaa gct gaa gcg gtt gat tac cag aaa gtt ctg gat gat acg atg     576
Tyr Lys Ala Glu Ala Val Asp Tyr Gln Lys Val Leu Asp Asp Thr Met
            180                 185                 190 gct gtt gcc gac atc ctg act tct atg gtg gtt gac gtt tct gac ctg     624
Ala Val Ala Asp Ile Leu Thr Ser Met Val Val Asp Val Ser Asp Leu
        195                 200                 205 ctc gac cag gcg cgt cag cgt ggc gat ttc gtc atg ttt gaa ggt gcg     672
Leu Asp Gln Ala Arg Gln Arg Gly Asp Phe Val Met Phe Glu Gly Ala
    210                 215                 220 cag ggt acg ctg ctg gat atc gac cac ggt act tat ccg tac gta act     720
Gln Gly Thr Leu Leu Asp Ile Asp His Gly Thr Tyr Pro Tyr Val Thr
225                 230                 235                 240 tct tcc aac acc act gct ggt ggc gtg gcg acc ggt tcc ggc ctg ggc     768
Ser Ser Asn Thr Thr Ala Gly Gly Val Ala Thr Gly Ser Gly Leu Gly
                245                 250                 255 ccg cgt tat gtt gat tac gtt ctg ggt atc ctc aaa gct tac tcc act     816
Pro Arg Tyr Val Asp Tyr Val Leu Gly Ile Leu Lys Ala Tyr Ser Thr
            260                 265                 270 cgt gta ggt gca ggt ccg ttc ccg acc gaa ctg ttt gat gaa act ggc     864
Arg Val Gly Ala Gly Pro Phe Pro Thr Glu Leu Phe Asp Glu Thr Gly
        275                 280                 285 gag ttc ctc tgc aag cag ggt aac gaa ttc ggc gca act acg ggg cgt     912
Glu Phe Leu Cys Lys Gln Gly Asn Glu Phe Gly Ala Thr Thr Gly Arg
    290                 295                 300 cgt cgt cgt acc ggc tgg ctg gac acc gtt gcc gtt cgt cgt gcg gta     960
Arg Arg Arg Thr Gly Trp Leu Asp Thr Val Ala Val Arg Arg Ala Val
305                 310                 315                 320
```

```
cag ctg aac tcc ctg tct ggc ttc tgc ctg act aaa ctg gac gtt ctg    1008
Gln Leu Asn Ser Leu Ser Gly Phe Cys Leu Thr Lys Leu Asp Val Leu
            325                 330                 335 gat ggc ctg aaa gag gtt aaa ctc tgc gtg gct tac cgt atg ccg gat    1056
Asp Gly Leu Lys Glu Val Lys Leu Cys Val Ala Tyr Arg Met Pro Asp
        340                 345                 350 ggt cgc gaa gtg act acc act ccg ctg gca gct gac gac tgg aaa ggt    1104
Gly Arg Glu Val Thr Thr Thr Pro Leu Ala Ala Asp Asp Trp Lys Gly
    355                 360                 365 gta gag ccg att tac gaa acc atg ccg ggc tgg tct gaa tcc acc ttc    1152
Val Glu Pro Ile Tyr Glu Thr Met Pro Gly Trp Ser Glu Ser Thr Phe
370                 375                 380 ggc gtg aaa gat cgt agc ggc ctg ccg cag gcg gcg ctg aac tat atc    1200
Gly Val Lys Asp Arg Ser Gly Leu Pro Gln Ala Ala Leu Asn Tyr Ile
385                 390                 395                 400 aag cgt att gaa gag ctg act ggt gtg ccg atc gat atc tct acc        1248
Lys Arg Ile Glu Glu Leu Thr Gly Val Pro Ile Asp Ile Ile Ser Thr
            405                 410                 415 ggt ccg gat cgt act gaa acc atg att ctg cgc gac ccg ttc gac gcg    1296
Gly Pro Asp Arg Thr Glu Thr Met Ile Leu Arg Asp Pro Phe Asp Ala
        420                 425                 430 taa                                                                1299

<210> SEQ ID NO 34
<211> LENGTH: 432
<212> TYPE: PRT
<213> ORGANISM: Escherichia coli

<400> SEQUENCE: 34

Met Gly Asn Asn Val Val Leu Gly Thr Gln Trp Gly Asp Glu Gly
1               5                   10                  15

Lys Gly Lys Ile Val Asp Leu Leu Thr Glu Arg Ala Lys Tyr Val Val
            20                  25                  30

Arg Tyr Gln Gly Gly His Asn Ala Gly His Thr Leu Val Ile Asn Gly
        35                  40                  45

Glu Lys Thr Val Leu His Leu Ile Pro Ser Gly Ile Leu Arg Glu Asn
    50                  55                  60

Val Thr Ser Ile Ile Gly Asn Gly Val Val Leu Ser Pro Ala Ala Leu
65                  70                  75                  80

Met Lys Glu Met Lys Glu Leu Glu Asp Arg Gly Ile Pro Val Arg Glu
            85                  90                  95

Arg Leu Leu Leu Ser Glu Ala Cys Pro Leu Ile Leu Asp Tyr His Val
        100                 105                 110

Ala Leu Asp Asn Ala Arg Glu Lys Ala Arg Gly Ala Lys Ala Ile Gly
    115                 120                 125

Thr Thr Gly Arg Gly Ile Gly Pro Ala Tyr Glu Asp Lys Val Ala Arg
130                 135                 140

Arg Gly Leu Arg Val Gly Asp Leu Phe Asp Lys Glu Thr Phe Ala Glu
145                 150                 155                 160

Lys Leu Lys Glu Val Met Glu Tyr His Asn Phe Gln Leu Val Asn Tyr
            165                 170                 175

Tyr Lys Ala Glu Ala Val Asp Tyr Gln Lys Val Leu Asp Asp Thr Met
        180                 185                 190

Ala Val Ala Asp Ile Leu Thr Ser Met Val Val Asp Val Ser Asp Leu
    195                 200                 205

Leu Asp Gln Ala Arg Gln Arg Gly Asp Phe Val Met Phe Glu Gly Ala
    210                 215                 220
```

```
Gln Gly Thr Leu Leu Asp Ile Asp His Gly Thr Tyr Pro Tyr Val Thr
225                 230                 235                 240

Ser Ser Asn Thr Thr Ala Gly Val Ala Thr Gly Ser Gly Leu Gly
            245                 250                 255

Pro Arg Tyr Val Asp Tyr Val Leu Gly Ile Leu Lys Ala Tyr Ser Thr
                260                 265                 270

Arg Val Gly Ala Gly Pro Phe Pro Thr Glu Leu Phe Asp Glu Thr Gly
            275                 280                 285

Glu Phe Leu Cys Lys Gln Gly Asn Glu Phe Gly Ala Thr Thr Gly Arg
    290                 295                 300

Arg Arg Arg Thr Gly Trp Leu Asp Thr Val Ala Val Arg Ala Val
305                 310                 315                 320

Gln Leu Asn Ser Leu Ser Gly Phe Cys Leu Thr Lys Leu Asp Val Leu
                325                 330                 335

Asp Gly Leu Lys Glu Val Lys Leu Cys Val Ala Tyr Arg Met Pro Asp
            340                 345                 350

Gly Arg Glu Val Thr Thr Thr Pro Leu Ala Ala Asp Asp Trp Lys Gly
    355                 360                 365

Val Glu Pro Ile Tyr Glu Thr Met Pro Gly Trp Ser Glu Ser Thr Phe
370                 375                 380

Gly Val Lys Asp Arg Ser Gly Leu Pro Gln Ala Ala Leu Asn Tyr Ile
385                 390                 395                 400

Lys Arg Ile Glu Glu Leu Thr Gly Val Pro Ile Asp Ile Ser Thr
            405                 410                 415

Gly Pro Asp Arg Thr Glu Thr Met Ile Leu Arg Asp Pro Phe Asp Ala
            420                 425                 430

<210> SEQ ID NO 35
<211> LENGTH: 54
<212> TYPE: DNA
<213> ORGANISM: Artificial sequence
<220> FEATURE:
<223> OTHER INFORMATION: primer1 for disrupting purA

<400> SEQUENCE: 35
attttgaaaa atgggtaaca acgtcgtcgt actgggcgct caagttagta taaa         54

<210> SEQ ID NO 36
<211> LENGTH: 54
<212> TYPE: DNA
<213> ORGANISM: Artificial sequence
<220> FEATURE:
<223> OTHER INFORMATION: primer2 for disrupting purA

<400> SEQUENCE: 36
gtcgaacggg tcgcgcagaa tcatggtttc agtacgtgaa gcctgctttt ttat         54

<210> SEQ ID NO 37
<211> LENGTH: 1002
<212> TYPE: DNA
<213> ORGANISM: Escherichia coli
<220> FEATURE:
<221> NAME/KEY: CDS
<222> LOCATION: (1)..(999)

<400> SEQUENCE: 37 atg att gat acc acc ctg cca tta act gat atc cat cgc cac ctt gat    48
Met Ile Asp Thr Thr Leu Pro Leu Thr Asp Ile His Arg His Leu Asp
1               5                   10                  15 ggc aac att cgt ccc cag acc att ctt gaa ctt ggc cgc cag tat aat    96
Gly Asn Ile Arg Pro Gln Thr Ile Leu Glu Leu Gly Arg Gln Tyr Asn
```

```
                    20                  25                  30
atc tcg ctt cct gca caa tcc ctg gaa aca ctg att ccc cac gtt cag      144
Ile Ser Leu Pro Ala Gln Ser Leu Glu Thr Leu Ile Pro His Val Gln
        35                  40                  45 gtc att gcc aac gaa ccc gat ctg gtg agc ttt ctg acc aaa ctt gac      192
Val Ile Ala Asn Glu Pro Asp Leu Val Ser Phe Leu Thr Lys Leu Asp
 50                  55                  60 tgg ggc gtt aaa gtt ctc gcc tct ctt gat gcc tgt cgc cgc gtg gca      240
Trp Gly Val Lys Val Leu Ala Ser Leu Asp Ala Cys Arg Arg Val Ala
 65                  70                  75                  80 ttt gaa aac att gaa gat gca gcc cgt cac ggc ctg cac tat gtc gag      288
Phe Glu Asn Ile Glu Asp Ala Ala Arg His Gly Leu His Tyr Val Glu
                 85                  90                  95 ctg cgt ttt tca cca ggc tac atg gca atg gca cat cag ctg cct gta      336
Leu Arg Phe Ser Pro Gly Tyr Met Ala Met Ala His Gln Leu Pro Val
            100                 105                 110 gcg ggt gtt gtc gaa gcg gtg atc gat ggc gta cgt gaa ggt tgc cgc      384
Ala Gly Val Val Glu Ala Val Ile Asp Gly Val Arg Glu Gly Cys Arg
        115                 120                 125 acc ttt ggt gtg cag gcg aag ctt atc ggc att atg agc cgg acc ttc      432
Thr Phe Gly Val Gln Ala Lys Leu Ile Gly Ile Met Ser Arg Thr Phe
130                 135                 140 ggc gaa gcc gcc tgt cag caa gag ctg gag gcc ttt tta gcc cac cgt      480
Gly Glu Ala Ala Cys Gln Gln Glu Leu Glu Ala Phe Leu Ala His Arg
145                 150                 155                 160 gac cag att acc gca ctt gat tta gcc ggt gat gaa ctt ggt ttc ccg      528
Asp Gln Ile Thr Ala Leu Asp Leu Ala Gly Asp Glu Leu Gly Phe Pro
                165                 170                 175 gga agt ctg ttc ctt tct cac ttc aac cgc gcg cgt gat gcg ggc tgg      576
Gly Ser Leu Phe Leu Ser His Phe Asn Arg Ala Arg Asp Ala Gly Trp
            180                 185                 190 cat att acc gtc cat gca ggc gaa gct gcc ggg ccg gaa agc atc tgg      624
His Ile Thr Val His Ala Gly Glu Ala Ala Gly Pro Glu Ser Ile Trp
        195                 200                 205 cag gcg att cgt gaa ctg ggt gcg gag cgt att gga cat ggc gta aaa      672
Gln Ala Ile Arg Glu Leu Gly Ala Glu Arg Ile Gly His Gly Val Lys
210                 215                 220 gcc att gaa gat cgg gcg ctg atg gat ttt ctc gcc gag caa caa att      720
Ala Ile Glu Asp Arg Ala Leu Met Asp Phe Leu Ala Glu Gln Gln Ile
225                 230                 235                 240 ggt att gaa tcc tgt ctg acc tcc aat att cag acc agc acc gta gca      768
Gly Ile Glu Ser Cys Leu Thr Ser Asn Ile Gln Thr Ser Thr Val Ala
                245                 250                 255 gag ctg gct gca cat ccg ctg aaa acg ttc ctt gag cat ggc att cgt      816
Glu Leu Ala Ala His Pro Leu Lys Thr Phe Leu Glu His Gly Ile Arg
            260                 265                 270 gcc agc att aac act gac gat ccc ggc gta cag gga gtg gat atc att      864
Ala Ser Ile Asn Thr Asp Asp Pro Gly Val Gln Gly Val Asp Ile Ile
        275                 280                 285 cac gaa tat acc gtt gcc gcg cca gct gct ggg tta tcc cgc gag caa      912
His Glu Tyr Thr Val Ala Ala Pro Ala Ala Gly Leu Ser Arg Glu Gln
290                 295                 300 atc cgc cag gca cag att aat ggt ctg gaa atg gct ttc ctc agc gct      960
Ile Arg Gln Ala Gln Ile Asn Gly Leu Glu Met Ala Phe Leu Ser Ala
305                 310                 315                 320 gag gaa aaa cgc gca ctg cga gaa aaa gtc gcc gcg aag taa            1002
Glu Glu Lys Arg Ala Leu Arg Glu Lys Val Ala Ala Lys
                325                 330

<210> SEQ ID NO 38
```

```
<211> LENGTH: 333
<212> TYPE: PRT
<213> ORGANISM: Escherichia coli

<400> SEQUENCE: 38

Met Ile Asp Thr Thr Leu Pro Leu Thr Asp Ile His Arg His Leu Asp
1               5                   10                  15

Gly Asn Ile Arg Pro Gln Thr Ile Leu Glu Leu Gly Arg Gln Tyr Asn
            20                  25                  30

Ile Ser Leu Pro Ala Gln Ser Leu Glu Thr Leu Ile Pro His Val Gln
        35                  40                  45

Val Ile Ala Asn Glu Pro Asp Leu Val Ser Phe Leu Thr Lys Leu Asp
50                  55                  60

Trp Gly Val Lys Val Leu Ala Ser Leu Asp Ala Cys Arg Arg Val Ala
65                  70                  75                  80

Phe Glu Asn Ile Glu Asp Ala Ala Arg His Gly Leu His Tyr Val Glu
                85                  90                  95

Leu Arg Phe Ser Pro Gly Tyr Met Ala Met Ala His Gln Leu Pro Val
            100                 105                 110

Ala Gly Val Val Glu Ala Val Ile Asp Gly Val Arg Glu Gly Cys Arg
        115                 120                 125

Thr Phe Gly Val Gln Ala Lys Leu Ile Gly Ile Met Ser Arg Thr Phe
130                 135                 140

Gly Glu Ala Ala Cys Gln Gln Glu Leu Glu Ala Phe Leu Ala His Arg
145                 150                 155                 160

Asp Gln Ile Thr Ala Leu Asp Leu Ala Gly Asp Glu Leu Gly Phe Pro
                165                 170                 175

Gly Ser Leu Phe Leu Ser His Phe Asn Arg Ala Arg Asp Ala Gly Trp
            180                 185                 190

His Ile Thr Val His Ala Gly Glu Ala Ala Gly Pro Glu Ser Ile Trp
        195                 200                 205

Gln Ala Ile Arg Glu Leu Gly Ala Glu Arg Ile Gly His Gly Val Lys
210                 215                 220

Ala Ile Glu Asp Arg Ala Leu Met Asp Phe Leu Ala Glu Gln Gln Ile
225                 230                 235                 240

Gly Ile Glu Ser Cys Leu Thr Ser Asn Ile Gln Thr Ser Thr Val Ala
                245                 250                 255

Glu Leu Ala Ala His Pro Leu Lys Thr Phe Leu Glu His Gly Ile Arg
            260                 265                 270

Ala Ser Ile Asn Thr Asp Asp Pro Gly Val Gln Gly Val Asp Ile Ile
        275                 280                 285

His Glu Tyr Thr Val Ala Ala Pro Ala Ala Gly Leu Ser Arg Glu Gln
290                 295                 300

Ile Arg Gln Ala Gln Ile Asn Gly Leu Glu Met Ala Phe Leu Ser Ala
305                 310                 315                 320

Glu Glu Lys Arg Ala Leu Arg Glu Lys Val Ala Ala Lys
                325                 330

<210> SEQ ID NO 39
<211> LENGTH: 54
<212> TYPE: DNA
<213> ORGANISM: Artificial sequence
<220> FEATURE:
<223> OTHER INFORMATION: primer1 for disrupting add

<400> SEQUENCE: 39
gagtgcgacc atgattgata ccaccctgcc attaaccgct caagttagta taaa          54
```

<210> SEQ ID NO 40
<211> LENGTH: 54
<212> TYPE: DNA
<213> ORGANISM: Artificial sequence
<220> FEATURE:
<223> OTHER INFORMATION: primer2 for disrupting add

<400> SEQUENCE: 40
cttcgcggcg acttttctc gcagtgcgcg tttttctgaa gcctgctttt ttat    54

<210> SEQ ID NO 41
<211> LENGTH: 753
<212> TYPE: DNA
<213> ORGANISM: Escherichia coli
<220> FEATURE:
<221> NAME/KEY: CDS
<222> LOCATION: (1)..(750)

<400> SEQUENCE: 41

| | | | | | | | | | | | | | | | | |
|---|---|---|---|---|---|---|---|---|---|---|---|---|---|---|---|---|
| atg | acc | att | aaa | aat | gta | att | tgc | gat | atc | gac | ggc | gtg | ctg | atg | cac | 48 |
| Met | Thr | Ile | Lys | Asn | Val | Ile | Cys | Asp | Ile | Asp | Gly | Val | Leu | Met | His | |
| 1 | | | | 5 | | | | | 10 | | | | | 15 | | |

| gat | aac | gtc | gcc | gta | ccg | ggt | gca | gcg | gaa | ttt | ttg | cac | ggg | att | atg | 96 |
|---|---|---|---|---|---|---|---|---|---|---|---|---|---|---|---|---|
| Asp | Asn | Val | Ala | Val | Pro | Gly | Ala | Ala | Glu | Phe | Leu | His | Gly | Ile | Met | |
| | | | 20 | | | | | 25 | | | | | 30 | | | |

| gat | aaa | ggc | ctg | ccg | ctg | gtg | ttg | ctg | acc | aac | tat | cct | tcg | cag | act | 144 |
|---|---|---|---|---|---|---|---|---|---|---|---|---|---|---|---|---|
| Asp | Lys | Gly | Leu | Pro | Leu | Val | Leu | Leu | Thr | Asn | Tyr | Pro | Ser | Gln | Thr | |
| | | 35 | | | | | 40 | | | | | 45 | | | | |

| ggg | caa | gat | ctg | gcg | aac | cgc | ttt | gcc | acc | gca | ggt | gtc | gat | gta | cct | 192 |
|---|---|---|---|---|---|---|---|---|---|---|---|---|---|---|---|---|
| Gly | Gln | Asp | Leu | Ala | Asn | Arg | Phe | Ala | Thr | Ala | Gly | Val | Asp | Val | Pro | |
| 50 | | | | | 55 | | | | | 60 | | | | | | |

| gac | agc | gtg | ttt | tat | acc | tct | gcg | atg | gcg | act | gcc | gat | ttc | ctg | cgt | 240 |
|---|---|---|---|---|---|---|---|---|---|---|---|---|---|---|---|---|
| Asp | Ser | Val | Phe | Tyr | Thr | Ser | Ala | Met | Ala | Thr | Ala | Asp | Phe | Leu | Arg | |
| 65 | | | | 70 | | | | | 75 | | | | | 80 | | |

| cgc | cag | gaa | ggc | aag | aaa | gcg | tat | gtg | gtg | ggc | gaa | ggc | gca | ctg | att | 288 |
|---|---|---|---|---|---|---|---|---|---|---|---|---|---|---|---|---|
| Arg | Gln | Glu | Gly | Lys | Lys | Ala | Tyr | Val | Val | Gly | Glu | Gly | Ala | Leu | Ile | |
| | | | | 85 | | | | | 90 | | | | | 95 | | |

| cat | gaa | ctg | tac | aaa | gcc | ggt | ttc | act | att | acc | gat | gtg | aac | cct | gat | 336 |
|---|---|---|---|---|---|---|---|---|---|---|---|---|---|---|---|---|
| His | Glu | Leu | Tyr | Lys | Ala | Gly | Phe | Thr | Ile | Thr | Asp | Val | Asn | Pro | Asp | |
| | | | 100 | | | | | 105 | | | | | 110 | | | |

| ttc | gtg | att | gtt | ggc | gaa | acg | cgt | tcc | tac | aac | tgg | gac | atg | atg | cat | 384 |
|---|---|---|---|---|---|---|---|---|---|---|---|---|---|---|---|---|
| Phe | Val | Ile | Val | Gly | Glu | Thr | Arg | Ser | Tyr | Asn | Trp | Asp | Met | Met | His | |
| | | 115 | | | | | 120 | | | | | 125 | | | | |

| aaa | gca | gcc | tat | ttc | gtc | gct | aac | ggt | gca | cgt | ttt | atc | gcc | acc | aat | 432 |
|---|---|---|---|---|---|---|---|---|---|---|---|---|---|---|---|---|
| Lys | Ala | Ala | Tyr | Phe | Val | Ala | Asn | Gly | Ala | Arg | Phe | Ile | Ala | Thr | Asn | |
| | 130 | | | | | 135 | | | | | 140 | | | | | |

| ccg | gac | acc | cac | ggg | cgc | ggt | ttt | tat | ccc | gct | tgt | ggc | gcg | ttg | tgt | 480 |
|---|---|---|---|---|---|---|---|---|---|---|---|---|---|---|---|---|
| Pro | Asp | Thr | His | Gly | Arg | Gly | Phe | Tyr | Pro | Ala | Cys | Gly | Ala | Leu | Cys | |
| 145 | | | | | 150 | | | | | 155 | | | | | 160 | |

| gca | ggg | att | gag | aaa | atc | tcc | ggg | cgc | aaa | ccg | ttc | tat | gtt | ggt | aag | 528 |
|---|---|---|---|---|---|---|---|---|---|---|---|---|---|---|---|---|
| Ala | Gly | Ile | Glu | Lys | Ile | Ser | Gly | Arg | Lys | Pro | Phe | Tyr | Val | Gly | Lys | |
| | | | | 165 | | | | | 170 | | | | | 175 | | |

| ccc | agc | ccg | tgg | atc | atc | cgc | gca | gca | tta | aac | aaa | atg | cag | gcg | cat | 576 |
|---|---|---|---|---|---|---|---|---|---|---|---|---|---|---|---|---|
| Pro | Ser | Pro | Trp | Ile | Ile | Arg | Ala | Ala | Leu | Asn | Lys | Met | Gln | Ala | His | |
| | | | 180 | | | | | 185 | | | | | 190 | | | |

| tcg | gaa | gaa | acg | gtg | att | gtc | ggc | gat | aac | ctg | cgt | acc | gat | att | ctg | 624 |
|---|---|---|---|---|---|---|---|---|---|---|---|---|---|---|---|---|
| Ser | Glu | Glu | Thr | Val | Ile | Val | Gly | Asp | Asn | Leu | Arg | Thr | Asp | Ile | Leu | |
| | | 195 | | | | | 200 | | | | | 205 | | | | |

| gcc | ggc | ttc | cag | gca | ggt | ctg | gag | acg | att | ctg | gtg | ctt | tct | ggt | gtt | 672 |
|---|---|---|---|---|---|---|---|---|---|---|---|---|---|---|---|---|
| Ala | Gly | Phe | Gln | Ala | Gly | Leu | Glu | Thr | Ile | Leu | Val | Leu | Ser | Gly | Val | |
| | 210 | | | | | 215 | | | | | 220 | | | | | |

```
tcg tcg ctc gac gat atc gac agt atg cct ttc cgc ccc agc tgg att    720
Ser Ser Leu Asp Asp Ile Asp Ser Met Pro Phe Arg Pro Ser Trp Ile
225                 230                 235                 240 tac ccg tca gtc gct gaa atc gac gtt atc tga                        753
Tyr Pro Ser Val Ala Glu Ile Asp Val Ile
                245                 250
```

<210> SEQ ID NO 42
<211> LENGTH: 250
<212> TYPE: PRT
<213> ORGANISM: Escherichia coli

<400> SEQUENCE: 42

```
Met Thr Ile Lys Asn Val Ile Cys Asp Ile Asp Gly Val Leu Met His
1               5                   10                  15

Asp Asn Val Ala Val Pro Gly Ala Ala Glu Phe Leu His Gly Ile Met
            20                  25                  30

Asp Lys Gly Leu Pro Leu Val Leu Leu Thr Asn Tyr Pro Ser Gln Thr
        35                  40                  45

Gly Gln Asp Leu Ala Asn Arg Phe Ala Thr Gly Val Asp Val Pro
    50                  55                  60

Asp Ser Val Phe Tyr Thr Ser Ala Met Ala Thr Ala Asp Phe Leu Arg
65                  70                  75                  80

Arg Gln Glu Gly Lys Lys Ala Tyr Val Val Gly Glu Gly Ala Leu Ile
                85                  90                  95

His Glu Leu Tyr Lys Ala Gly Phe Thr Ile Thr Asp Val Asn Pro Asp
            100                 105                 110

Phe Val Ile Val Gly Glu Thr Arg Ser Tyr Asn Trp Asp Met Met His
        115                 120                 125

Lys Ala Ala Tyr Phe Val Ala Asn Gly Ala Arg Phe Ile Ala Thr Asn
    130                 135                 140

Pro Asp Thr His Gly Arg Gly Phe Tyr Pro Ala Cys Gly Ala Leu Cys
145                 150                 155                 160

Ala Gly Ile Glu Lys Ile Ser Gly Arg Lys Pro Phe Tyr Val Gly Lys
                165                 170                 175

Pro Ser Pro Trp Ile Ile Arg Ala Ala Leu Asn Lys Met Gln Ala His
            180                 185                 190

Ser Glu Glu Thr Val Ile Val Gly Asp Asn Leu Arg Thr Asp Ile Leu
        195                 200                 205

Ala Gly Phe Gln Ala Gly Leu Glu Thr Ile Leu Val Leu Ser Gly Val
    210                 215                 220

Ser Ser Leu Asp Asp Ile Asp Ser Met Pro Phe Arg Pro Ser Trp Ile
225                 230                 235                 240

Tyr Pro Ser Val Ala Glu Ile Asp Val Ile
                245                 250
```

<210> SEQ ID NO 43
<211> LENGTH: 54
<212> TYPE: DNA
<213> ORGANISM: Artificial sequence
<220> FEATURE:
<223> OTHER INFORMATION: primer1 for disrupting nagD

<400> SEQUENCE: 43
tgggtagtcc atgaccatta aaatgtaat tgcgacgct caagttagta taaa    54

<210> SEQ ID NO 44
<211> LENGTH: 54
<212> TYPE: DNA

-continued

```
<213> ORGANISM: Artificial sequence
<220> FEATURE:
<223> OTHER INFORMATION: primer2 for disrupting nagD

<400> SEQUENCE: 44
aacgtcgatt tcagcgactg acgggtaaat ccagcttgaa gcctgctttt ttat            54
```